US008633157B2

(12) United States Patent
DeFrees et al.

(10) Patent No.: US 8,633,157 B2
(45) **Date of Patent: *Jan. 21, 2014**

(54) GLYCOPEGYLATED ERYTHROPOIETIN

(75) Inventors: Shawn DeFrees, North Wales, PA (US); Robert J. Bayer, San Diego, CA (US); David A. Zopf, Wayne, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 137 days.

This patent is subject to a terminal disclaimer.

(21) Appl. No.: 11/144,223

(22) Filed: Jun. 2, 2005

(65) Prior Publication Data

US 2006/0111279 A1 May 25, 2006
US 2010/0210507 A9 Aug. 19, 2010

Related U.S. Application Data

(63) Continuation-in-part of application No. 10/997,405, filed on Nov. 24, 2004, now Pat. No. 7,405,198.

(60) Provisional application No. 60/685,007, filed on May 25, 2005, provisional application No. 60/524,989, filed on Nov. 24, 2003, provisional application No. 60/539,387, filed on Jan. 26, 2004, provisional application No. 60/555,504, filed on Mar. 22, 2004, provisional application No. 60/590,573, filed on Jul. 23, 2004, provisional application No. 60/592,744, filed on Jul. 29, 2004, provisional application No. 60/614,518, filed on Sep. 29, 2004, provisional application No. 60/623,387, filed on Oct. 29, 2004.

(51) Int. Cl.
*A61K 38/18* (2006.01)
*A61P 7/06* (2006.01)
*C07K 14/505* (2006.01)

(52) U.S. Cl.
USPC .......... 514/7.7

(58) Field of Classification Search
None
See application file for complete search history.

(56) References Cited

U.S. PATENT DOCUMENTS 4,055,635 A 10/1977 Green et al.
4,088,538 A 5/1978 Schneider
4,179,337 A 12/1979 Davis et al.
4,385,260 A 5/1983 Watts et al.
4,412,989 A 11/1983 Iwashita et al.
4,414,147 A 11/1983 Klibanov
4,438,253 A 3/1984 Casey et al.
4,496,689 A 1/1985 Mitra
4,565,653 A 1/1986 Ives et al.
4,806,595 A 2/1989 Noishiki et al.
4,826,945 A 5/1989 Cohn et al.
4,847,325 A 7/1989 Shadle et al.
4,879,236 A 11/1989 Smith et al.
4,925,796 A 5/1990 Bergh et al.
5,032,519 A 7/1991 Paulson et al.
5,047,335 A 9/1991 Paulson et al.
5,104,651 A 4/1992 Boone et al.
5,122,614 A 6/1992 Zalipsky
5,147,788 A 9/1992 Page et al.
5,153,265 A 10/1992 Shadle et al.
5,154,924 A 10/1992 Friden
5,169,933 A 12/1992 Anderson et al.
5,182,107 A 1/1993 Friden
5,194,376 A 3/1993 Kang
5,202,413 A 4/1993 Spinu
5,219,564 A 6/1993 Zalipsky et al.
5,281,698 A 1/1994 Nitecki
5,324,663 A 6/1994 Lowe
5,324,844 A 6/1994 Zalipsky
5,342,940 A 8/1994 Ono et al.
5,346,696 A 9/1994 Kim et al.
5,352,670 A 10/1994 Venot
5,369,017 A 11/1994 Wong et al.
5,374,541 A 12/1994 Wong
5,374,655 A 12/1994 Kashem et al.
5,399,345 A 3/1995 Schumacher et al.
5,405,753 A 4/1995 Brossmer
5,410,016 A 4/1995 Hubbell et al.
5,432,059 A 7/1995 Bean
5,446,090 A 8/1995 Harris
5,492,841 A 2/1996 Craig
5,527,527 A 6/1996 Friden
5,529,914 A 6/1996 Hubbell et al.
5,545,553 A 8/1996 Gotschlich
5,583,042 A 12/1996 Roth (Continued)

FOREIGN PATENT DOCUMENTS

CA 2324616 A1 9/1999
CA 2500389 A1 4/2004

(Continued)

OTHER PUBLICATIONS

Abeijon et al., 1986, J. Biol. Chem. 261(24):11374-11377.
Alam et al., 1998. Journal of Biotechnology. 65: 183-190.
Allegre et al., 2006, J. Membrane Science 269:109-117.
Bedard et al., 1994, Cytotechnology 15:129-138.
Bennett et al., 1998, J. Biol. Chem. 273:30472-30481.
Bennett et al., 1999, FEBS Letters 460:226-230.
Bork (2000) Genome Research 10:398-400.
Bork et al. (1996) Trends in Genetics 12(10): 425-427.
Brenner (1999) Trends in Genetics 15(4) 132-133.
Cope et al., 1991, Molecular Microbiology 5(5):1113-1124.
Doerks et al. (1998) Trends in Genetics 14(6): 248-250.
Douglas, et al., 1991, J. Am. Chem. Soc., 113:5095-5097.
Fan et al., 1997, J. Biol. Chem. 272(43):27058-27064.
Fritz et al., 2004, PNAS 101(43):15307-15312.
Fritz et al., 2006, J. Biol. Chem. 281(13):8613-8619.
Gilbert et al., 1996, Cytotechnology 22:211-216.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Hagen et al., 1999, J. Biol. Chem. 274:27867-27874.
Hagen et al., 1999, J. Biol. Chem. 274:6797-6803.
Hagen et al., 2001, J. Biol. Chem. 276:17395-17404.

(Continued)

*Primary Examiner* — Thomas Heard
(74) *Attorney, Agent, or Firm* — Leydig, Voit & Mayer, Ltd.

(57) ABSTRACT

The present invention provides conjugates between erythropoietin and PEG moieties. The conjugates are linked via an intact glycosyl linking group interposed between and covalently attached to the peptide and the modifying group. The conjugates are formed from glycosylated peptides by the action of a glycosyltransferase. The glycosyltransferase ligates a modified sugar moiety onto a glycosyl residue on the peptide. Also provided are methods for preparing the conjugates, methods for treating various disease conditions with the conjugates, and pharmaceutical formulations including the conjugates.

53 Claims, 24 Drawing Sheets

(56) References Cited

U.S. PATENT DOCUMENTS

| | | | | |
|---|---|---|---|---|
| 5,605,793 | A | 2/1997 | Stemmer | |
| 5,614,184 | A | 3/1997 | Sytkowski et al. | |
| 5,621,039 | A | 4/1997 | Hallahan et al. | |
| 5,629,384 | A | 5/1997 | Veronese et al. | |
| 5,635,603 | A | 6/1997 | Hansen et al. | |
| 5,643,575 | A | 7/1997 | Martinez et al. | |
| 5,646,113 | A | 7/1997 | Attie et al. | |
| 5,672,662 | A | 9/1997 | Harris et al. | |
| 5,672,683 | A | 9/1997 | Friden et al. | |
| 5,705,367 | A | 1/1998 | Gotschlich | |
| 5,716,812 | A | 2/1998 | Withers et al. | |
| 5,723,121 | A | 3/1998 | Takenaga et al. | |
| 5,728,554 | A | 3/1998 | Bayer et al. | |
| 5,762,920 | A | 6/1998 | Yung et al. | |
| 5,770,420 | A | 6/1998 | Lowe et al. | |
| 5,798,233 | A | 8/1998 | Gotschlich | |
| 5,811,238 | A | 9/1998 | Stemmer et al. | |
| 5,824,778 | A | 10/1998 | Ishikawa et al. | |
| 5,824,864 | A | 10/1998 | Fox et al. | |
| 5,830,721 | A | 11/1998 | Stemmer et al. | |
| 5,833,988 | A | 11/1998 | Friden | |
| 5,834,251 | A | 11/1998 | Maras et al. | |
| 5,837,458 | A | 11/1998 | Minshull et al. | |
| 5,849,535 | A | 12/1998 | Cunningham et al. | |
| 5,858,751 | A | 1/1999 | Paulson et al. | |
| 5,858,752 | A | 1/1999 | Seed et al. | |
| 5,874,075 | A | 2/1999 | Collins et al. | |
| 5,876,980 | A | 3/1999 | DeFrees et al. | |
| 5,922,577 | A | 7/1999 | DeFrees et al. | |
| 5,932,462 | A | 8/1999 | Harris et al. | |
| 5,945,314 | A | 8/1999 | Prieto et al. | |
| 5,945,322 | A | 8/1999 | Gotschlich | |
| 5,955,347 | A | 9/1999 | Lowe | |
| 5,962,294 | A | 10/1999 | Paulson et al. | |
| 5,969,040 | A | 10/1999 | Hallahan et al. | |
| 5,977,307 | A | 11/1999 | Friden | |
| 6,010,999 | A | 1/2000 | Daley et al. | |
| 6,015,555 | A | 1/2000 | Friden | |
| 6,030,815 | A | 2/2000 | DeFrees et al. | |
| 6,034,223 | A | 3/2000 | Maddon et al. | |
| 6,037,452 | A | 3/2000 | Minamino et al. | |
| 6,057,292 | A | 5/2000 | Cunningham et al. | |
| 6,075,134 | A | 6/2000 | Bertozzi et al. | |
| 6,087,325 | A | 7/2000 | Meers et al. | |
| 6,096,512 | A | 8/2000 | Elhammer et al. | |
| 6,113,906 | A | 9/2000 | Greenwald et al. | |
| 6,117,651 | A | 9/2000 | Schultz et al. | |
| 6,166,183 | A | 12/2000 | Ishikawa et al. | |
| 6,183,738 | B1 | 2/2001 | Clark | |
| 6,251,864 | B1 | 6/2001 | Dower et al. | |
| 6,261,805 | B1 | 7/2001 | Wood | |
| 6,268,193 | B1 | 7/2001 | Lowe | |
| 6,319,695 | B1 | 11/2001 | Wong et al. | |
| 6,342,382 | B1 | 1/2002 | Gotschlich | |
| 6,348,558 | B1 | 2/2002 | Harris et al. | |
| 6,361,977 | B1 | 3/2002 | Bauer et al. | |
| 6,362,254 | B2 | 3/2002 | Harris et al. | |
| 6,376,604 | B2 | 4/2002 | Kozlowski | |
| 6,399,336 | B1 | 6/2002 | Paulson et al. | |
| 6,399,337 | B1 | 6/2002 | Taylor et al. | |
| 6,440,703 | B1 | 8/2002 | DeFrees | |
| 6,465,220 | B1 | 10/2002 | Hassan et al. | |
| 6,495,365 | B1 | 12/2002 | Saito et al. | |
| 6,531,121 | B2 | 3/2003 | Brines et al. | |
| 6,555,346 | B1 | 4/2003 | Kretzdorn et al. | |
| 6,555,660 | B2 | 4/2003 | Nissen et al. | |
| 6,586,398 | B1 | 7/2003 | Kinstler et al. | |
| 6,692,931 | B1 | 2/2004 | Reutter et al. | |
| 6,693,183 | B2 | 2/2004 | Natsuka et al. | |
| 6,716,626 | B1 | 4/2004 | Itoh et al. | |
| 6,743,896 | B2 | 6/2004 | Filpula et al. | |
| 6,780,624 | B2 | 8/2004 | Gotschlich | |
| 6,800,740 | B1 | 10/2004 | Cunningham et al. | |
| 6,949,372 | B2 | 9/2005 | Betenbaugh et al. | |
| 7,094,530 | B1 | 8/2006 | Sasaki et al. | |
| 7,125,843 | B2 | 10/2006 | DeFrees et al. | |
| 7,138,371 | B2 | 11/2006 | DeFrees et al. | |
| 7,157,277 | B2 | 1/2007 | DeFrees et al. | |
| 7,173,003 | B2 | 2/2007 | DeFrees et al. | |
| 7,179,617 | B2 | 2/2007 | DeFrees et al. | |
| 7,202,208 | B2 | 4/2007 | Papadimitriou | |
| 7,214,660 | B2 | 5/2007 | DeFrees et al. | |
| 7,226,903 | B2 | 6/2007 | DeFrees et al. | |
| 7,229,962 | B2 | 6/2007 | Chung et al. | |
| 7,235,638 | B2 | 6/2007 | Persson | |
| 7,265,084 | B2 | 9/2007 | DeFrees et al. | |
| 7,265,085 | B2 | 9/2007 | DeFrees et al. | |
| 7,276,475 | B2 | 10/2007 | DeFrees et al. | |
| 7,297,511 | B2 | 11/2007 | DeFrees et al. | |
| 7,304,150 | B1 | 12/2007 | Egrie et al. | |
| 7,338,933 | B2 | 3/2008 | DeFrees et al. | |
| 7,368,108 | B2 | 5/2008 | DeFrees et al. | |
| 7,399,613 | B2 | 7/2008 | DeFrees et al. | |
| 7,405,198 | B2 * | 7/2008 | DeFrees et al. | 514/8 |
| 7,416,858 | B2 | 8/2008 | DeFrees et al. | |
| 7,439,043 | B2 | 10/2008 | DeFrees et al. | |
| 7,473,680 | B2 | 1/2009 | DeFrees et al. | |
| 7,524,813 | B2 | 4/2009 | Zundel et al. | |
| 7,662,933 | B2 | 2/2010 | Kinstler et al. | |
| 7,691,603 | B2 | 4/2010 | DeFrees | |
| 7,696,163 | B2 | 4/2010 | DeFrees et al. | |
| 7,795,210 | B2 | 9/2010 | DeFrees et al. | |
| 7,803,777 | B2 | 9/2010 | DeFrees | |
| 7,842,661 | B2 | 11/2010 | DeFrees et al. | |
| 7,932,364 | B2 | 4/2011 | DeFrees et al. | |
| 7,956,032 | B2 | 6/2011 | DeFrees et al. | |
| 8,063,015 | B2 | 11/2011 | DeFrees et al. | |
| 8,207,112 | B2 | 6/2012 | Hinderer et al. | |
| 8,247,381 | B2 | 8/2012 | DeFrees | |
| 8,268,967 | B2 | 9/2012 | DeFrees et al. | |
| 8,361,961 | B2 | 1/2013 | DeFrees et al. | |
| 2002/0004483 | A1 | 1/2002 | Nissen et al. | |
| 2002/0016003 | A1 | 2/2002 | Saxon et al. | |
| 2002/0019342 | A1 | 2/2002 | Bayer | |
| 2002/0037841 | A1 | 3/2002 | Papadimitriou | |
| 2002/0115833 | A1 | 8/2002 | Burg et al. | |
| 2002/0137134 | A1 | 9/2002 | Gerngross et al. | |
| 2002/0142370 | A1 | 10/2002 | Paulson et al. | |
| 2002/0148791 | A1 | 10/2002 | DeFrees | |
| 2002/0150981 | A1 | 10/2002 | Canfield | |
| 2002/0168323 | A1 | 11/2002 | Gonda et al. | |
| 2002/0182586 | A1 | 12/2002 | Morris et al. | |
| 2003/0027257 | A1 | 2/2003 | Iatrou et al. | |
| 2003/0040037 | A1 | 2/2003 | Bayer | |
| 2003/0083251 | A1 | 5/2003 | Westenfelder | |
| 2003/0124645 | A1 | 7/2003 | Paulson et al. | |
| 2003/0166212 | A1 | 9/2003 | Taylor et al. | |
| 2003/0166525 | A1 | 9/2003 | Hoffmann et al. | |
| 2003/0180835 | A1 | 9/2003 | Bayer | |
| 2003/0186850 | A1 | 10/2003 | Clausen et al. | |
| 2003/0195338 | A1 | 10/2003 | Chung et al. | |
| 2003/0207406 | A1 | 11/2003 | Johnson et al. | |
| 2004/0043446 | A1 | 3/2004 | DeFrees et al. | |
| 2004/0063911 | A1 | 4/2004 | DeFrees et al. | |
| 2004/0077836 | A1 | 4/2004 | DeFrees et al. | |
| 2004/0082026 | A1 | 4/2004 | DeFrees et al. | |
| 2004/0102607 | A1 | 5/2004 | Danishefsky et al. | |
| 2004/0115168 | A1 | 6/2004 | DeFrees et al. | |
| 2004/0126838 | A1 | 7/2004 | DeFrees et al. | |
| 2004/0132640 | A1 | 7/2004 | DeFrees et al. | |
| 2004/0136955 | A1 | 7/2004 | Barker | |
| 2004/0137557 | A1 * | 7/2004 | DeFrees et al. | 435/68.1 |
| 2004/0197875 | A1 | 10/2004 | Hauser et al. | |
| 2005/0026266 | A1 | 2/2005 | Clausen et al. | |
| 2005/0031584 | A1 | 2/2005 | DeFrees et al. | |
| 2005/0064540 | A1 | 3/2005 | Defrees et al. | |
| 2005/0085631 | A1 | 4/2005 | Boyle et al. | |
| 2005/0100982 | A1 | 5/2005 | DeFrees et al. | |
| 2005/0106658 | A1 | 5/2005 | DeFrees et al. | |
| 2005/0118672 | A1 | 6/2005 | DeFrees et al. | |
| 2005/0143292 | A1 | 6/2005 | DeFrees et al. | |
| 2005/0250678 | A1 | 11/2005 | DeFrees et al. | |
| 2005/0269265 | A1 | 12/2005 | DeFrees | |
| 2005/0271690 | A1 | 12/2005 | Gotschlich | |

(56) References Cited

U.S. PATENT DOCUMENTS

| | | | |
|---|---|---|---|
| 2005/0288490 | A1 | 12/2005 | Nakamoto et al. |
| 2006/0024286 | A1 | 2/2006 | Glidden |
| 2006/0029573 | A1 | 2/2006 | Shen et al. |
| 2006/0030521 | A1 | 2/2006 | DeFrees et al. |
| 2006/0035224 | A1 | 2/2006 | Johansen |
| 2006/0040856 | A1 | 2/2006 | DeFrees et al. |
| 2006/0088906 | A1 | 4/2006 | DeFrees et al. |
| 2006/0111279 | A1 | 5/2006 | DeFrees et al. |
| 2006/0165728 | A1 | 7/2006 | Young et al. |
| 2006/0177892 | A1 | 8/2006 | DeFrees |
| 2006/0182714 | A1 | 8/2006 | Behrens et al. |
| 2006/0183198 | A1 | 8/2006 | Buechler et al. |
| 2006/0246544 | A1 | 11/2006 | Kang et al. |
| 2006/0276618 | A1 | 12/2006 | DeFrees et al. |
| 2006/0287223 | A1 | 12/2006 | DeFrees et al. |
| 2006/0287224 | A1 | 12/2006 | DeFrees et al. |
| 2007/0014759 | A1 | 1/2007 | DeFrees et al. |
| 2007/0026485 | A1 | 2/2007 | DeFrees et al. |
| 2007/0027068 | A1 | 2/2007 | DeFrees et al. |
| 2007/0032405 | A1 | 2/2007 | DeFrees et al. |
| 2007/0037966 | A1 | 2/2007 | Rasmussen et al. |
| 2007/0042458 | A1 | 2/2007 | DeFrees et al. |
| 2007/0059275 | A1 | 3/2007 | DeFrees et al. |
| 2007/0105755 | A1 | 5/2007 | DeFrees et al. |
| 2007/0111926 | A1 | 5/2007 | Zundel et al. |
| 2007/0154992 | A1 | 7/2007 | DeFrees |
| 2007/0254834 | A1 | 11/2007 | DeFrees et al. |
| 2007/0254836 | A1 | 11/2007 | DeFrees et al. |
| 2008/0015142 | A1 | 1/2008 | DeFrees et al. |
| 2008/0050772 | A1 | 2/2008 | DeFrees et al. |
| 2008/0070275 | A1 | 3/2008 | DeFrees et al. |
| 2008/0102083 | A1 | 5/2008 | DeFrees et al. |
| 2008/0108557 | A1 | 5/2008 | Behrens et al. |
| 2008/0146494 | A1 | 6/2008 | DeFrees et al. |
| 2008/0146782 | A1 | 6/2008 | DeFrees et al. |
| 2008/0176790 | A1 | 7/2008 | DeFrees |
| 2008/0187955 | A1 | 8/2008 | DeFrees et al. |
| 2008/0200651 | A1 | 8/2008 | Ostergaard et al. |
| 2008/0206808 | A1 | 8/2008 | DeFrees et al. |
| 2008/0206810 | A1 | 8/2008 | Johnson et al. |
| 2008/0207487 | A1 | 8/2008 | DeFrees et al. |
| 2008/0242607 | A1 | 10/2008 | DeFrees |
| 2008/0242846 | A1 | 10/2008 | DeFrees et al. |
| 2008/0248959 | A1 | 10/2008 | DeFrees |
| 2008/0253992 | A1 | 10/2008 | DeFrees et al. |
| 2008/0255026 | A1 | 10/2008 | DeFrees et al. |
| 2008/0255040 | A1 | 10/2008 | DeFrees |
| 2008/0274958 | A1 | 11/2008 | DeFrees |
| 2008/0280818 | A1 | 11/2008 | DeFrees |
| 2008/0300173 | A1 | 12/2008 | DeFrees |
| 2008/0300175 | A1 | 12/2008 | DeFrees et al. |
| 2008/0305518 | A1 | 12/2008 | Klausen et al. |
| 2008/0305991 | A1 | 12/2008 | DeFrees et al. |
| 2008/0305992 | A1 | 12/2008 | DeFrees et al. |
| 2008/0318850 | A1 | 12/2008 | DeFrees et al. |
| 2008/0319183 | A1 | 12/2008 | DeFrees et al. |
| 2009/0028822 | A1 | 1/2009 | DeFrees et al. |
| 2009/0048440 | A1 | 2/2009 | Felo et al. |
| 2009/0053167 | A1 | 2/2009 | DeFrees |
| 2009/0054623 | A1 | 2/2009 | DeFrees |
| 2009/0055942 | A1 | 2/2009 | Ostergaard et al. |
| 2009/0081188 | A1 | 3/2009 | DeFrees et al. |
| 2009/0093399 | A1 | 4/2009 | DeFrees et al. |
| 2009/0124544 | A1 | 5/2009 | DeFrees |
| 2009/0137763 | A1 | 5/2009 | DeFrees et al. |
| 2009/0143292 | A1 | 6/2009 | Hinderer et al. |
| 2009/0169509 | A1 | 7/2009 | DeFrees et al. |
| 2009/0176967 | A1 | 7/2009 | Stennicke |
| 2009/0203579 | A1 | 8/2009 | DeFrees et al. |
| 2009/0227504 | A1 | 9/2009 | Klausen et al. |
| 2009/0240028 | A1 | 9/2009 | Behrens et al. |
| 2009/0247450 | A1 | 10/2009 | Mack |
| 2009/0252720 | A1 | 10/2009 | Ostergaard et al. |
| 2009/0253166 | A1 | 10/2009 | Zundel et al. |
| 2009/0264366 | A1 | 10/2009 | Johansen et al. |
| 2009/0292110 | A1 | 11/2009 | DeFrees |
| 2009/0305967 | A1 | 12/2009 | DeFrees et al. |
| 2010/0009902 | A1 | 1/2010 | DeFrees |
| 2010/0015684 | A1 | 1/2010 | DeFrees et al. |
| 2010/0028939 | A1 | 2/2010 | Behrens et al. |
| 2010/0029555 | A1 | 2/2010 | Tonon et al. |
| 2010/0035299 | A1 | 2/2010 | DeFrees et al. |
| 2010/0041872 | A1 | 2/2010 | DeFrees et al. |
| 2010/0048456 | A1 | 2/2010 | DeFrees et al. |
| 2010/0056428 | A1 | 3/2010 | Behrens |
| 2010/0075375 | A1 | 3/2010 | DeFrees et al. |
| 2010/0081791 | A1 | 4/2010 | DeFrees et al. |
| 2010/0113743 | A1 | 5/2010 | DeFrees et al. |
| 2010/0120666 | A1 | 5/2010 | Zopf et al. |
| 2010/0174059 | A1 | 7/2010 | DeFrees et al. |
| 2010/0210507 | A9 | 8/2010 | DeFrees et al. |
| 2010/0286067 | A1 | 11/2010 | DeFrees |
| 2010/0322940 | A1 | 12/2010 | Bayer |
| 2010/0330645 | A1 | 12/2010 | DeFrees et al. |
| 2010/0331489 | A1 | 12/2010 | DeFrees |
| 2011/0003744 | A1 | 1/2011 | DeFrees et al. |
| 2011/0177029 | A1 | 7/2011 | DeFrees |
| 2011/0223646 | A1 | 9/2011 | Schwartz et al. |
| 2011/0318780 | A1 | 12/2011 | DeFrees |
| 2012/0016105 | A1 | 1/2012 | DeFrees et al. |
| 2012/0083600 | A1 | 4/2012 | Felo et al. |
| 2012/0107867 | A1 | 5/2012 | DeFrees et al. |
| 2012/0172300 | A1 | 7/2012 | DeFrees |
| 2012/0220517 | A1 | 8/2012 | DeFrees et al. |
| 2013/0059780 | A1 | 3/2013 | DeFrees |

FOREIGN PATENT DOCUMENTS

| | | | |
|---|---|---|---|
| CA | 2511814 | A1 | 7/2004 |
| DE | 19852729 | A1 | 5/2000 |
| EP | 0370205 | A2 | 5/1990 |
| EP | 0459630 | A2 | 12/1991 |
| EP | 0474313 | A | 3/1992 |
| EP | 0585109 | A | 3/1994 |
| EP | 0605963 | A2 | 7/1994 |
| EP | 1270642 | A1 | 1/2003 |
| EP | 1428878 | A1 | 6/2004 |
| JP | H03-503759 | A | 8/1991 |
| JP | H10-307356 | A | 11/1998 |
| JP | H10-540638 | A | 10/2001 |
| JP | 2005-521635 | A | 7/2005 |
| RU | 2005/101348 | A | 8/2005 |
| WO | WO 87/00056 | | 1/1987 |
| WO | WO 87/05330 | A1 | 9/1987 |
| WO | WO 89/06546 | A1 | 7/1989 |
| WO | WO 89/10134 | A1 | 11/1989 |
| WO | WO 90/07572 | A1 | 7/1990 |
| WO | WO 90/08164 | A1 | 7/1990 |
| WO | WO 90/08823 | A1 | 8/1990 |
| WO | WO 90/13540 | A1 | 11/1990 |
| WO | WO 91/14697 | A1 | 10/1991 |
| WO | WO 92/01055 | A1 | 1/1992 |
| WO | WO 92/18135 | | 10/1992 |
| WO | WO 92/22310 | A1 | 12/1992 |
| WO | WO 93/15189 | A1 | 8/1993 |
| WO | WO 94/04193 | A1 | 3/1994 |
| WO | WO 94/05332 | | 3/1994 |
| WO | WO 94/09027 | A1 | 4/1994 |
| WO | WO 94/15625 | A1 | 7/1994 |
| WO | WO 94/17039 | A1 | 8/1994 |
| WO | WO 94/18247 | A1 | 8/1994 |
| WO | WO 94/28024 | A1 | 12/1994 |
| WO | WO 95/02421 | A1 | 1/1995 |
| WO | WO 95/04278 | A1 | 2/1995 |
| WO | WO 96/11953 | A1 | 4/1996 |
| WO | WO 96/40731 | | 6/1996 |
| WO | WO 96/21468 | A1 | 7/1996 |
| WO | WO 96/21469 | A1 | 7/1996 |
| WO | WO 96/32491 | | 10/1996 |
| WO | WO 96/34015 | A1 | 10/1996 |
| WO | WO 96/36357 | A1 | 11/1996 |
| WO | WO 96/40881 | A1 | 12/1996 |
| WO | WO 97/05330 | | 2/1997 |
| WO | WO 98/05363 | | 2/1998 |

(56) References Cited

FOREIGN PATENT DOCUMENTS

| | | | |
|---|---|---|---|
| WO | WO 98/31826 | | 7/1998 |
| WO | WO 98/31826 | A1 | 7/1998 |
| WO | WO 98/41562 | A1 | 9/1998 |
| WO | WO 98/51784 | A1 | 11/1998 |
| WO | WO 98/58964 | | 12/1998 |
| WO | WO 99/00150 | A2 | 1/1999 |
| WO | WO 99/14259 | A1 | 3/1999 |
| WO | WO 99/22764 | A1 | 5/1999 |
| WO | WO 99/22764 | A1 | 5/1999 |
| WO | WO 99/34833 | A1 | 7/1999 |
| WO | WO 99/45964 | A1 | 9/1999 |
| WO | WO 99/48515 | A1 | 9/1999 |
| WO | WO 99/54342 | A1 | 10/1999 |
| WO | WO 99/55376 | A1 | 11/1999 |
| WO | WO 00/23114 | | 4/2000 |
| WO | WO 00/26354 | A1 | 5/2000 |
| WO | WO 00/65087 | | 11/2000 |
| WO | WO 01/02017 | A2 | 1/2001 |
| WO | WO 01/05434 | A2 | 1/2001 |
| WO | WO 01/39788 | A2 | 6/2001 |
| WO | WO 01/49830 | A2 | 7/2001 |
| WO | WO 01/51510 | A2 | 7/2001 |
| WO | WO 01/58493 | A1 | 8/2001 |
| WO | WO 01/58935 | A2 | 8/2001 |
| WO | WO 01/60411 | A1 | 8/2001 |
| WO | WO 01/76640 | A2 | 10/2001 |
| WO | WO 01/88117 | A2 | 11/2001 |
| WO | WO 02/02597 | A2 | 1/2002 |
| WO | WO 02/13843 | A2 | 2/2002 |
| WO | WO 02/13873 | A2 | 2/2002 |
| WO | WO 02/44196 | A1 | 6/2002 |
| WO | WO 02/053580 | A2 | 7/2002 |
| WO | WO 02/074806 | A2 | 9/2002 |
| WO | WO 02/002764 | A2 | 10/2002 |
| WO | WO 02/092619 | A2 | 11/2002 |
| WO | WO 03/017949 | A2 | 3/2003 |
| WO | WO 03/031464 | * | 4/2003 |
| WO | WO 03/031464 | A2 | 4/2003 |
| WO | WO 03/045980 | A2 | 6/2003 |
| WO | WO 03/046150 | A2 | 6/2003 |
| WO | WO 03/093448 | A2 | 11/2003 |
| WO | WO 04/000366 | A1 | 12/2003 |
| WO | WO 2004/009838 | A2 | 1/2004 |
| WO | WO 2004/010327 | A2 | 1/2004 |
| WO | WO 2004/022004 | A2 | 3/2004 |
| WO | WO 2004/033651 | A2 | 4/2004 |
| WO | WO 2004/046222 | A1 | 6/2004 |
| WO | WO 2004/067566 | A1 | 8/2004 |
| WO | WO 2004/083258 | A2 | 9/2004 |
| WO | WO 2004/083259 | A2 | 9/2004 |
| WO | WO 2004/091499 | A2 | 10/2004 |
| WO | WO 2004/096148 | A2 | 11/2004 |
| WO | WO 2004/099231 | A2 | 11/2004 |
| WO | WO 2004/103275 | A2 | 12/2004 |
| WO | WO 2005/012484 | A2 | 2/2005 |
| WO | WO 2005/025606 | A1 | 3/2005 |
| WO | WO 2005/051327 | A2 | 6/2005 |
| WO | WO 2005/055946 | A2 | 6/2005 |
| WO | WO 2005/055950 | A2 | 6/2005 |
| WO | WO 2005/056760 | A2 | 6/2005 |
| WO | WO 2005/067601 | A2 | 7/2005 |
| WO | WO 2005/070138 | A2 | 8/2005 |
| WO | WO 2005/072371 | A2 | 8/2005 |
| WO | WO 2005/091944 | A2 | 10/2005 |
| WO | WO 2005/121331 | A2 | 12/2005 |
| WO | WO 2006/010143 | A2 | 1/2006 |
| WO | WO 2006/011839 | A1 | 2/2006 |
| WO | WO 2006/014349 | A2 | 2/2006 |
| WO | WO 2006/014466 | A2 | 2/2006 |
| WO | WO 2006/020372 | A2 | 2/2006 |
| WO | WO 2006/031811 | A2 | 3/2006 |
| WO | WO 2006/050247 | A2 | 5/2006 |
| WO | WO 2006/074279 | A1 | 7/2006 |
| WO | WO 2006/074467 | A2 | 7/2006 |
| WO | WO 2006/078645 | A2 | 7/2006 |
| WO | WO 2006/082517 | A1 | 8/2006 |
| WO | WO 2006/105426 | A2 | 10/2006 |
| WO | WO 2006/119987 | A2 | 11/2006 |
| WO | WO 2006/121569 | A2 | 11/2006 |
| WO | WO 2006/127910 | A2 | 11/2006 |
| WO | WO 2007/022512 | A2 | 2/2007 |
| WO | WO 2007/056191 | A2 | 5/2007 |
| WO | WO 2008/011633 | A2 | 1/2008 |
| WO | WO 2008/057683 | A2 | 5/2008 |
| WO | WO 2008/060780 | A2 | 5/2008 |
| WO | WO 2008/073620 | A2 | 6/2008 |
| WO | WO 2008/124406 | A2 | 10/2008 |
| WO | WO 2008/151258 | A2 | 12/2008 |
| WO | WO 2008/154639 | A2 | 12/2008 |
| WO | WO 2009/089396 | A2 | 7/2009 |

OTHER PUBLICATIONS

Harris et al., 2003, Nature Reviews Drug Discovery, 2:214-221.
Harris et al., Abstracts of Papers of the American Chemical Society, 1991, V 201, APR, P 64-POLY, p. 154-155.
Hassan et al., 2000, J. Biol. Chem. 275:38197-38205.
Hayes et al., 1993, J. Biol. Chem. 268(22):16170-16178.
Hermentin, et al., 1996, Glycobiology 6(2):217-230.
Hink et al., 1991, Biotechnology Progress 7:9-14.
Hollister et al., 2001, Glycobiology 11:1-9.
Ikonomou et al., 1991, In Vitro Cell. Dev. Biol.-Animal 37:549-559.
Inlow, et al., 1989, J. Tissue Culture Meth. 12:13-16.
Koeller et al., 2001, Nature, 409:232-240.
Lau et al. (1999) Journal of Biotechnology 75:105-115.
Leung, S., 1995, J. Immunology, 154:5919-5926.
Licari P. et al., 1992, Biotechnology and Bioengineering 39(4):432-441.
Licari P. et al., 1992, Biotechnology and Bioengineering 39(9):932-944.
Long et al., 2006, Experimental Hematology 34:697-704.
Maranga et al., 2003, Biotechnology and Bioengineering 84(2):245-253.
NCBI—Accession No. NCAA26095 (2 pgs.), 2007.
NCBI—Accession No. NP_058697 (3 pgs.), 2007.
NCBI—Accession No. NP_999299 (2 pgs.), 2007.
NCBI Database hits for erythropoietin protein sequences (3 pgs.), 2007.
Ngo et al. (1994) "The Protein Folding Problem and Tertiary Structure Prediction, Chapter 14: Computational Complexity Protein Structure Prediction, and the Levinthal Paradox" pp. 433-440 and 492-495.
Oetke, et al., 2002, J. Biol. Chem 277(8):6688-6695.
Plummer et al., 1995, J. Biol. Chem. 270(22):13192-13196.
Reis et al., 1991, Biotechnology and Bioengineering 38:413-422.
Rosenthal, et al., 1994, Methods Enzymol. 235:253-285.
Sandberg et al., 2000, Seminars in Hematology 38(2):4-12.
Schlaeger, E., 1996, Cytotechnology 20:57-70.
Schwientek et al., 2002, J. Biol. Chem. 277:22623-22638.
Shapiro et al., 2005, B. Biochemistry 105:518-525.
Sinha et al., 1980, Infection and Immunity 29(3):914-925.
Skolnick et al. (2000) Trends in Biotech. 18(1): 34-39.
Smith et al. (1997) Nature Biotechnology 15:1222-1223.
Stephens et al., 1983, European J. of Biochem., 133(1):155-62.
Stephens et al., 1983, European J. of Biochem., 133(3):481-9.
Stephens et al., 1983, European J. of Biochem., 135(3):519-27.
Tenno et al., 2002, J. Biol. Chem. 277(49):47088-96.
Tuddenham, E., 2002, Nature 419:23-24.
Wang, M., 1998, Protein Engineering 11(12):1277-1283.
Wells (1990) Biochemistry 29(37): 8509-8517.
Wong et al., 1996, Biotechnology and Bioengineering 49:659-666.
Yoshitake et al., 1985, Biochemistry 24:3736-3750.
Zheng et al., 1999, Biotechnology and Bioengineering 65(5):600-604.
Zhou, et al., 1994, Mol. Microbiol. 14(4):609-618.
Abuchowski et al., *J. Biol. Chem.*, 252(11): 3582-3586 (1977).
Barrios et al., *J. Mol. Recognit.*, 17(4):332-338 (2004).
Bedard et al., *Cytotechnology*, 15(1-3): 129-138 (1994).
Bennett et al., *J. Biol. Chem.*, 273(46): 30472-30481 (1998).
Bennett et al., *FEBS Lett.*, 460(2): 226-230 (1999).

(56) References Cited

OTHER PUBLICATIONS

Berg-Fussman et al., *J. Biol. Chem.*, 268(20): 14861-14866 (1993).
Boime et al., *Recent Prog. Horm. Res.*, 54: 271-289 (1999).
Brenner, *Trends Genet.*, 15(4): 132-133 (1999).
Brockhausen et al., *Acta Anatomica*, 161: 36-78 (1998).
Bueckmann et al., *Makromol. Chem.*, 182(5): 1379-1384 (1981).
Cohn et al., *J. Biomed. Mater. Res*,. 22(11): 993-1009 (1988).
Copeland, "Enzymes: A Practical Introduction to Structure, Mechanism and Data Analysis" 2nd ed., Wiley-VCH, New York, p. 146-150 (2000).
DeFrees et al., *Glycobiology*, 16(9): 833-843 (2006).
Edge et al., *Anal. Biochem.*, 118(1): 131-137 (1981).
Felix et al., *J. Peptide Res.*, 63: 85-90 (2004).
Fritz et al., *Proc. Natl. Acad. Sci. USA*, 101(43): 15307-15312 (2004).
Fritz et al., *J. Biol. Chem.*, 281(13): 8613-8619 (2006).
Ge et al., *J. Biol. Chem.*, 272(34): 21357-21363 (1997).
Gervais et al., *Glycobiology*, 13(3): 179-189 (2003).
Gilbert et al., *Cytotechnology*, 22(1-3): 211-216 (1996).
Gross et al., *Biochemistry*, 28(18): 7386-7392 (1989).
Hagen et al., *J. Biol. Chem.*, 274(10): 6797-6803 (1999).
Hagen et al., *J. Biol. Chem.*, 276(20): 17395-17404 (2001).
Harris et al., *Abstracts of Papers of the American Chemical Society*, 201(4), P 64-POLY, 154-155 (1991).
Harris (ed.), "Poly(Ethylene Glycol) Chemistry: Biotechnical and Biomedical Applications", Plenum Press, New York (1992).
Harris et al. (eds.), "Poly(ethylene glycol): Chemistry and Biological Applications," ACS Symposium Series, vol. 680, American Chemical Society (1997).
Hassan et al., *Carbohydrates in Chemistry and Biology*, Part II, 3: 273-292 (2000).
Hassan et al., *J. Biol. Chem.*, 275(49): 38197-38205 (2000).
Herscovics et al., *FASEB J.*, 7(6): 540-550 (1993).
Hink et al., *Biotechnol. Prog.*, 7(1): 9-14 (1991).
Ikonomou et al., *In Vitro Cell. Dev. Biol. Anim.*, 37(9): 549-559 (1991).
Inlow et al., *J. Tissue Cult. Methods*, 12(1): 13-16 (1989).
Kajihara et al., *Carbohydr. Res.*, 315(1-2): 137-141 (1999).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keppler et al., *Glycobiol.*, 11(2): 11R-18R (2001).
Kobayashi et al., *Eur. J. Nucl. Med.*, 27(9):1334-1339 (2000).
Kornfeld et al., *Ann. Rev. Biochem.*, 54: 631-664 (1985).
Kukuruzinska et al., *Proc. Natl. Acad. Sci. USA*, 84(8): 2145-2149 (1987).
Langer, *Science*, 249(4976): 1527-1533 (1990).
Lau et al., *J. Biotechnol.*, 75(2-3): 105-115 (1999).
Legault et al., *J. Biol. Chem.*, 270(36): 20987-20996 (1995).
Licari et al., *Biotechnol. Bioeng.*, 39(4): 432-441 (1992).
Licari et al., *Biotechnol. Bioeng.*, 39(9): 932-944 (1992).
Lin et al., *Proc. Natl. Acad. Sci. USA*, 82: 7580-7584 (1985).
Liu et al., *Chem. Eur. J.*, 2(11): 1359-1362 (1996).
Meynial-Salles et al., *J. Biotechnol.*, 46(1): 1-14 (1996).
Min et al., *Endocr. J.*, 43(5): 585-593 (1996).
Muller et al., *J. Biol. Chem.*, 272(40): 24780-24793 (1997).
Muller et al., *J. Biol. Chem.*, 274(26): 18165-18172 (1999).
Orlean, "vol. II: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).
Rotondaro et al., *Mol. Biotech.*, 11: 117-128 (1999).
Rudikoff et al., *Proc. Natl. Acad. Sci. USA*, 79(6):1979-1983 (1982).
Sandberg et al., *Semin. Hematol.*, 38(2 Suppl. 4): 4-12 (2001).
Sasaki et al., *J. Biol. Chem.*, 262(25): 12059-12076 (1987).
Sasaki et al., *J. Biol. Chem.*, 269: 14730-14737 (1994).
Schlaeger, *Cytotechnology*, 20(1-3): 57-70 (1996).
Schwientek et al., *J. Biol. Chem.*, 277(25): 22623-22638 (2002).
Seely et al., *J. Chromatog.*, 908: 235-241 (2001).
Seitz, *Chembiochem.*, 1(4): 214-246 (2000).
Shen et al., *Biochem. Biophys. Res. Commun.*, 102(3): 1048-1054 (1981).
Shinkai et al., *Prot. Exp. Purif.*, 10: 379-385 (1997).
Snider et al., *J. Chromatogr.*, A 599(1-2): 141-155 (1992).
Sojar et al., *Arch. Biochem. Biophys.*, 259(1): 52-57 (1987).
Srinivasachar et al., *Biochemistry*, 28(6): 2501-2509 (1989).
Stemmer, *Nature*, 370(6488): 389-391 (1994).
Stemmer, *Proc. Natl. Acad. Sci. USA*, 91(22): 10747-10751 (1994).
Strausberg et al., *Proc Natl Acad Sci USA*, 99(26): 16899-16903 (2002).
Taniguchi et al., *Proteomics*, 1(2): 239-247 (2001).
Ten Hagen et al., *J. Biol. Chem.*, 274(39): 27867-27874 (1999).
Tenno et al., *J. Biol. Chem.*, 277(49): 47088-47096 (2002).
Thotakura et al., *Meth. Enzym.*, 138: 350-359 (1987).
Tsunoda et al., *J. Pharmacol. Exp. Ther.*, 209(1): 368-372 (1999).
Urdal et al, *J. Chromatogr.*, 296: 171-179 (1984).
Van Reis et al., *Biotechnol. Bioeng.*, 38(4): 413-422 (1991).
Vitetta et al., *Science*, 313: 308-309 (2006).
Wang et al., *Protein Eng.*, 11(12): 1277-1283 (1998).
White et al., *J. Biol. Chem.*, 270(41): 24156-24165 (1995).
Witte et al., *J. Am. Chem. Soc.*, 119(9): 2114-2118 (1997).
Witte et al., *Cancer and Metastasis Rev.*, 17: 155-161 (1998).
Wu et al., *J. Drug Target.*, 10(3): 239-245 (2002).
Yamada et al., *Biochemistry*, 20(17): 4836-4842 (1981).
Younes et al., *J. Biomed. Mater. Res.*, 21(11): 1301-1316 (1987).
Zarling et al., *J. Immunol.*, 124(2): 913-920 (1980).
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.

(56) References Cited

OTHER PUBLICATIONS

Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.

(56) References Cited

OTHER PUBLICATIONS

Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Abuchowski et al., 1977, J. Biol. Chem. 252:3582-3586.
Abuchowski et al., 1984, Cancer Biochem. Biophys. 7:175-186.
Abuchowski et al., 1977, J. Biol. Chem. 252:3578-3581.
Ailor et al., 2000, Glycobiology 10:837-847.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Berger et al., 1988, Blood 71:1641-1647.
Berg-Fassman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.
Boissel et al., 1993, J. Biol. Chem. 268:15983-15993.
Bouizar et al., 1986, Eur. J. Biochem. 155:141-147.
Boyd et al., 1995, Mol. Immunol. 32:1311-1318.
Browning et al., 1989, J. Immunol. 143:1859-1867.
Bückmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.

(56) References Cited

OTHER PUBLICATIONS

Cointe, et al., 2000, Glycobiology, 10(5):511-519.
Conradt et al., 1987, J. Biol. Chem. 262:14600-14605.
Copeland, Robert A., 2000, Enzymes, Second Edition, 146-150.
Crout et al., 1998, Curr. Opin. Chem. Biol. 2:98-111.
Delgado et al., 1992, Critical Reviews in Therapeutic 9:249-304.
Delgaldo et al., Biotechnol. Appl. Biochem. 12:119-128.
Detty et al., 1982, J. Org. Chem. 47:5416-5418.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fibi et al., 1995, Cells Blood 85:1229-1236.
Fischer et al., 1998, Thrombosis Research 89:147-150.
Flynn et al., 2000, Curr. Opin. Oncol. 12:574-581.
Garnett et al., 2002, Advanced Drug Delivery Reviews 53:171-216.
Gatot, et al., 1998, J. Biol. Chem., 273(21):12870-12880.
Gillis et al., 1988, Behring Inst. Mitt. Aug. 1983:1-7.
Ginns, Dr. Edward, PEG Glucocerebrosidase, Internet page from www.gaucher.org.uk/peg2.prg, printed Jun. 21, 2002.
Grodberg et al., 1993, Eur. J. Biochem. 218:597-601.
Gross, H.J., 1992, Eur. J. Biochem. 203(1-2):269-275.
Hall et al., 2001, Methods in Molecular Biology 166:139-154.
Haneda et al., Carbohydr. Res. 292:61-70, (1996).
Hang et al., 2001, J. Am. Chem. Soc. 123:1242-1243.
Harris, 1985, Macronol. Chem. Phys. C25: 325-373.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hills et al., 2002, American Biotechnology Laboratory, 20(11):30.
Hollister et al., 2001, Glycobiology 11:1-19.
Hounsell et al., 1996, Glycoconj. J. 13:19-26.
Ichikawa et al., 1992, J. Am. Chem. Soc. 114:9283-9298.
Inoue et al., 1995, Biotechnology Annual Review 1:297-313.
Ito et al., 1992, Pure Appl. Chem. 65:753-762.
Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lee-Huang et al., 1984, Proc. Natl. Acad. Sci. U.S.A. 81:2708-2712.
Lee et al., 1989, Biochemistry 28:1856-1861.
Li et al., 2002, Trends in Pharmacological Sciences 23:206-209.
Li et al., 2002, Medicinal Research Reviews 22:225-250.
Liu et al., 2002, 1996, Chem. Eur. J. 2:1359-1362.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maras et al., 2000, Molecular cloning and enzymatic characterization of a Trichoderma reesei , 2-α-D-mannosidase, 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
Nilsson et al., 1984, Methods Enzymol. 104:56-69.
O'Connell et al., 1992, J. Biol. Chem. 267:25010-25018.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Sadler et al., 1982, Methods in Enzymology 83:458-514.
Saneyoshi et al., 2001, Biology of Reproduction 65:1686-1690.
Saxon et al., 2000, Science 287:2007-2010.
Schwientek et al., 1994, Gene 145:299-303.
Scouten 1987, Methods in Enzymology 135:30-65.
Shah et al., 1996, J. Pharm. Sci. 85:1306-1311.
Singh et al., 1996, Chem. Commun. 1996:993-994.
Song et al., 2002, J. Pharmacol. Exp. Ther. 301:605-610.
Srinivasachar et al., 1989, Biochemistry 28:2501-2509.
Takane et al., 2000, J. Pharmacology and Experimental Therapeutics 294:746-752.
Takeda et al., 1995, Trends Biochem. Sci. 20:367-371.
Tanner et al., 1987, Biochim. Biophys. Acta., 906:81-91.
Taylor et al., 1991, Protein Immobilization Fundamentals and Applications, Manual.
Thotakura et al., 1987, Meth Enzymol 138: 350-359.
Tsuboi et al., 2000 Archives of Biochemistry and Biophysics 374:100-106.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, in Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wellhoner et al., 1991, J. Biol. Chem. 226:4309-4314.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Zalipsky 1995, Bioconjugate Chem. 6:150-165.
Zalipsky et al., 1992, Poly (ethylene glycol) Chemistry: Biotechnical and Biomedical Applications 347-370.
Broun et al., *Science*, 282(5392): 1315-1317 (1998).
Costa et al., *J. Biol. Chem.*, 272(17): 11613-11621 (1997).
De Vries et al, *J. Biol. Chem.*, 270(15): 8712-8722 (1995).
De Vries et al.; *Glycobiology*, 7(7): 921-927 (1997).
Dinter et al., *Biotechnol. Lett.*, 22(1): 25-30 (2000).
Dumas et al., *Bioorg. Med. Chem. Lett.*, 1(8): 425-428 (1991).
Elhalabi et al., *Curr. Med. Chem.*, 6(2): 93-116 (1999).
Espuelas et al., *Bioorg. Med. Chem. Lett.*, 13(15): 2557-2560 (2003).
Fairhall et al., *Endocrinology*, 131(4): 1963-1969 (1992).
Francis et al., *Intl. J. Hematol.*, 68(1): 1-18 (1998).
Hansen et al., *Biochem J.*, 308: 801-813 (1995).
Haro et al., *Biochem. Biophys. Res. Comm.*, 228(2): 549-556 (1996).
Hu et al., *Mol. Cell. Biol.*, 18(10): 6063-6074 (1998).
Kaneko et al., *Cytogenet. Cell Genet.*, 86(3-4): 329-330 (1999).
Kaneko et al., *FEBS Lett.*, 452(3): 237-242 (1999).
Kimura et al., *Proc. Natl. Acad. Sci. USA*, 96(8): 4530-4535 (1999).
Kisselev, *Structure*, 10(1): 8-9 (2002).

(56) References Cited

OTHER PUBLICATIONS

Kukowska-Latallo et al., *Genes Dev.*, 4(8): 1288-1303 (1990).
Leiter et al., *J. Biol. Chem.*, 274(31): 21830-21839 (1999).
Lewis et al., *Endocr. J.*, 47(Suppl.): S1-S8 (2000).
Malissard et al., *Biochem. Biophys. Res. Commun.*, 267(1): 169-173 (2000).
Mollicone et al., *Eur. J. Biochem.*, 191(1): 169-176 (1990).
Natsuka et al., *J. Biol. Chem.*, 269(24): 16789-16794 (1994).
Nunez et al., *Can. J. Chem.*, 59(14): 2086-2095 (1981).
Orskov et al., *J. Biol. Chem.*, 264(22): 12826-12829 (1989).
Palcic et al., *Carbohydr. Res.*, 190(1): 1-11 (1989).
Prieels et al., *J. Biol. Chem.*, 256(20): 10456-10463 (1981).
Rasko et al., *J. Biol. Chem.*, 275(7): 4988-4994 (2000).
R & D Systems, Fibroblast Growth Factors (FGFs), Internet page from www.rndsystems.com/mini_review_detail_objectname_MR01_FGFs.aspx, 2001, printed Mar. 10, 2011.
Seffernick et al., *J. Bacteriol.*, 183(8): 2405-2410 (2001).
Sinclair et al., *J. Pharm. Sci.*, 94: 1626-1635 (2005).
Staudacher, *Trends Glycosci. Glycotechnol.*, 8(44): 391-408 (1996).
Trottein et al., *Mol. Biochem. Parasitol.*, 107(2): 279-287 (2000).
Van Tetering et al., *FEBS Lett.*, 461(3): 311-314 (1999).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(6): 4152-4160 (1992).
Weston et al., *J. Biol. Chem.*, 267(34): 24575-24584 (1992).
Wishart et al., *J. Biol. Chem.*, 270(45): 26782-26785 (1995).
Witkowski et al., *Biochemistry*, 38(36): 11643-11650 (1999).
Zhang et al., *Biochim. Biophys. Acta*, 1425: 441-452 (1998).
Arslan et al., *Transf. Apher. Sci.*, 37: 179-185 (2007).
Broxmeyer et al., *J. Exp. Med.*, 201(8): 1307-1318 (2005).
Brumeanu et al., *J. Immunol. Meth.*, 183: 185-197 (1995).
Cantin et al., *Am. J. Respir. Cell Mol. Biol.*, 27(6): 659-665 (2002).
Capoccia et al., *Blood*, 108(7): 2438-2445 (2006).
Cashen et al., *Bone Marrow Trans.*, 39: 577-588 (2007).
Flomenberg et al., *Blood*, 106(5): 1867-1874 (2005).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
Gross et al., *Eur. J. Biochem*,. 177(3): 583-589 (1988).
Guo et al., *Appl. Biochem. Biotechnol.*, 68(1-2): 1-20 (1997).
Hällgren et al., *J. Carb. Chem.*, 14(4-5): 453-464 (1995).
Haneda et al., *Carbohydr. Res.*, 292: 61-70 (1996).
Hill et al., *Biol. Blood Marrow Trans.*, 12: 603-607 (2006).
Hübel et al., *Ann. Hematol.*, 82: 207-213 (2003).
Kennedy, "Hydrophobic-Interaction Chromatography," in *Current Protocols in Protein Science*, pp. 8.4.1-8.4.21, Wiley (1995).
Kroschinsky et al., *Trans. Apher. Sci.*, 38: 237-244 (2008).
Krystal et al., *Blood*, 67(1): 71-99 (1986).
Liles et al., *Transfusion*, 45: 295-300 (2005).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
O'Shannessy et al., *J. Appl. Biochem.*, 7: 347-355 (1985).
Perrin et al., "Common Physical Techniques Used in Purification," in *Purification of Laboratory Chemicals*, pp. 30-31, Pergamon (1980).
Quelle et al., *Blood*, 74(2): 652-657 (1989).
Rathnam et al., *Biochim. Biophys. Acta*, 624(2): 436-442 (1980).
Schwarz et al., *Nucl. Med. Biol.*, 26(4):383-388 (1999).
Song et al., *Mar. Drugs*, 1: 34-45 (2003).
Srivastava et al., *J. Biol. Chem.*, 267(31): 22356-22361 (1992).
Tom et al., *AAPS Journal*, 9(2): E227-E234 (2007).
UPTIMA, Detergents: Solubilization of Biomolecules, Internet page from www.interchim.com/interchim/bio/produits_uptima/product_line/p1p_detergents.htm, 2001, printed Nov. 14, 2011.
Yin et al., *Pharm. Res.*, 21(12): 2377-2383 (2004).
Amersham Pharmacia Biotech, "Hydrophobic Interaction Chromatography: Principles and Methods," 104 pp. (2000).
Feldman et al., *Proc. Natl. Acad. Sci. USA*, 102(8): 3016-3021 (2005).
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Grabenhorst et al., *J. Biol. Chem.*, 274(51): 36107-36116 (1999).
Höglund, *Med. Oncol.*, 15(4): 229-233 (1998).
Keene et al., *J. Biol. Chem.*, 264(9): 4769-4775 (1989).
Monaco et al., *Gene*, 180: 145-150 (1996).
Nagata et al., *EMBO J.*, 5(3): 575-581 (1986).
Oh-Eda et al., *J. Biol. Chem.*, 265: 11432-11435 (1990).
Prati et al., *Biotech and Bioeng.*, 79(5): 580-585 (2002).
Adelhorst et al., *J. Biol. Chem.*, 269(9): 6275-6278 (1994).
Brockhausen et al., *Glycoconj. J.*, 15: 595-603 (1998).
Culajay et al., *Biochem.*, 39: 7153-7158 (2000).
Dubé et al., *J. Biol. Chem.*, 263(33): 17516-17521 (1988).
Jezek et al., *J. Peptide Sci.*, 5: 46-55 (1999).
Leist et al., *Science*, 305: 239-242 (2004).
Lönnberg, *Curr. Org. Synth.*, 6(4): 400-425 (2009).
Drucker et al., J. Biol. Chem., 263(27): 13475-13478 (1988).
Moscatelli et al., *J. Biol. Chem.*, 236(11): 2858-2862 (1961).
Office Action dated Dec. 21, 2012 in U.S. Appl. No. 13/246,512.
Office Action dated Jan. 17, 2013 in U.S. Appl. No. 13/541,185.
Office Action dated Mar. 6, 2013 in U.S. Appl. No. 13/157,575.
Office Action dated Mar. 13, 2013 in U.S. Appl. No. 12/811,963.
Office Action dated Mar. 14, 2013 in U.S. Appl. No. 12/784,323.
Office Action dated Mar. 21, 2013 in U.S. Appl. No. 13/541,185.
Office Action dated May 9, 2013 in U.S. Appl. No. 12/594,326.
Office Action dated May 21, 2013 in U.S. Appl. No. 12/811,963.
Office Action dated Jun. 6, 2013 in U.S. Appl. No. 11/701,949.
Office Action dated Jul. 11, 2013 in U.S. Appl. No. 11/652,467.
Office Action dated Jul. 17, 2013 in U.S. Appl. No. 13/215,439.
Office Action dated Jul. 30, 2013 in U.S. Appl. No. 13/246,512.
Makoto Takeuchi, et al., "Role of Sugar Chains in the in Vitro Biological Activity of Human Erythropoietin Produced in Recombinant Chinese Hamster Ovary Cells," *The Journal of Biological Chemistry*, 265(21): 12127-12130, 1990.
Office Action dated Aug. 12, 2013 in U.S. Appl. No. 13/541,185.
Office Action dated Sep. 6, 2013 in U.S. Appl. No. 12/784,323.
Deacon, *Diabetes*, 54: 2181-2189 (2004).
PNGase-F Amidase Sequence from *F. meningosepticum* (RN 128688-70-0) (2007).
PNGase-F Amidase Sequence from *F. meningosepticum* (RN 128688-71-1) (2007).
Saxon et al., *J. Am. Chem. Soc.*, 124(50): 14893-14902 (2002).
Veronese, *Biomaterials*, 22(5): 405-417 (2001).
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.
Office Action dated Aug. 8, 2012 in U.S. Appl. No. 13/157,575.
Office Action dated Aug. 17, 2012 in U.S. Appl. No. 12/594,326.
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Office Action dated Oct. 23, 2012 in U.S. Appl. No. 12/811,963.
Office Action dated Nov. 9, 2012 in U.S. Appl. No. 12/663,056.

(56) References Cited

OTHER PUBLICATIONS

Office Action dated Nov. 26, 2012 in U.S. Appl. No. 13/215,439.
Monfardini et al., "A Branched Monomethoxypoly (ethylene glycol) for Protein Modification," *Bioconjug. Chem.*, 6(1): 62-69 (1995).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Office Action dated Sep. 16, 2013 in U.S. Appl. No. 11/781,885.
Office Action dated Sep. 17, 2013 in U.S. Appl. No. 11/781,888.
Office Action dated Sep. 25, 2013 in U.S. Appl. No. 12/663,748.
Office Action dated Oct. 10, 2013 in U.S. Appl. No. 10/581,538.
Office Action dated Oct. 16, 2013 in U.S. Appl. No. 11/597,258.

* cited by examiner

COMPARATIVE PLASMA CLEARANCE RATES FOR PEGYLATED AND NON-PEGYLATED EPO VARIANTS.

| | Non-glycopegylated CHO-EPO | Non-glycopegylated CHO-EPO | Glycopegylated insect-derived EPO | 40K glycopegylated CHO-EPO | Hyper-glycosylated CHO-EPO |
|---|---|---|---|---|---|
| Specific Activity Unit / µg | 1159 | 715 | 223 | 86 | 141 |

FIGURE 9A

| Protein | Organism | EC# | GenBank / GenPept | | SwissProt | PDB /3D |
|---|---|---|---|---|---|---|
| At1g08280 | *Arabidopsis thaliana* | n.d. | AC011438<br>BT004583<br>NC_003070 | AAF18241.1<br>AAO42829.1<br>**NP_172305.1** | Q84W00<br>Q9SGD2 | |
| At1g08660/F22O13.14 | *Arabidopsis thaliana* | n.d. | AC003981<br>AY064135<br>AY124807<br>NC_003070<br>NM_180609 | AAF99778.1<br>**AAL36042.1**<br>AAM70516.1<br>NP_172342.1<br>NP_850940.1 | Q8VZJ0<br>Q9FRR9 | |
| At3g48820/T21J18_90 | *Arabidopsis thaliana* | n.d. | AY080589<br>AY133816<br>AL132963<br>NM_114741 | AAL85966.1<br>AAM91750.1<br>**CAB87910.1**<br>NP_190451.1 | Q8RY00<br>Q9M301 | |
| α-2,3-sialyltransferase (ST3GAL-IV) | *Bos taurus* | n.d. | AJ584673 | **CAE48298.1** | | |
| α-2,3-sialyltransferase (St3Gal-V) | *Bos taurus* | n.d. | AJ585768 | **CAE51392.1** | | |
| α-2,6-sialyltransferase (Siat7b) | *Bos taurus* | n.d. | AJ620651 | **CAF05850.1** | | |
| α-2,8-sialyltransferase (SIAT8A) | *Bos taurus* | 2.4.99.8 | AJ699418 | **CAG27880.1** | | |
| α-2,8-sialyltransferase (Siat8D) | *Bos taurus* | n.d. | AJ699421 | **CAG27883.1** | | |
| α-2,8-sialyltransferase ST8Siα-III (Siat8C) | *Bos taurus* | n.d. | AJ704563 | **CAG28696.1** | | |
| CMP α-2,6-sialyltransferase (ST6Gal I) | *Bos taurus* | 2.4.99.1 | Y15111<br>NM_177517 | CAA75385.1<br>NP_803483.1 | O18974 | |
| sialyltransferase 8 (fragment) | *Bos taurus* | n.d. | AF450088 | **AAL47018.1** | Q8WN13 | |
| sialyltransferase ST3Gal-II (Siat4B) | *Bos taurus* | n.d. | AJ748841 | **CAG44450.1** | | |
| sialyltransferase ST3Gal-III (Siat6) | *Bos taurus* | n.d. | AJ748842 | **CAG44451.1** | | |
| sialyltransferase ST3Gal-VI (Siat10) | *Bos taurus* | n.d. | AJ748843 | **CAG44452.1** | | |
| ST3Gal I | *Bos taurus* | n.d. | AJ305086 | **CAC24698.1** | Q9BEG4 | |
| St6GalNAc-VI | *Bos taurus* | n.d. | AJ620949 | **CAF06586.1** | | |
| CDS4 | *Branchiostoma floridae* | n.d. | AF391289 | **AAM18873.1** | Q8T771 | |
| polysialyltransferase (PST) (fragment) ST8Sia IV | *Cercopithecus aethiops* | 2.4.99.- | AF210729 | **AAF17105.1** | Q9TT09 | |
| polysialyltransferase (STX) (fragment) ST8Sia II | *Cercopithecus aethiops* | 2.4.99.- | AF210318 | **AAF17104.1** | Q9TT10 | |
| α-2,3-sialyltransferase ST3Gal I (Siat4) | *Ciona intestinalis* | n.d. | AJ626815 | **CAF25173.1** | | |
| α-2,3-sialyltransferase ST3Gal I (Siat4) | *Ciona savignyi* | n.d. | AJ626814 | **CAF25172.1** | | |
| α-2,8-polysialyltransferase ST8Sia IV | *Cricetulus griseus* | 2.4.99.- | -<br>Z46801 | AAE28634<br>CAA86822.1 | **Q64690** | |
| Gal β1,3/4-GlcNAc α-2,3-sialyltransferase St3Gal I | *Cricetulus griseus* | n.d. | AY266675 | **AAP22942.1** | Q80WL0 | |
| Gal β1,3/4-GlcNAc α-2,3-sialyltransferase St3Gal II (fragment) | *Cricetulus griseus* | n.d. | AY266676 | **AAP22943.1** | Q80WK9 | |
| α-2,3-sialyltransferase ST3Gal I (Siat4) | *Danio rerio* | n.d. | AJ783740 | **CAH04017.1** | | |
| α-2,3-sialyltransferase ST3Gal II (Siat5) | *Danio rerio* | n.d. | AJ783741 | **CAH04018.1** | | |

FIGURE 9B

| Protein | Organism | EC# | GenBank / GenPept | | SwissProt | PDB / 3D |
|---|---|---|---|---|---|---|
| α-2,3-sialyltransferase ST3Gal III (Siat6) | *Danio rerio* | n.d. | AJ626821 | CAF25179.1 | | |
| α-2,3-sialyltransferase ST3Gal IV (Siat4c) | *Danio rerio* | n.d. | AJ744809 | CAG32845.1 | | |
| α-2,3-sialyltransferase ST3Gal V-r (Siat5-related) | *Danio rerio* | n.d. | AJ783742 | CAH04019.1 | | |
| α-2,6-sialyltransferase ST6Gal I (Siat1) | *Danio rerio* | n.d. | AJ744801 | CAG32837.1 | | |
| α-2,6-sialyltransferase ST6GalNAc II (Siat7B) | *Danio rerio* | n.d. | AJ634459 | CAG25680.1 | | |
| α-2,6-sialyltransferase ST6GalNAc V (Siat7E) (fragment) | *Danio rerio* | n.d. | AJ646874 | CAG26703.1 | | |
| α-2,6-sialyltransferase ST6GalNAc VI (Siat7F) (fragment) | *Danio rerio* | n.d. | AJ646883 | CAG26712.1 | | |
| α-2,8-sialyltransferase ST8Sia I (Siat 8A) (fragment) | *Danio rerio* | n.d. | AJ715535 | CAG29374.1 | | |
| α-2,8-sialyltransferase ST8Sia III (Siat 8C) (fragment) | *Danio rerio* | n.d. | AJ715543 | CAG29382.1 | | |
| α-2,8-sialyltransferase ST8Sia IV (Siat 8D) (fragment) | *Danio rerio* | n.d. | AJ715545 | CAG29384.1 | | |
| α-2,8-sialyltransferase ST8Sia V (Siat 8E) (fragment) | *Danio rerio* | n.d. | AJ715546 | CAG29385.1 | | |
| α-2,8-sialyltransferase ST8Sia VI (Siat 8F) (fragment) | *Danio rerio* | n.d. | AJ715551 | CAG29390.1 | | |
| β-galactosamide α-2,6-sialyltransferase II (ST6Gal II) | *Danio rerio* | n.d. | AJ627627 | CAF29495.1 | | |
| *N*-glycan α-2,8-sialyltransferase | *Danio rerio* | n.d. | BC050483<br>AY055462<br>NM_153662 | AAH50483.1<br>AAL17875.1<br>NP_705948.1 | Q7ZU51<br>Q8QH83 | |
| ST3Gal III-related (siat6r) | *Danio rerio* | n.d. | BC053179<br>AJ626820<br>NM_200355 | AAH53179.1<br>CAF25178.1<br>NP_956649.1 | Q7T3B9 | |
| St3Gal-V | *Danio rerio* | n.d. | AJ619960 | CAF04061.1 | | |
| st6GalNAc-VI | *Danio rerio* | n.d. | BC060932<br>AJ620947 | AAH60932.1<br>CAF06584.1 | | |
| α-2,6-sialyltransferase (CG4871) ST6Gal I | *Drosophila melanogaster* | 2.4.99.1 | AE003465<br>AF218237<br>AF397532<br>AE003465<br>NM_079129<br>NM_166684 | AAF47256.1<br>AAG13185.1<br>AAK92126.1<br>AAM70791.1<br>NP_523853.1<br>NP_726474.1 | Q9GU23<br>Q9W121 | |
| α-2,3-sialyltransferase (ST3Gal-VI) | *Gallus gallus* | n.d. | AJ585767<br>AJ627204 | CAE51391.1<br>CAF25503.1 | | |
| α-2,3-sialyltransferase ST3Gal I | *Gallus gallus* | 2.4.99.4 | X80503<br>NM_205217 | CAA56666.1<br>NP_990548.1 | Q11200 | |
| α-2,3-sialyltransferase ST3Gal IV (fragment) | *Gallus gallus* | 2.4.99.- | AF035250 | AAC14163.1 | O73724 | |
| α-2,3-sialytransferase (ST3GAL-II) | *Gallus gallus* | n.d. | AJ585761 | CAE51385.2 | | |
| α-2,6-sialyltransferase (Siat7b) | *Gallus gallus* | n.d. | AJ620653 | CAF05852.1 | | |
| α-2,6-sialyltransferase ST6Gal I | *Gallus gallus* | 2.4.99.1 | X75558<br>NM_205241 | CAA53235.1<br>NP_990572.1 | Q92182 | |
| α-2,6-sialyltransferase | *Gallus gallus* | 2.4.99.3 | - | AAE68028.1 | Q92183 | |

FIGURE 9C

| Protein | Organism | | EC# | GenBank / GenPept | | SwissProt | PDB / 3D |
|---|---|---|---|---|---|---|---|
| ST6GalNAc I | | | | -<br>X74946<br>NM_205240 | AAE68029.1<br>**CAA52902.1**<br>NP_990571.1 | | |
| α-2,6-sialyltransferase ST6GalNAc II | | *Gallus gallus* | 2.4.99.- | X77775<br>NM_205233 | AAE68030.1<br>**CAA54813.1**<br>NP_990564.1 | Q92184 | |
| α-2,6-sialyltransferase ST6GalNAc III (SIAT7C) (fragment) | | *Gallus gallus* | n.d. | AJ634455 | **CAG25677.1** | | |
| α-2,6-sialyltransferase ST6GalNAc V (SIAT7E) (fragment) | | *Gallus gallus* | n.d. | AJ646877 | **CAG26706.1** | | |
| α-2,8-sialyltransferase (GD3 Synthase) ST8Sia I | | *Gallus gallus* | 2.4.99.- | U73176 | AAC28888.1 | **P79783** | |
| α-2,8-sialyltransferase (SIAT8B) | | *Gallus gallus* | n.d. | AJ699419 | **CAG27881.1** | | |
| α-2,8-sialyltransferase (SIAT8C) | | *Gallus gallus* | n.d. | AJ699420 | **CAG27882.1** | | |
| α-2,8-sialyltransferase (SIAT8F) | | *Gallus gallus* | n.d. | AJ699424 | **CAG27886.1** | | |
| α-2,8-syalyltransferase ST8Siα-V (SIAT8C) | | *Gallus gallus* | n.d. | AJ704564 | **CAG28697.1** | | |
| β-galactosamide α-2,6-sialyltransferase II (ST6Gal II) | | *Gallus gallus* | n.d. | AJ627629 | **CAF29497.1** | | |
| GM3 synthase (SIAT9) | | *Gallus gallus* | 2.4.99.9 | AY515255 | **AAS83519.1** | | |
| polysialyltransferase ST8Sia IV | | *Gallus gallus* | 2.4.99.- | AF008194 | AAB95120.1 | **O42399** | |
| α-2,3-sialyltransferase ST3Gal I | | *Homo sapiens* | 2.4.99.4 | L29555<br>AF059321<br>L13972<br>AF155238<br>AF186191<br>BC018357<br>NM_003033<br>NM_173344 | AAA36612.1<br>AAC17874.1<br>AAC37574.1<br>AAD39238.1<br>**AAG29876.1**<br>AAH18357.1<br>NP_003024.1<br>NP_775479.1 | Q11201<br>O60677<br>Q9UN51 | |
| α-2,3-sialyltransferase ST3Gal II | | *Homo sapiens* | 2.4.99.4 | U63090<br>BC036777<br>X96667<br>NM_006927 | AAB40389.1<br>**AAH36777.1**<br>CAA65447.1<br>NP_008858.1 | Q16842<br>O00654 | |
| α-2,3-sialyltransferase ST3Gal III (SiaT6) | | *Homo sapiens* | 2.4.99.6 | L23768<br>BC050380<br>AF425851<br>AF425852<br>AF425853<br>AF425854<br>AF425855<br>AF425856<br>AF425857<br>AF425858<br>AF425859<br>AF425860<br>AF425861<br>AF425862<br>AF425863<br>AF425864<br>AF425865<br>AF425866<br>AF425867<br>AY167992<br>AY167993<br>AY167994 | AAA35778.1<br>AAH50380.1<br>AAO13859.1<br>AAO13860.1<br>AAO13861.1<br>AAO13862.1<br>AAO13863.1<br>AAO13864.1<br>AAO13865.1<br>AAO13866.1<br>AAO13867.1<br>AAO13868.1<br>AAO13869.1<br>**AAO13870.1**<br>AAO13871.1<br>AAO13872.1<br>AAO13873.1<br>AAO13874.1<br>AAO13875.1<br>AAO38806.1<br>AAO38807.1<br>AAO38808.1 | Q11203<br>Q86UR6<br>Q86UR7<br>Q86UR8<br>Q86UR9<br>Q86US0<br>Q86US1<br>Q86US2<br>Q8IX43<br>Q8IX44<br>Q8IX45<br>Q8IX46<br>Q8IX47<br>Q8IX48<br>Q8IX49<br>Q8IX50<br>Q8IX51<br>Q8IX52<br>Q8IX53<br>Q8IX54<br>Q8IX55<br>Q8IX56 | |

FIGURE 9D

| Protein | Organism | EC# | GenBank / GenPept | | SwissProt | PDB / 3D |
|---|---|---|---|---|---|---|
| | | | AY167995<br>AY167996<br>AY167997<br>AY167998<br>NM_006279<br>NM_174964<br>NM_174965<br>NM_174966<br>NM_174967<br>NM_174969<br>NM_174970<br>NM_174972 | AAO38809.1<br>AAO38810.1<br>AAO38811.1<br>AAO38812.1<br>NP_006270.1<br>NP_777624.1<br>NP_777625.1<br>NP_777626.1<br>NP_777627.1<br>NP_777629.1<br>NP_777630.1<br>NP_777632.1 | Q8IX57<br>Q8IX58 | |
| α-2,3-sialyltransferase ST3Gal IV | *Homo sapiens* | 2.4.99.- | L23767<br>AF035249<br>BC010645<br>AY040826<br>AF516602<br>AF516603<br>AF516604<br>AF525084<br>X74570<br>CR456858<br>NM_006278 | AAA16460.1<br>AAC14162.1<br>**AAH10645.1**<br>AAK93790.1<br>AAM66431.1<br>AAM66432.1<br>AAM66433.1<br>AAM81378.1<br>CAA52662.1<br>CAG33139.1<br>NP_006269.1 | Q11206<br>O60497<br>Q96QQ9<br>Q8N6A6<br>Q8N6A7<br>Q8NFD3<br>Q8NFG7 | |
| α-2,3-sialyltransferase ST3Gal VI | *Homo sapiens* | 2.4.99.4 | AF119391<br>BC023312<br>AB022918<br>AX877828<br>AX886023<br>NM_006100 | **AAD39131.1**<br>AAH23312.1<br>BAA77609.1<br>CAE89895.1<br>CAF00161.1<br>NP_006091.1 | Q9Y274 | |
| α-2,6-sialyltransferase (ST6Gal II ; KIAA1877) | *Homo sapiens* | n.d. | BC008680<br>AB058780<br>AB059555<br>AJ512141<br>AX795193<br>AX795193<br>NM_032528 | AAH08680.1<br>**BAB47506.1**<br>BAC24793.1<br>CAD54408.1<br>CAE48260.1<br>CAE48261.1<br>NP_115917.1 | Q86Y44<br>Q8IUG7<br>Q96HE4<br>Q96JF0 | |
| α-2,6-sialyltransferase (ST6GALNAC III) | *Homo sapiens* | n.d. | BC059363<br>AY358540<br>AK091215<br>AJ507291<br>NM_152996 | AAH59363.1<br>AAQ88904.1<br>BAC03611.1<br>**CAD45371.1**<br>NP_694541.1 | Q8N259<br>Q8NDV1 | |
| α-2,6-sialyltransferase (ST6GalNAc V) | *Homo sapiens* | n.d. | BC001201<br>AK056241<br>AL035409<br>AJ507292<br>NM_030965 | **AAH01201.1**<br>BAB71127.1<br>CAB72344.1<br>CAD45372.1<br>NP_112227.1 | Q9BVH7 | |
| α-2,6-sialyltransferase (SThM) ST6GalNAc II | *Homo sapiens* | 2.4.99.- | U14550<br>BC040455<br>AJ251053<br>NM_006456 | AAA52228.1<br>**AAH40455.1**<br>CAB61434.1<br>NP_006447.1 | Q9UJ37<br>Q12971 | |
| α-2,6-sialyltransferase ST6Gal I | *Homo sapiens* | 2.4.99.1 | BC031476<br>BC040009<br>A17362<br>A23699<br>X17247<br>X54363<br>X62822<br>NM_003032<br>NM_173216 | AAH31476.1<br>AAH40009.1<br>**CAA01327.1**<br>CAA01686.1<br>CAA35111.1<br>CAA38246.1<br>CAA44634.1<br>NP_003023.1<br>NP_775323.1 | P15907 | |
| α-2,6-sialyltransferase ST6GalNAc I | *Homo sapiens* | 2.4.99.3 | BC022462<br>AY096001<br>AY358918<br>AK000113<br>Y11339 | AAH22462.1<br>AAM22800.1<br>AAQ89277.1<br>BAA90953.1<br>**CAA72179.2** | Q8TBJ6<br>Q9NSC7<br>Q9NXQ7 | |

FIGURE 9E

| Protein | Organism | | EC# | GenBank / GenPept | | SwissProt | PDB / 3D |
|---|---|---|---|---|---|---|---|
| | | | | NM_018414 | NP_060884.1 | | |
| α-2,8-polysialyltransferase ST8Sia IV | | *Homo sapiens* | 2.4.99.- | L41680<br>BC027866<br>BC053657<br>NM_005668 | AAC41775.1<br>AAH27866.1<br>**AAH53657.1**<br>NP_005659.1 | Q8N1F4<br>Q92187<br>Q92693 | |
| α-2,8-sialyltransferase (GD3 synthase) ST8Sia I | | *Homo sapiens* | 2.4.99.8 | L32867<br>L43494<br>BC046158<br>-<br>AY569975<br>D26360<br>X77922<br>NM_003034 | AAA62366.1<br>**AAC37586.1**<br>AAH46158.1<br>AAQ53140.1<br>AAS75783.1<br>BAA05391.1<br>CAA54891.1<br>NP_003025.1 | Q86X71<br>Q92185<br>Q93064 | |
| α-2,8-sialyltransferase ST8Sia II | | *Homo sapiens* | 2.4.99.- | L29556<br>U82762<br>U33551<br>BC069584<br>NM_006011 | AAA36613.1<br>AAB51242.1<br>**AAC24458.1**<br>AAH69584.1<br>NP_006002.1 | Q92186<br>Q92470<br>Q92746 | |
| α-2,8-sialyltransferase ST8Sia III | | *Homo sapiens* | 2.4.99.- | AF004668<br>AF003092<br>NM_015879 | **AAB87642.1**<br>AAC15901.2<br>NP_056963.1 | O43173<br>Q9NS41 | |
| α-2,8-sialyltransferase ST8Sia V | | *Homo sapiens* | 2.4.99.- | U91641<br>CR457037<br>NM_013305 | **AAC51727.1**<br>CAG33318.1<br>NP_037437.1 | O15466 | |
| ENSP00000020221 (fragment) | | | n.d. | AC023295 | - | | |
| lactosylceramide α-2,3-sialyltransferase (ST3Gal V) | | *Homo sapiens* | 2.4.99.9 | AF105026<br>AF119415<br>BC065936<br>AY152815<br>AAP65066<br>AY359105<br>AB018356<br>AX876536<br>NM_003896 | **AAD14634.1**<br>AAF66146.1<br>AAH65936.1<br>AAO16866.1<br>AAP65066.1<br>AAQ89463.1<br>BAA33950.1<br>CAE89320.1<br>NP_003887.2 | Q9UNP4<br>O94902 | |
| *N*-acetylgalactosaminide α-2,6-sialyltransferase (ST6GalNAc VI) | | *Homo sapiens* | 2.4.99.- | BC006564<br>BC007802<br>BC016299<br>AY358672<br>AB035173<br>AK023900<br>AJ507293<br>AX880950<br>CR457318<br>NM_013443 | AAH06564.1<br>AAH07802.1<br>AAH16299.1<br>AAQ89035.1<br>**BAA87035.1**<br>BAB14715.1<br>CAD45373.1<br>CAE91145.1<br>CAG33599.1<br>NP_038471.2 | Q969X2<br>Q9H8A2<br>Q9ULB8 | |
| *N*-acetylgalactosaminide α-2,6-sialyltransferase IV (ST6GalNAc IV) | | *Homo sapiens* | 2.4.99.- | AF127142<br>BC036705<br>-<br>AB035172<br>AK000600<br>Y17461<br>AJ271734<br>AX061620<br>AX068265<br>AX969252<br>NM_014403<br>NM_175039 | AAF00102.1<br>AAH36705.1<br>AAP63349.1<br>**BAA87034.1**<br>BAA91281.1<br>CAB44354.1<br>CAC07404.1<br>CAC24981.1<br>CAC27250.1<br>CAF14360.1<br>NP_055218.3<br>NP_778204.1 | Q9H4F1<br>Q9NWU6<br>Q9UKU1<br>Q9ULB9<br>Q9Y3G3<br>Q9Y3G4 | |
| ST8SIA-VI (fragment) | | *Homo sapiens* | n.d. | AJ621583<br>XM_291725 | **CAF21722.1**<br>XP_291725.2 | | |
| unnamed protein product | | *Homo sapiens* | n.d. | AK021929<br>AX881696 | **BAB13940.1**<br>CAE91353.1 | Q9HAA9 | |
| Gal β-1,3/4-GlcNAc α- | | *Mesocricetus* | 2.4.99.6 | AJ245699 | **CAB53394.1** | Q9QXF6 | |

FIGURE 9F

| Protein | Organism | | EC# | GenBank / GenPept | | SwissProt | PDB / 3D |
|---|---|---|---|---|---|---|---|
| 2,3-sialyltransferase (ST3Gal III) | | *auratus* | | | | | |
| Gal β-1,3/4-GlcNAc α-2,3-sialyltransferase (ST3Gal IV) | | *Mesocricetus auratus* | 2.4.99.6 | AJ245700 | **CAB53395.1** | Q9QXF5 | |
| GD3 synthase (fragment) ST8Sia I | | *Mesocricetus auratus* | n.d. | AF141657 | **AAD33879.1** | Q9WUL1 | |
| polysialyltransferase (ST8Sia IV) | | *Mesocricetus auratus* | 2.4.99.- | AJ245701 | **CAB53396.1** | Q9QXF4 | |
| α-2,3-sialyltransferase ST3Gal I | *St3gal1* | *Mus musculus* | 2.4.99.4 | AF214028<br>AK031344<br>AK078469<br>X73523<br>NM_009177 | AAF60973.1<br>BAC27356.1<br>BAC37290.1<br>CAA51919.1<br>NP_033203.1 | **P54751**<br>**Q11202**<br>Q9JL30 | |
| α-2,3-sialyltransferase ST3Gal II | *St3gal2* | *Mus musculus* | 2.4.99.4 | BC015264<br>BC066064<br>AK034554<br>AK034863<br>AK053827<br>X76989<br>NM_009179<br>NM_178048 | **AAH15264.1**<br>AAH66064.1<br>BAC28752.1<br>BAC28859.1<br>BAC35543.1<br>CAA54294.1<br>NP_033205.1<br>NP_835149.1 | Q11204<br>Q8BPL0<br>Q8BSA0<br>Q8BSE9<br>Q91WH6 | |
| α-2,3-sialyltransferase ST3Gal III | *St3gal3* | *Mus musculus* | 2.4.99.- | BC006710<br>AK005053<br>AK013016<br>X84234<br>NM_009176 | AAH06710.1<br>**BAB23779.1**<br>BAB28598.1<br>CAA59013.1<br>NP_033202.2 | P97325<br>Q922X5<br>Q9CZ48<br>Q9DBB6 | |
| α-2,3-sialyltransferase ST3Gal IV | *St3gal4* | *Mus musculus* | 2.4.99.4 | BC011121<br>BC050773<br>D28941<br>AK008543<br>AB061305<br>X95809<br>NM_009178 | AAH11121.1<br>**AAH50773.1**<br>BAA06068.1<br>BAB25732.1<br>BAB47508.1<br>CAA65076.1<br>NP_033204.2 | P97354<br>Q61325<br>Q91Y74<br>Q921R5<br>Q9CVE8 | |
| α-2,3-sialyltransferase ST3Gal VI | *St3gal6* | *Mus musculus* | 2.4.99.4 | AF119390<br>BC052338<br>AB063326<br>AK033562<br>AK041173<br>NM_018784 | AAD39130.1<br>AAH52338.1<br>**BAB79494.1**<br>BAC28360.1<br>BAC30851.1<br>NP_061254 | Q80UR7<br>Q8BLV1<br>Q8VIB3<br>Q9WVG2 | |
| α-2,6-sialyltransferase ST6GalNAc II | *St6galnac2* | *Mus musculus* | 2.4.99.- | NM_009180<br>BC010208<br>AB027198<br>AK004613<br>X93999<br>X94000<br>NM_009180 | 6677963<br>AAH10208.1<br>BAB00637.1<br>BAB23410.1<br>CAA63821.1<br>CAA63822.1<br>NP_033206.2 | **P70277**<br>Q9DC24<br>Q9JJM5 | |
| α-2,6-sialyltransferase ST6Gal I | *St6gal1* | *Mus musculus* | 2.4.99.1 | -<br>BC027833<br>D16106<br>AK034768<br>AK084124<br>NM_145933 | AAE68031.1<br>AAH27833.1<br>BAA03680.1<br>BAC28828.1<br>BAC39120.1<br>NP_666045.1 | **Q64685**<br>Q8BM62<br>Q8K1L1 | |
| α-2,6-sialyltransferase ST6Gal II | *St6gal2* | *Mus musculus* | n.d. | AK082566<br>AB095093<br>AK129462<br>NM_172829 | BAC38534.1<br>**BAC87752.1**<br>BAC98272.1<br>NP_766417.1 | Q8BUU4 | |
| α-2,6-sialyltransferase ST6GalNAc I | *St6galnac1* | *Mus musculus* | 2.4.99.3 | Y11274<br>NM_011371 | **CAA72137.1**<br>NP_035501.1 | Q9QZ39<br>Q9JJP5 | |
| α-2,6-sialyltransferase ST6GalNAc III | *St6galnac3* | *Mus musculus* | n.d. | BC058387<br>AK034804<br>Y11342<br>Y11343 | AAH58387.1<br>BAC28836.1<br>CAA72181.2<br>**CAB95031.1** | Q9WUV2<br>Q9JHP5 | |

FIGURE 9G

| Protein | Organism | | EC# | GenBank / GenPept | | SwissProt | PDB / 3D |
|---|---|---|---|---|---|---|---|
| | | | | NM_011372 | NP_035502 | | |
| α-2,6-sialyltransferase ST6GalNAc IV | *St6galnac4* | *Mus musculus* | 2.4.99.7 | BC056451<br>AK085730<br>AJ007310<br>Y15779<br>Y15780<br>Y19055<br>Y19057<br>NM_011373 | AAH56451.1<br>BAC39523.1<br>CAA07446.1<br>CAB43507.1<br>**CAB43514.1**<br>CAB93946.1<br>CAB93948.1<br>NP_035503.1 | Q8C3J2<br>Q9JHP2<br>Q9R2B6<br>O88725<br>Q9JHP0<br>Q9QUP9<br>Q9R2B5 | |
| α-2,8-sialyltransferase (GD3 synthase) ST8Sia I | *St8sia1* | *Mus musculus* | 2.4.99.8 | L38677<br>BC024821<br>AK046188<br>AK052444<br>X84235<br>AJ401102<br>NM_011374 | AAA91869.1<br>**AAH24821.1**<br>BAC32625.1<br>BAC34994.1<br>CAA59014.1<br>CAC20706.1<br>NP_035504.1 | Q64468<br>Q64687<br>Q8BL76<br>Q8BWI0<br>Q8K1C1<br>Q9EPK0 | |
| α-2,8-sialyltransferase (ST8Sia VI) | *St8sia6* | *Mus musculus* | n.d. | AB059554<br>AK085105<br>NM_145838 | **BAC01265.1**<br>BAC39367.1<br>NP_665837.1 | Q8BI43<br>Q8K4T1 | |
| α-2,8-sialyltransferase ST8Sia II | *St8sia2* | *Mus musculus* | 2.4.99.- | X83562<br>X99646<br>X99647<br>X99648<br>X99649<br>X99650<br>X99651<br>NM_009181 | CAA58548.1<br>CAA67965.1<br>CAA67965.1<br>CAA67965.1<br>CAA67965.1<br>CAA67965.1<br>CAA67965.1<br>NP_033207.1 | **O35696** | |
| α-2,8-sialyltransferase ST8Sia IV | *St8sia4* | *Mus musculus* | 2.4.99.8 | BC060112<br>AK003690<br>AK041723<br>AJ223956<br>X86000<br>Y09484<br>NM_009183 | AAH60112.1<br>BAB22941.1<br>BAC31044.1<br>**CAA11685.1**<br>CAA59992.1<br>CAA70692.1<br>NP_033209.1 | Q64692<br>Q8BY70 | |
| α-2,8-sialyltransferase ST8Sia V | *St8sia5* | *Mus musculus* | 2.4.99.- | BC034855<br>AK078670<br>X98014<br>X98014<br>X98014<br>NM_013666<br>NM_153124<br>NM_177416 | AAH34855.1<br>BAC37354.1<br>**CAA66642.1**<br>CAA66643.1<br>CAA66644.1<br>NP_038694.1<br>NP_694764.1<br>NP_803135.1 | P70126<br>P70127<br>P70128<br>Q8BJW0<br>Q8JZQ3 | |
| α-2,8-sialytransferase ST8Sia III | *St8sia3* | *Mus musculus* | 2.4.99.- | BC075645<br>AK015874<br>X80502<br>NM_009182 | AAH75645.1<br>BAB30012.1<br>CAA56665.1<br>NP_033208.1 | **Q64689**<br>Q9CUJ6 | |
| GD1 synthase (ST6GalNAc V) | *St6galnac5* | *Mus musculus* | n.d. | BC055737<br>AB030836<br>AB028840<br>AK034387<br>AK038434<br>AK042683<br>NM_012028 | **AAH55737.1**<br>BAA85747.1<br>BAA89292.1<br>BAC28693.1<br>BAC29997.1<br>BAC31331.1<br>NP_036158.2 | Q8CAM7<br>Q8CBX1<br>Q9QYJ1<br>Q9R0K6 | |
| GM3 synthase (α-2,3-sialyltransferase) ST3Gal V | *St3gal5* | *Mus musculus* | 2.4.99.9 | AF119416<br>-<br>AB018048<br>AB013302<br>AK012961<br>Y15003<br>NM_011375 | **AAF66147.1**<br>AAP65063.1<br>BAA33491.1<br>BAA76467.1<br>BAB28571.1<br>CAA75235.1<br>NP_035505.1 | O88829<br>Q9CZ65<br>Q9QWF9 | |
| *N*-acetylgalactosaminide α-2,6-sialyltransferase (ST6GalNAc VI) | *St6galnac6* | *Mus musculus* | 2.4.99.- | BC036985<br>AB035174<br>AB035123<br>AK030648 | **AAH36985.1**<br>BAA87036.1<br>BAA95940.1<br>BAC27064.1 | Q8CDC3<br>Q8JZW3<br>Q9JM95<br>Q9R0G9 | |

FIGURE 9H

| Protein | Organism | | EC# | GenBank / GenPept | | SwissProt | PDB / 3D |
|---|---|---|---|---|---|---|---|
| | | | | NM_016973 | NP_058669.1 | | |
| M138L | | *Myxoma virus* | n.d. | U46578<br>AF170726<br>NC_001132 | AAD00069.1<br>AAE61323.1<br>AAE61326.1<br>**AAF15026.1**<br>NP_051852.1 | | |
| α-2,3-sialyltransferase (St3Gal-I) | | *Oncorhynchus mykiss* | n.d. | AJ585760 | **CAE51384.1** | | |
| α-2,6-sialyltransferase (Siat1) | | *Oncorhynchus mykiss* | n.d. | AJ620649 | **CAF05848.1** | | |
| α-2,8-polysialyltransferase IV (ST8Sia IV) | | *Oncorhynchus mykiss* | n.d. | AB094402 | **BAC77411.1** | Q7T2X5 | |
| GalNAc α-2,6-sialyltransferase (RtST6GalNAc) | | *Oncorhynchus mykiss* | n.d. | AB097943 | **BAC77520.1** | Q7T2X4 | |
| α-2,3-sialyltransferase ST3Gal IV | | *Oryctolagus cuniculus* | 2.4.99.- | AF121967 | **AAF28871.1** | Q9N257 | |
| OJ1217_F02.7 | | *Oryza sativa (japonica cultivar-group)* | n.d. | AP004084 | **BAD07616.1** | | |
| OSJNBa0043L24.2 or OSJNBb0002J11.9 | | *Oryza sativa (japonica cultivar-group)* | n.d. | AL731626<br>AL662969 | **CAD41185.1**<br>CAE04714.1 | | |
| P0683f02.18 or P0489B03.1 | | *Oryza sativa (japonica cultivar-group)* | n.d. | AP003289<br>AP003794 | **BAB63715.1**<br>BAB90552.1 | | |
| α-2,6-sialyltransferase ST6GalNAc V (Siat7E) (fragment) | | *Oryzias latipes* | n.d. | AJ646876 | **CAG26705.1** | | |
| α-2,3-sialyltransferase ST3Gal I (Siat4) | | *Pan troglodytes* | n.d. | AJ744803 | **CAG32839.1** | | |
| α-2,3-sialyltransferase ST3Gal II (Siat5) | | *Pan troglodytes* | n.d. | AJ744804 | **CAG32840.1** | | |
| α-2,3-sialyltransferase ST3Gal III (Siat6) | | *Pan troglodytes* | n.d. | AJ626819 | **CAF25177.1** | | |
| α-2,3-sialyltransferase ST3Gal IV (Siat4c) | | *Pan troglodytes* | n.d. | AJ626824 | **CAF25182.1** | | |
| α-2,3-sialyltransferase ST3Gal VI (Siat10) | | *Pan troglodytes* | n.d. | AJ744808 | **CAG32844.1** | | |
| α-2,6-sialyltransferase (Sia7A) | | *Pan troglodytes* | n.d. | AJ748740 | **CAG38615.1** | | |
| α-2,6-sialyltransferase (Sia7B) | | *Pan troglodytes* | n.d. | AJ748741 | **CAG38616.1** | | |
| α-2,6-sialyltransferase ST6GalNAc III (Siat7C) | | *Pan troglodytes* | n.d. | AJ634454 | **CAG25676.1** | | |
| α-2,6-sialyltransferase ST6GalNAc IV (Siat7D) (fragment) | | *Pan troglodytes* | n.d. | AJ646870 | **CAG26699.1** | | |
| α-2,6-sialyltransferase ST6GalNAc V (Siat7E) | | *Pan troglodytes* | n.d. | AJ646875 | **CAG26704.1** | | |
| α-2,6-sialyltransferase ST6GalNAc VI (Siat7F) (fragment) | | *Pan troglodytes* | n.d. | AJ646882 | **CAG26711.1** | | |
| α-2,8-sialyltransferase 8A (Siat8A) | | *Pan troglodytes* | 2.4.99.8 | AJ697658 | **CAG26896.1** | | |
| α-2,8-sialyltransferase 8B (Siat8B) | | *Pan troglodytes* | n.d. | AJ697659 | **CAG26897.1** | | |
| α-2,8-sialyltransferase 8C (Siat8C) | | *Pan troglodytes* | n.d. | AJ697660 | **CAG26898.1** | | |
| α-2,8-sialyltransferase 8D (Siat8D) | | *Pan troglodytes* | n.d. | AJ697661 | **CAG26899.1** | | |
| α-2,8-sialyltransferase | | *Pan troglodytes* | n.d. | AJ697662 | **CAG26900.1** | | |

FIGURE 9I

| Protein | Organism | | EC# | GenBank / GenPept | | SwissProt | PDB / 3D |
|---|---|---|---|---|---|---|---|
| 8E (Siat8E) | | | | | | | |
| α-2,8-sialyltransferase 8F (Siat8F) | | *Pan troglodytes* | n.d. | AJ697663 | **CAG26901.1** | | |
| β-galactosamide α-2,6-sialyltransferase I (ST6Gal I; Siat1) | | *Pan troglodytes* | 2.4.99.1 | AJ627624 | **CAF29492.1** | | |
| β-galactosamide α-2,6-sialyltransferase II (ST6Gal II) | | *Pan troglodytes* | n.d. | AJ627625 | **CAF29493.1** | | |
| GM3 synthase ST3Gal V (Siat9) | | *Pan troglodytes* | n.d. | AJ744807 | **CAG32843.1** | | |
| S138L | | *Rabbit fibroma virus Kasza* | n.d. | NC_001266 | **NP_052025** | | |
| α-2,3-sialyltransferase ST3Gal III | | *Rattus norvegicus* | 2.4.99.6 | M97754<br>NM_031697 | AAA42146.1<br>NP_113885.1 | **Q02734** | |
| α-2,3-sialyltransferase ST3Gal IV (Siat4c) | | *Rattus norvegicus* | n.d. | AJ626825 | **CAF25183.1** | | |
| α-2,3-sialyltransferase ST3Gal VI | | *Rattus norvegicus* | n.d. | AJ626743 | **CAF25053.1** | | |
| α-2,6-sialyltransferase ST3Gal II | | *Rattus norvegicus* | 2.4.99.- | X76988<br>NM_031695 | CAA54293.1<br>NP_113883.1 | **Q11205** | |
| α-2,6-sialyltransferase ST6Gal I | | *Rattus norvegicus* | 2.4.99.1 | M18769<br>M83143 | AAA41196.1<br>AAB07233.1 | **P13721** | |
| α-2,6-sialyltransferase ST6GalNAc I (Siat7A) | | *Rattus norvegicus* | n.d. | AJ634458 | **CAG25684.1** | | |
| α-2,6-sialyltransferase ST6GalNAc II (Siat7B) | | *Rattus norvegicus* | n.d. | AJ634457 | **CAG25679.1** | | |
| α-2,6-sialyltransferase ST6GalNAc III | | *Rattus norvegicus* | 2.4.99.- | L29554<br>BC072501<br>NM_019123 | AAC42086.1<br>AAH72501.1<br>NP_061996.1 | **Q64686** | |
| α-2,6-sialyltransferase ST6GalNAc IV (Siat7D) (fragment) | | *Rattus norvegicus* | n.d. | AJ646871 | **CAG26700.1** | | |
| α-2,6-sialyltransferase ST6GalNAc V (Siat7E) | | *Rattus norvegicus* | n.d. | AJ646872 | **CAG26701.1** | | |
| α-2,6-sialyltransferase ST6GalNAc VI (Siat7F) (fragment) | | *Rattus norvegicus* | n.d. | AJ646881 | **CAG26710.1** | | |
| α-2,8-sialyltransferase (GD3 synthase) ST8Sia I | | *Rattus norvegicus* | 2.4.99.- | U53883<br>D45255 | AAC27541.1<br>BAA08213.1 | **P70554**<br>**P97713** | |
| α-2,8-sialyltransferase (SIAT8E) | | *Rattus norvegicus* | n.d. | AJ699422 | **CAG27884.1** | | |
| α-2,8-sialyltransferase (SIAT8F) | | *Rattus norvegicus* | n.d. | AJ699423 | **CAG27885.1** | | |
| α-2,8-sialyltransferase ST8Sia II | | *Rattus norvegicus* | 2.4.99.- | L13445<br>NM_057156 | AAA42147.1<br>NP_476497.1 | **Q07977**<br>**Q64688** | |
| α-2,8-sialyltransferase ST8Sia III | | *Rattus norvegicus* | 2.4.99.- | U55938<br>NM_013029 | AAB50061.1<br>NP_037161.1 | **P97877** | |
| α-2,8-sialyltransferase ST8Sia IV | | *Rattus norvegicus* | 2.4.99.- | U90215 | AAB49989.1 | **O08563** | |
| β-galactosamide α-2,6-sialyltransferase II (ST6Gal II) | | *Rattus norvegicus* | n.d. | AJ627626 | **CAF29494.1** | | |
| GM3 synthase ST3Gal V | | *Rattus norvegicus* | n.d. | AB018049<br>NM_031337 | BAA33492.1<br>NP_112627.1 | **O88830** | |

FIGURE 9J

| Protein | Organism | | EC# | GenBank / GenPept | | SwissProt | PDB / 3D |
|---|---|---|---|---|---|---|---|
| sialyltransferase ST3Gal-I (Siat4A) | | *Rattus norvegicus* | n.d. | AJ748840 | CAG44449.1 | | |
| α-2,3-sialyltransferase (St3Gal-II) | | *Silurana tropicalis* | n.d. | AJ585763 | CAE51387.1 | | |
| α-2,6-sialyltransferase (Siat7b) | | *Silurana tropicalis* | n.d. | AJ620650 | CAF05849.1 | | |
| α-2,6-sialyltransferase (St6galnac) | | *Strongylocentrotus purpuratus* | n.d. | AJ699425 | CAG27887.1 | | |
| α-2,3-sialyltransferase (ST3GAL-III) | | *Sus scrofa* | n.d. | AJ585765 | CAE51389.1 | | |
| α-2,3-sialyltransferase (ST3GAL-IV) | | *Sus scrofa* | n.d. | AJ584674 | CAE48299.1 | | |
| α-2,3-sialyltransferase ST3Gal I | | *Sus scrofa* | 2.4.99.4 | M97753 | AAA31125.1 | Q02745 | |
| α-2,6-sialyltransferase (fragment) ST6Gal I | | *Sus scrofa* | 2.4.99.1 | AF136746 | AAD33059.1 | Q9XSG8 | |
| β-galactosamide α-2,6-sialyltransferase (ST6GalNAc-V) | | *Sus scrofa* | n.d. | AJ620948 | CAF06585.2 | | |
| sialyltransferase (fragment) ST6Gal I | | *sus scrofa* | n.d. | AF041031 | AAC15633.1 | O62717 | |
| ST6GALNAC-V | | *Sus scrofa* | n.d. | AJ620948 | CAF06585.1 | | |
| α-2,3-sialyltransferase (Siat5-r) | | *Takifugu rubripes* | n.d. | AJ744805 | CAG32841.1 | | |
| α-2,3-sialyltransferase ST3Gal I (Siat4) | | *Takifugu rubripes* | n.d. | AJ626816 | CAF25174.1 | | |
| α-2,3-sialyltransferase ST3Gal II (Siat5) (fragment) | | *Takifugu rubripes* | n.d. | AJ626817 | CAF25175.1 | | |
| α-2,3-sialyltransferase ST3Gal III (Siat6) | | *Takifugu rubripes* | n.d. | AJ626818 | CAF25176.1 | | |
| α-2,6-sialyltransferase ST6Gal I (Siat1) | | *Takifugu rubripes* | n.d. | AJ744800 | CAG32836.1 | | |
| α-2,6-sialyltransferase ST6GalNAc II (Siat7B) | | *Takifugu rubripes* | n.d. | AJ634460 | CAG25681.1 | | |
| α-2,6-sialyltransferase ST6GalNAc II B (Siat7B-related) | | *Takifugu rubripes* | n.d. | AJ634461 | CAG25682.1 | | |
| α-2,6-sialyltransferase ST6GalNAc III (Siat7C) (fragment) | | *Takifugu rubripes* | n.d. | AJ634456 | CAG25678.1 | | |
| α-2,6-sialyltransferase ST6GalNAc IV (siat7D) (fragment) | | *Takifugu rubripes* | 2.4.99.3 | Y17466<br>AJ646869 | CAB44338.1<br>CAG26698.1 | Q9W6U6 | |
| α-2,6-sialyltransferase ST6GalNAc V (Siat7E) (fragment) | | *Takifugu rubripes* | n.d. | AJ646873 | CAG26702.1 | | |
| α-2,6-sialyltransferase ST6GalNAc VI (Siat7F) (fragment) | | *Takifugu rubripes* | n.d. | AJ646880 | CAG26709.1 | | |
| α-2,8-sialyltransferase ST8Sia I (Siat 8A) (fragment) | | *Takifugu.rubripes* | n.d. | AJ715534 | CAG29373.1 | | |
| α-2,8-sialyltransferase ST8Sia II (Siat 8B) (fragment) | | *Takifugu rubripes* | n.d. | AJ715538 | CAG29377.1 | | |
| α-2,8-sialyltransferase ST8Sia III (Siat 8C) (fragment) | | *Takifugu rubripes* | n.d. | AJ715541 | CAG29380.1 | | |
| α-2,8-sialyltransferase ST8Sia IIIr (Siat 8Cr) | | *Takifugu rubripes* | n.d. | AJ715542 | CAG29381.1 | | |
| α-2,8-sialyltransferase ST8Sia V (Siat 8E) | | *Takifugu rubripes* | n.d. | AJ715547 | CAG29386.1 | | |

FIGURE 9K

| Protein | Organism | | EC# | GenBank / GenPept | | SwissProt | PDB / 3D |
|---|---|---|---|---|---|---|---|
| (fragment) | | | | | | | |
| α-2,8-sialyltransferase ST8Sia VI (Siat 8F) (fragment) | | *Takifugu rubripes* | n.d. | AJ715549 | CAG29388.1 | | |
| α-2,8-sialyltransferase ST8Sia VIr (Siat 8Fr) | | *Takifugu rubripes* | n.d. | AJ715550 | CAG29389.1 | | |
| α-2,3-sialyltransferase (Siat5-r) | | *Tetraodon nigroviridis* | n.d. | AJ744806 | CAG32842.1 | | |
| α-2,3-sialyltransferase ST3Gal I (Siat4) | | *Tetraodon nigroviridis* | n.d. | AJ744802 | CAG32838.1 | | |
| α-2,3-sialyltransferase ST3Gal III (Siat6) | | *Tetraodon nigroviridis* | n.d. | AJ626822 | CAF25180.1 | | |
| α-2,6-sialyltransferase ST6GalNAc II (Siat7B) | | *Tetraodon nigroviridis* | n.d. | AJ634462 | CAG25683.1 | | |
| α-2,6-sialyltransferase ST6GalNAc V (Siat7E) (fragment) | | *Tetraodon nigroviridis* | n.d. | AJ646879 | CAG26708.1 | | |
| α-2,8-sialyltransferase ST8Sia I (Siat 8A) (fragment) | | *Tetraodon nigroviridis* | n.d. | AJ715536 | CAG29375.1 | | |
| α-2,8-sialyltransferase ST8Sia II (Siat 8B) (fragment) | | *Tetraodon nigroviridis* | n.d. | AJ715537 | CAG29376.1 | | |
| α-2,8-sialyltransferase ST8Sia III (Siat 8C) (fragment) | | *Tetraodon nigroviridis* | n.d. | AJ715539 | CAG29378.1 | | |
| α-2,8-sialyltransferase ST8Sia IIIr (Siat 8Cr) (fragment) | | *Tetraodon nigroviridis* | n.d. | AJ715540 | CAG29379.1 | | |
| α-2,8-sialyltransferase ST8Sia V (Siat 8E) (fragment) | | *Tetraodon nigroviridis* | n.d. | AJ715548 | CAG29387.1 | | |
| α-2,3-sialyltransferase (St3Gal-II) | | *Xenopus laevis* | n.d. | AJ585762 | CAE51386.1 | | |
| α-2,3-sialyltransferase (St3Gal-VI) | | *Xenopus laevis* | n.d. | AJ585766 | CAE51390.1 | | |
| α-2,3-sialyltransferase St3Gal-III (Siat6) | | *Xenopus laevis* | n.d. | AJ585764<br>AJ626823 | CAE51388.1<br>CAF25181.1 | | |
| α-2,8-polysialyltransferase | | *Xenopus laevis* | 2.4.99.- | AB007468 | BAA32617.1 | O93234 | |
| α-2,8-sialyltransferase ST8Siα-I (Siat8A;GD3 synthase) | | *Xenopus laevis* | n.d. | AY272056<br>AY272057<br>AJ704562 | AAQ16162.1<br>AAQ16163.1<br>CAG28695.1 | | |
| Unknown (protein for MGC:81265) | | *Xenopus laevis* | n.d. | BC068760 | AAH68760.1 | | |
| α-2,3-sialyltransferase (3Gal-VI) | | *Xenopus tropicalis* | n.d. | AJ626744 | CAF25054.1 | | |
| α-2,3-sialyltransferase (Siat4c) | | *Xenopus tropicalis* | n.d. | AJ622908 | CAF22058.1 | | |
| α-2,6-sialyltransferase ST6GalNAc V (Siat7E) (fragment) | | *Xenopus tropicalis* | n.d. | AJ646878 | CAG26707.1 | | |
| α-2,8-sialyltransferase ST8Sia III (Siat 8C) (fragment) | | *Xenopus tropicalis* | n.d. | AJ715544 | CAG29383.1 | | |
| β-galactosamide α-2,6-sialyltransferase II (ST6Gal II) | | *Xenopus tropicalis* | n.d. | AJ627628 | CAF29496.1 | | |
| sialytransferase St8SiaI | | *Xenopus tropicalis* | n.d. | AY652775 | AAT67042 | | |
| poly-α-2,8-sialosyl sialyltransferase (NeuS) | | *Escherichia coli K1* | 2.4.-.- | M76370<br>X60598 | AAA24213.1<br>CAA43053.1 | Q57269 | |
| polysialyltransferase | | *Escherichia coli K92* | 2.4.-.- | M88479 | AAA24215.1 | Q47404 | |

FIGURE 9L

| Protein | Organism | | EC# | GenBank / GenPept | | SwissProt | PDB / 3D |
|---|---|---|---|---|---|---|---|
| α-2,8 polysialyltransferase SiaD | | *Neisseria meningitidis B1940* | 2.4.-.- | M95053<br>X78068 | AAA20478.1<br>CAA54985.1 | **Q51281**<br>**Q51145** | |
| SynE | | *Neisseria meningitidis FAM18* | n.d. | U75650 | **AAB53842.1** | O06435 | |
| polysialyltransferase (SiaD)(fragment) | | *Neisseria meningitidis M1019* | n.d. | AY234192 | **AAO85290.1** | | |
| SiaD (fragment) | | *Neisseria meningitidis M209* | n.d. | AY281046 | **AAP34769.1** | | |
| SiaD (fragment) | | *Neisseria meningitidis M3045* | n.d. | AY281044 | **AAP34767.1** | | |
| polysialyltransferase (SiaD)(fragment) | | *Neisseria meningitidis M3315* | n.d. | AY234191 | **AAO85289.1** | | |
| SiaD (fragment) | | *Neisseria meningitidis M3515* | n.d. | AY281047 | **AAP34770.1** | | |
| polysialyltransferase (SiaD)(fragment) | | *Neisseria meningitidis M4211* | n.d. | AY234190 | **AAO85288.1** | | |
| SiaD (fragment) | | *Neisseria meningitidis M4642* | n.d. | AY281048 | **AAP34771.1** | | |
| polysialyltransferase (SiaD)(fragment) | | *Neisseria meningitidis M5177* | n.d. | AY234193 | **AAO85291.1** | | |
| SiaD | | *Neisseria meningitidis M5178* | n.d. | AY281043 | **AAP34766.1** | | |
| SiaD (fragment) | | *Neisseria meningitidis M980* | n.d. | AY281045 | **AAP34768.1** | | |
| NMB0067 | | *Neisseria meningitidis MC58* | n.d. | NC_003112 | **NP_273131** | | |
| Lst | | *Aeromonas punctata Sch3* | n.d. | AF126256 | **AAS66624.1** | | |
| ORF2 | | *Haemophilus influenzae A2* | n.d. | M94855 | **AAA24979.1** | | |
| HI1699 | | *Haemophilus influenzae Rd* | n.d. | U32842<br>NC_000907 | **AAC23345.1**<br>NP_439841.1 | Q48211 | |
| α-2,3-sialyltransferase | | *Neisseria gonorrhoeae F62* | 2.4.99.4 | U60664 | **AAC44539.1**<br>AAE67205.1 | P72074 | |
| α-2,3-sialyltransferase | | *Neisseria meningitidis 126E, NRCC 4010* | 2.4.99.4 | U60662 | **AAC44544.2** | | |
| α-2,3-sialyltransferase | | *Neisseria meningitidis 406Y, NRCC 4030* | 2.4.99.4 | U60661 | **AAC44543.1** | | |
| α-2,3-sialyltransferase (NMB0922) | | *Neisseria meningitidis MC58* | 2.4.99.4 | U60660<br>AE002443<br>NC_003112 | AAC44541.1<br>AAF41330.1<br>**NP_273962.1** | P72097 | |
| NMA1118 | | *Neisseria meningitidis Z2491* | n.d. | AL162755<br>NC_003116 | CAB84380.1<br>NP_283887.1 | **Q9JUV5** | |
| PM0508 | | *Pasteurella multocida PM70* | n.d. | AE006086<br>NC_002663 | **AAK02592.1**<br>NP_245445.1 | Q9CNC4 | |
| WaaH | | *Salmonella enterica SARB25* | n.d. | AF519787 | **AAM82550.1** | Q8KS93 | |
| WaaH | | *Salmonella enterica SARB3* | n.d. | AF519788 | **AAM82551.1** | Q8KS92 | |
| WaaH | | *Salmonella enterica SARB39* | n.d. | AF519789 | **AAM82552.1** | | |
| WaaH | | *Salmonella enterica SARB53* | n.d. | AF519790 | **AAM82553.1** | | |
| WaaH | | *Salmonella enterica SARB57* | n.d. | AF519791 | **AAM82554.1** | Q8KS91 | |
| WaaH | | *Salmonella enterica SARB71* | n.d. | AF519793 | **AAM82556.1** | Q8KS89 | |
| WaaH | | *Salmonella enterica* | n.d. | AF519792 | **AAM82555.1** | Q8KS90 | |

FIGURE 9M

| Protein | Organism | EC# | GenBank / GenPept | | SwissProt | PDB / 3D |
|---|---|---|---|---|---|---|
| | *SARB8* | | | | | |
| WaaH | *Salmonella enterica SARC10V* | n.d. | AF519779 | **AAM88840.1** | Q8KS99 | |
| WaaH (fragment) | *Salmonella enterica SARC12* | n.d. | AF519781 | **AAM88842.1** | | |
| WaaH (fragment) | *Salmonella enterica SARC13I* | n.d. | AF519782 | **AAM88843.1** | Q8KS98 | |
| WaaH (fragment) | *Salmonella enterica SARC14I* | n.d. | AF519783 | **AAM88844.1** | Q8KS97 | |
| WaaH | *Salmonella enterica SARC15II* | n.d. | AF519784 | **AAM88845.1** | Q8KS96 | |
| WaaH | *Salmonella enterica SARC16II* | n.d. | AF519785 | **AAM88846.1** | Q8KS95 | |
| WaaH (fragment) | *Salmonella enterica SARC3I* | n.d. | AF519772 | **AAM88834.1** | Q8KSA4 | |
| WaaH (fragment) | *Salmonella enterica SARC4I* | n.d. | AF519773 | **AAM88835.1** | Q8KSA3 | |
| WaaH | *Salmonella enterica SARC5IIa* | n.d. | AF519774 | **AAM88836.1** | | |
| WaaH | *Salmonella enterica SARC6IIa* | n.d. | AF519775 | **AAM88837.1** | Q8KSA2 | |
| WaaH | *Salmonella enterica SARC8* | n.d. | AF519777 | **AAM88838.1** | Q8KSA1 | |
| WaaH | *Salmonella enterica SARC9V* | n.d. | AF519778 | **AAM88839.1** | Q8KSA0 | |
| UDP-glucose : α-1,2-glucosyltransferase (WaaH) | *Salmonella enterica subsp. arizonae SARC 5* | 2.4.1.- | AF511116 | **AAM48166.1** | | |
| bifunctional α-2,3/-2,8-sialyltransferase (Cst-II) | *Campylobacter jejuni ATCC 43449* | n.d. | AF401529 | **AAL06004.1** | Q93CZ5 | |
| Cst | *Campylobacter jejuni 81-176* | n.d. | AF305571 | **AAL09368.1** | | |
| α-2,3-sialyltransferase (Cst-III) | *Campylobacter jejuni ATCC 43429* | 2.4.99.- | AY044156 | **AAK73183.1** | | |
| α-2,3-sialyltransferase (Cst-III) | *Campylobacter jejuni ATCC 43430* | 2.4.99.- | AF400047 | **AAK85419.1** | | |
| α-2,3-sialyltransferase (Cst-II) | *Campylobacter jejuni ATCC 43432* | 2.4.99.- | AF215659 | **AAG43979.1** | Q9F0M9 | |
| α-2,3/8-sialyltransferase (CstII) | *Campylobacter jejuni ATCC 43438* | n.d. | AF400048 | **AAK91725.1** | Q93MQ0 | |
| α-2,3-sialyltransferase cst-II | *Campylobacter jejuni ATCC 43446* | 2.4.99.- | AF167344 | **AAF34137.1** | | |
| α-2,3-sialyltransferase (Cst-II) | *Campylobacter jejuni ATCC 43456* | 2.4.99.- | AF401528 | **AAL05990.1** | Q93D05 | |
| α-2,3-/α-2,8-sialyltransferase (CstII) | *Campylobacter jejuni ATCC 43460* | 2.4.99.- | AY044868 | **AAK96001.1** | Q938X6 | |
| α-2,3/8-sialyltransferase (Cst-II) | *Campylobacter jejuni ATCC 700297* | n.d. | AF216647 | **AAL36462.1** | | |
| ORF | *Campylobacter jejuni GB11* | n.d. | AY422197 | **AAR82875.1** | | |
| α-2,3-sialyltransferase cstIII | *Campylobacter jejuni MSC57360* | 2.4.99.- | AF195055 | **AAG29922.1** | | |
| α-2,3-sialyltransferase cstIII Cj1140 | *Campylobacter jejuni NCTC 11168* | 2.4.99.- | AL139077<br>NC_002163 | **CAB73395.1**<br>NP_282288.1 | Q9PNF4 | |
| α-2,3/α-2,8-sialyltransferase II (cstII) | *Campylobacter jejuni O:10* | n.d. | -<br>AX934427 | AAO96669.1<br>**CAF04167.1** | | |
| α-2,3/α-2,8-sialyltransferase II (CstII) | *Campylobacter jejuni O:19* | n.d. | AX934431 | **CAF04169.1** | | |
| α-2,3/α-2,8-sialyltransferase II (CstII) | *Campylobacter jejuni O:36* | n.d. | AX934436 | **CAF04171.1** | | |
| α-2,3/α-2,8- | *Campylobacter* | n.d. | AX934434 | **CAF04170.1** | | |

FIGURE 9N

| Protein | Organism | | EC# | GenBank / GenPept | | SwissProt | PDB / 3D |
|---|---|---|---|---|---|---|---|
| sialyltransferase II (CstII) | | *jejuni O:4* | | | | | |
| α-2,3/α-2,8-sialyltransferase II (CstII) | | *Campylobacter jejuni O:41* | n.d. | -<br>-<br>AX934429 | AAO96670.1<br>AAT17967.1<br>**CAF04168.1** | | |
| α-2,3-sialyltransferase cst-I | | *Campylobacter jejuni OH4384* | 2.4.99.- | AF130466<br>- | **AAF13495.1**<br>AAS36261.1 | Q9RGF1 | |
| bifunctional α-2,3/-2,8-sialyltransferase (Cst-II) | | *Campylobacter jejuni OH4384* | 2.4.99.- | AF130984<br>AX934425 | **AAF31771.1**<br>CAF04166.1 | 1RO7<br>1RO8 | C<br>A |
| HI0352 (fragment) | | *Haemophilus influenzae Rd* | n.d. | U32720<br>X57315<br>NC_000907 | AAC22013.1<br>CAA40567.1<br>NP_438516.1 | **P24324** | |
| PM1174 | | *Pasteurella multocida PM70* | n.d. | AE006157<br>NC_002663 | **AAK03258.1**<br>NP_246111.1 | Q9CLP3 | |
| Sequence 10 from patent US 6503744 | | *Unknown.* | n.d. | - | **AAO96672.1** | | |
| Sequence 10 from patent US 6699705 | | *Unknown.* | n.d. | - | **AAT17969.1** | | |
| Sequence 12 from patent US 6699705 | | *Unknown.* | n.d. | - | **AAT17970.1** | | |
| Sequence 2 from patent US 6709834 | | *Unknown.* | n.d. | - | **AAT23232.1** | | |
| Sequence 3 from patent US 6503744 | | *Unknown.* | n.d. | - | **AAO96668.1** | | |
| Sequence 3 from patent US 6699705 | | *Unknown.* | n.d. | - | **AAT17965.1** | | |
| Sequence 34 from patent US 6503744 | | *Unknown.* | n.d. | - | **AAO96684.1** | | |
| Sequence 35 from patent US 6503744 (fragment) | | *Unknown.* | n.d. | -<br>- | **AAO96685.1**<br>AAS36262.1 | | |
| Sequence 48 from patent US 6699705 | | *Unknown.* | n.d. | - | **AAT17988.1** | | |
| Sequence 5 from patent US 6699705 | | *Unknown.* | n.d. | - | **AAT17966.1** | | |
| Sequence 9 from patent US 6503744 | | *Unknown.* | n.d. | - | **AAO96671.1** | | |

```
                              SEQUENCE LISTING


<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165


<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
```

-continued

```
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

GLYCOPEGYLATED ERYTHROPOIETIN

CROSS-REFERENCES TO RELATED APPLICATIONS

The present application is a continuation-in-part of U.S. patent application Ser. No. 10/997,405, filed Nov. 24, 2004, the contents of which is incorporated herein by reference in its entirety for all purposes; the present application also claims the benefit under 35 USC 119(e) of U.S. Provisional Patent Application No. 60/685,007 filed May 25, 2005; U.S. patent application Ser. No. 10/997,405, filed Nov. 24, 2004 claims the benefit under 35 USC 119(e) of U.S. Provisional Patent Application No. 60/623,387, filed Oct. 29, 2004; U.S. Provisional Patent Application No. 60/614,518, filed Sep. 29, 2004; U.S. Provisional Patent Application No. 60/592,744, filed Jul. 29, 2004; U.S. Provisional Patent Application No. 60/590,573, filed Jul. 23, 2004; U.S. Provisional Patent Application No. 60/555,504, filed Mar. 22, 2004; U.S. Provisional Patent Application No. 60/539,387, filed Jan. 26, 2004; and U.S. Provisional Patent Application No. 60/524,989, filed Nov. 24, 2003.

BACKGROUND OF THE INVENTION

Erythropoietin (EPO) is a cytokine produced by the kidney and liver which acts on hematopoietic stem cells to stimulate the production of red blood cells. The protein exists in two forms: one is a 165 amino acid peptide, and the other is a 166 amino acid peptide. The 166 amino acid peptide has the same sequence as the 165 amino acid with an additional arginine in the most C-terminal position. The mature 165 amino acid peptide is a 34 kD glycoprotein comprising three N-glycosylation sites (Asn-24, Asn-38, and Asn-83), and 1 O-glycosylation site (Ser-126). Some variants are "hyperglycosylated" comprising 5 N-linked glycosylation sites.

Erythropoietin synthesis is induced by conditions that effectively create tissue hypoxia, such as lowering of the arterial $O_2$ tension or increasing the oxygen affinity of the blood. Under usual conditions of homeostasis, hematocrit and the concentration of hemoglobin in blood are maintained constant with erythropoiesis counterbalancing the permanent destruction of aged red blood cells by macrophages in bone marrow, spleen and liver. Quantitatively, about 1% of the red cell mass, which is about $2\text{-}3\times10^{11}$ red blood cells, is renewed each day. However, in situations that effectively generate tissue hypoxia, such as blood loss or location to high altitudes, the induction of EPO may stimulate erythropoiesis 10-fold or more over normal levels.

Because EPO stimulates red blood cell production it is an effective therapy for many diseases and conditions associated with reduced hematocrit. Initial trials of replacement therapy with recombinant human EPO to restore the hematocrit in patients with end-stage renal failure were first reported about 20 years ago (see e.g., Winearls, C. G.; et al. (1986) *Lancet,* 2, 1175-1178, and Eschbach, J. W.; et al. (1987) *N. Engl. J. Med.,* 316, 73-78). This work provided an impetus for further studies into the pathophysiology and pharmacology of EPO (see e.g., Jelkmann, W. and Gross, A. (1989) Erythropoietin; Springer, Berlin Heidelberg New York).

Since those early studies, recombinant human EPO has been used successfully to treat numerous pathological conditions. For example, the pharmacological application of recombinant human EPO to surgical patients can lower the severity and duration of postoperative anemia. The administration of recombinant human EPO has also proven to be effective therapy for patients suffering from several non-renal diseases, such as chronic inflammation, malignancy and AIDS, wherein a relative lack of endogenous EPO contributes to the development of anemia (see e.g., Means, R. T. and Krantz, S. B. (1992) *Blood,* 80, 1639-1647, and Jelkmann, W. (1998) *J. Interf. Cytokine Res.,* 18, 555-559). Furthermore, it has been reported that EPO is tissue protective in ischemic, traumatic, toxic and inflammatory injuries (see e.g., Brines M., et al. (2004) *Proc. Natl. Acad. Sci. USA* 101, 14907-14912 and Brines, M. L., et al. (2000). *Proc. Natl. Acad. Sci. USA* 97, 10526-10531).

The usefulness and effectiveness of EPO for the treatment of anemias and other conditions arising from such a wide variety of causes makes recombinant human EPO perhaps the best selling drug in the world. Indeed, estimated sales amount to more than 5 billion US dollars per year.

Recombinant human EPO, produced in Chinese Hamster Ovary (CHO) cell line, is used extensively as a therapeutic. Since mammals all produce glycans of similar structure, Chinese Hamster Ovary (CHO), Baby Hamster Kidney (BHK), and Human Embryonic Kidney-293 (HEK-293) are the preferred host cells for production of glycoprotein therapeutics. As is known in the art, proper glycosylation is a critically important factor influencing the in vivo the half life and immunogenicity of therapeutic peptides. Poorly glycosylated proteins are recognized by the liver as being "old" and thus, are more quickly eliminated from the body than are properly glycosylated proteins.

Another phenomena that hampers the use of therapeutic peptides is the relatively short in vivo half life exhibited by these peptides. Overall, the problem of short in vivo half life means that therapeutic glycopeptides must be administered frequently in high dosages, which ultimately translate to higher health care costs than might be necessary if a more efficient method for making longer lasting, more effective glycoprotein therapeutics was available.

One solution to the problem of providing cost effective glycopeptide therapeutics is increasing the in vivo half life of the peptide. For example, glycopeptide therapeutics with improved pharmacokinetic properties are produced by attaching synthetic polymers to the peptide backbone. An exemplary polymer that has been conjugated to peptides is poly(ethylene glycol) ("PEG"). The use of PEG to derivatize peptide therapeutics has been demonstrated to reduce the immunogenicity of the peptides. For example, U.S. Pat. No. 4,179,337 (Davis et al.) discloses non-immunogenic polypeptides such as enzymes and peptide hormones coupled to polyethylene glycol (PEG) or polypropylene glycol. In addition to reduced immunogenicity, the clearance time in circulation is prolonged due to the increased size of the PEG-conjugate of the polypeptides in question.

The principal mode of attachment of PEG, and its derivatives, to peptides is a non-specific covalent bonding through a peptide amino acid residue (see e.g., U.S. Pat. No. 4,088,538 U.S. Pat. No. 4,496,689, U.S. Pat. No. 4,414,147, U.S. Pat. No. 4,055,635, and PCT WO 87/00056). Another mode of attaching PEG to peptides is through the non-specific oxidation of glycosyl residues on a glycopeptide (see e.g., WO 94/05332), which is followed by the reductive amination of the resulting carbonyl moiety with an amino-PEG species.

In these non-specific methods, poly(ethylene glycol) is added in a random, non-specific manner to reactive residues on a peptide backbone. Random attachment of PEG molecules has drawbacks, including a lack of homogeneity of the final product, and the possibility for reduction in the biological or enzymatic activity of the peptide. Therefore, for the production of therapeutic peptides, a derivitization strategy that results in the formation of a specifically labeled, readily characterizable, essentially homogeneous PEGylated peptide is superior. As set forth herein, such methods have been developed.

Specifically labeled, homogeneous peptide therapeutics can be produced in vitro through the action of enzymes. Unlike the typical non-specific methods for attaching a synthetic polymer or other label to a peptide, enzyme-based syntheses have the advantages of regioselectivity and stereoselectivity. Two principal classes of enzymes for use in the synthesis of labeled peptides are glycosyltransferases (e.g., sialyltransferases, oligosaccharyltransferases, N-acetylglucosaminyltransferases), and glycosidases. These enzymes can be used for the specific attachment of sugars which can be subsequently modified to comprise a therapeutic moiety. Alternatively, glycosyltransferases and modified glycosidases can be used to directly transfer modified sugars to a peptide backbone (see e.g., U.S. Pat. No. 6,399,336, and U.S. Patent Application Publications 20030040037, 20040132640, 20040137557, 20040126838, and 20040142856, each of which are incorporated by reference herein). Methods combining both chemical and enzymatic synthetic elements are also known (see e.g., Yamamoto et al. *Carbohydr. Res.* 305: 415-422 (1998) and U.S. Patent Application Publication 20040137557 which is incorporated herein by reference).

As discussed above, erythropoietin (EPO) is an extremely valuable therapeutic peptide. Although commercially available forms of EPO are in use today, these peptides are less than maximally effective due factors including microheterogeneity of the glycoprotein product which increases production costs, poor pharmacokinetics of the resulting isolated glycoprotein product, or a combination of the two. Thus, there remains a need in the art for long lasting EPO peptides with improved effectiveness and better pharmacokinetics. Furthermore, to be effective for the largest number of individuals, it must be possible to produce, on an industrial scale, an EPO peptide with improved therapeutic pharmacokinetics that has a predictable, essentially homogeneous, structure which can be readily reproduced over, and over again.

Fortunately, EPO peptides with improved therapeutic effectiveness and methods for making them have now been discovered. The present invention provides EPO peptides with improved pharmacokinetics. The invention also provides industrially practical and cost effective methods for the production of modified EPO peptides. The EPO peptides of the invention comprise modifying groups such as PEG moieties, therapeutic moieties, biomolecules and the like. The present invention therefore fulfills the need for EPO peptides with improved the therapeutic effectiveness and improved pharmacokinetics for the treatment of conditions and diseases wherein EPO provides effective therapy.

SUMMARY OF THE INVENTION

It has now been discovered that the controlled modification of erythropoietin (EPO) with one or more polymeric modifying moiety, e.g., poly(ethylene glycol), affords novel EPO derivatives with improved pharmacokinetic properties. Furthermore, cost effective methods for reliable and reproducible production of the polymer-modified EPO peptides of the invention have been discovered and developed.

The polymeric modifying moiety can be attached at any position of a glycosyl moiety of EPO. Moreover, the polymeric modifying moiety can be bound to a glycosyl residue at any position in the amino acid sequence of a wild type or mutant EPO peptide.

In an exemplary embodiment, the invention provides an EPO peptide that is conjugated through a glycosyl linking group to a polymeric modifying moiety. Exemplary EPO peptide conjugates include a glycosyl linking group having a formula selected from:

I

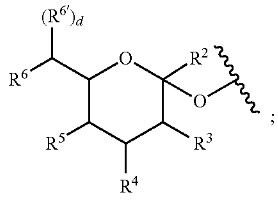

; and

II

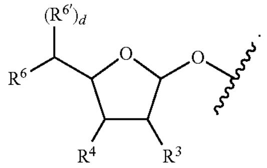

In Formulae I and II, $R^2$ is H, $CH_2OR^7$, $COOR^7$ or $OR^7$, in which $R^7$ represents H, substituted or unsubstituted alkyl or substituted or unsubstituted heteroalkyl. The symbols $R^3$, $R^4$, $R^5$, $R^6$ and $R^6$ independently represent H, substituted or unsubstituted alkyl, $OR^8$, $NHC(O)R^9$. The index d is 0 or 1. $R^8$ and $R^9$ are independently selected from H, substituted or unsubstituted alkyl, substituted or unsubstituted heteroalkyl or sialic acid. At least one of $R^3$, $R^4$, $R^5$, $R^6$ or $R^{6'}$ includes the polymeric modifying moiety e.g., PEG. In an exemplary embodiment, $R^6$ and $R^{6'}$, together with the carbon to which they are attached are components of the side chain of sialic acid. In a further exemplary embodiment, this side chain is functionalized with the polymeric modifying moiety.

In an exemplary embodiment, the polymeric moiety is bound to the glycosyl linking group, generally through a heteroatom on the glycosyl core (e.g., N, O), through a linker, L, as shown below:

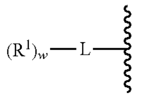

$R^1$ is the polymeric modifying moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety. Another exemplary linking group is an amino acid residue (e.g., cysteine, serine, lysine, and short oligopeptides, e.g., Lys-Lys, Lys-Lys-Lys, Cys-Lys, Ser-Lys, etc.)

When L is a bond, it is formed by reaction of a reactive functional group on a precursor of $R^1$ and a reactive functional group of complementary reactivity on a precursor of the glycosyl linking group. When L is a non-zero order linking group, L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling of the precursors proceeds by chemistry that is well understood in the art.

In an exemplary embodiment L is a linking group that is formed from an amino acid, or small peptide (e.g., 1-4 amino acid residues) providing a modified sugar in which the polymeric modifying moiety is attached through a substituted alkyl linker. Exemplary linkers include glycine, lysine, serine and cysteine. Amino acid analogs, as defined herein, are also of use as linker components. The amino acid may be modified with an additional component of a linker, e.g., alkyl, heteroalkyl, covalently attached through an acyl linkage, for example, an amide or urethane formed through an amine moiety of the amino acid residue.

In an exemplary embodiment, the glycosyl linker has a structure according to Formula I and $R^5$ includes the polymeric modifying moiety. In another exemplary embodiment, $R^5$ includes both the polymeric modifying moiety and a linker, L, joining the modifying moiety to the glycosyl core. L can be a linear or branched structure. Similarly, the polymeric modifying can be branched or linear.

The polymeric modifying moiety comprises two or more repeating units that can be water-soluble or essentially insoluble in water. Exemplary water-soluble polymers of use in the compounds of the invention include PEG, e.g., m-PEG, PPG, e.g., m-PPG, polysialic acid, polyglutamate, polyaspartate, polylysine, polyethyeleneimine, biodegradable polymers (e.g., polylactide, polyglyceride), and functionalized PEG, e.g., terminal-functionalized PEG.

The glycosyl core of the glycosyl linking groups of use in the EPO conjugates of the invention is selected from both natural and unnatural furanoses and pyranoses. The unnatural saccharides optionally include an alkylated or acylated hydroxyl and/or amine moiety, e.g., ethers, esters and amide substituents on the ring. Other unnatural saccharides include an H, hydroxyl, ether, ester or amide substituent at a position on the ring at which such a substituent is not present in the natural saccharide. Alternatively, the carbohydrate is missing a substituent that would be found in the carbohydrate from which its name is derived, e.g., deoxy sugars. Still further exemplary unnatural sugars include both oxidized (e.g., -onic and -uronic acids) and reduced (sugar alcohols) carbohydrates. The sugar moiety can be a mono-, oligo- or polysaccharide.

Exemplary natural sugars of use as components of glycosyl linking groups in the present invention include glucose, glucosamine, galactose, galactosamine, fucose, mannose, mannosamine, xylanose, ribose, N-acetyl glucose, N-acetyl glucosamine, N-acetyl galactose, N-acetyl galactosamine, and sialic acid.

In one embodiment, the present invention provides an erythropoietin peptide comprising the moiety:

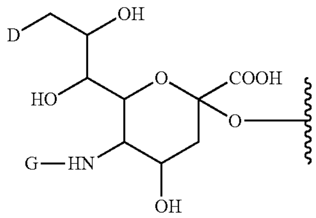

wherein D is a member selected from —OH and $R^1$-L-HN—; G is a member selected from H and $R^1$-L- and —C(O)($C_1$-$C_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is $R^1$-L-, and when G is —C(O)($C_1$-$C_6$)alkyl, D is $R^1$-L-NH—.

In another aspect, the invention provides a peptide comprising a glycosyl linking group having the formula:

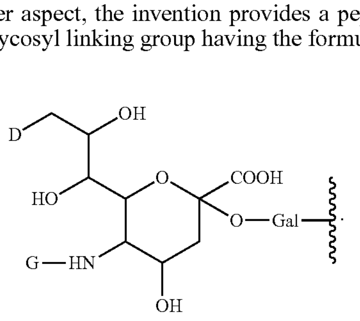

In other embodiments, the group has the formula:

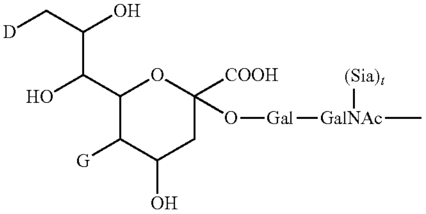

in which t is 0 or 1.

In yet another embodiment, the group has the formula:

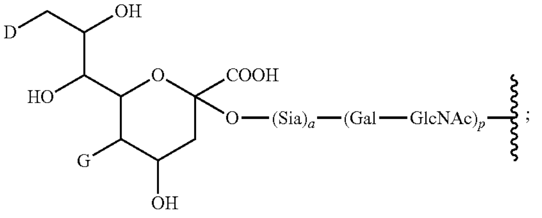

in which the index p represents and integer from 1 to 10, and a represents 0 or 1.

In another aspect, the invention provides a method of making a PEGylated erythropoietin of the invention. The method includes: (a) contacting a substrate erythropoietin peptide comprising a glycosyl group selected from:

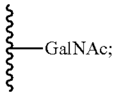

and

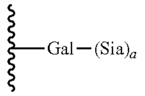

with a PEG-sialic acid donor having the formula:

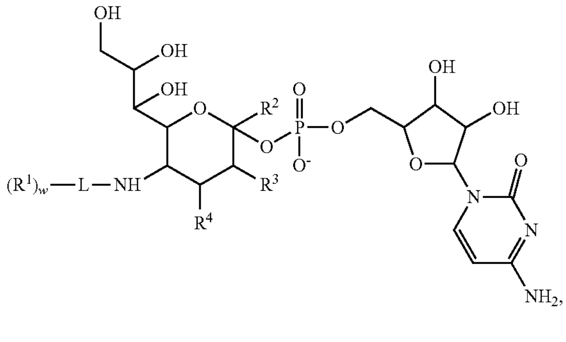

and an enzyme that transfers PEG-sialic acid from said donor onto a member selected from the Gal and the Sia of said glycosyl group, under conditions appropriate for said transfer. An exemplary modified sialic acid donor is CMP-sialic acid modified, through a linker moiety, with a polymer, e.g., a straight chain or branched poly(ethylene glycol) moiety.

The peptide can be acquired from essentially any source, however, in one embodiment, prior to being modified as discussed above, the erythropoietin peptide is expressed in a suitable host. Mammalian (e.g., CHO) and insect cells (e.g., Sf-9) are exemplary expression systems providing EPO of use in the compositions and methods set forth herein.

In another aspect, the invention provides a method of treating a condition in a subject in need thereof. Exemplary conditions include those characterized by compromised red blood cell production in the subject. The method includes the step of administering to the subject an amount of the polymer-modified erythropoietin peptide of the invention effective to ameliorate the condition in the subject.

In another aspect, the invention provides a method of enhancing red blood cell production in a mammal. The method includes administering to the mammal an amount of the polymer-modified erythropoietin peptide of the invention effective to enhance red blood cell production in the mammal.

In another aspect, the invention provides a method of treating a tissue injury in a subject in need thereof. Exemplary injuries include those characterized by damage resulting from ischemia, trauma, inflammation or contact with toxic substances. The method includes the step of administering to the subject an amount of a polymer-modified erythropoietin peptide of the invention effective to ameliorate the tissue injury in the subject. An exemplary class of protection or treatment includes neuroprotection (e.g., treatment of stroke, Alzheimer's, Parkinson's and other degenerative neurological disorders). The modified EPO of the invention is also of use in treating patients with diseases such as compromised kidney function, cancer, and retinopathy.

In another aspect, the invention provides a pharmaceutical formulation comprising a polymer-modified erythropoietin peptide of the invention and a pharmaceutically acceptable carrier.

In the polymer-modified erythropoietin glycoconjugates of the invention, essentially each of the amino acid residues to which the polymer is bound has the same structure across the population individual peptide molecules. For example, if one peptide molecule includes a Ser linked glycosyl residue that includes a glycosyl linking group attached to a polymeric modifying moiety, at least about 70%, 80%, 90%, 95%, 97%, 99%, 99.2%, 99.4%, 99.6%, or more preferably 99.8% of the other peptides in the population will have the same glycosyl residue with the polymeric modifying moiety covalently bound to the same Ser residue.

Other objects and advantages of the invention will be apparent to those of skill in the art from the detailed description that follows.

DESCRIPTION OF THE DRAWINGS

FIG. 2 is a representation of exemplary glycoPEGylated EPO isoforms isolated from Chinese Hamster Ovary cells. A. An exemplary O- or N-linked PEGylated glycoform. B. Is a representation of exemplary EPO isoforms isolated from insect cells and remodeled and glycoPEGylated.

FIG. 9 is a table displaying sialyltransferases of use to glycoPEGylate peptides with a modified sialic acid.

DETAILED DESCRIPTION OF THE INVENTION AND THE PREFERRED EMBODIMENTS

Abbreviations

Figure 1A:
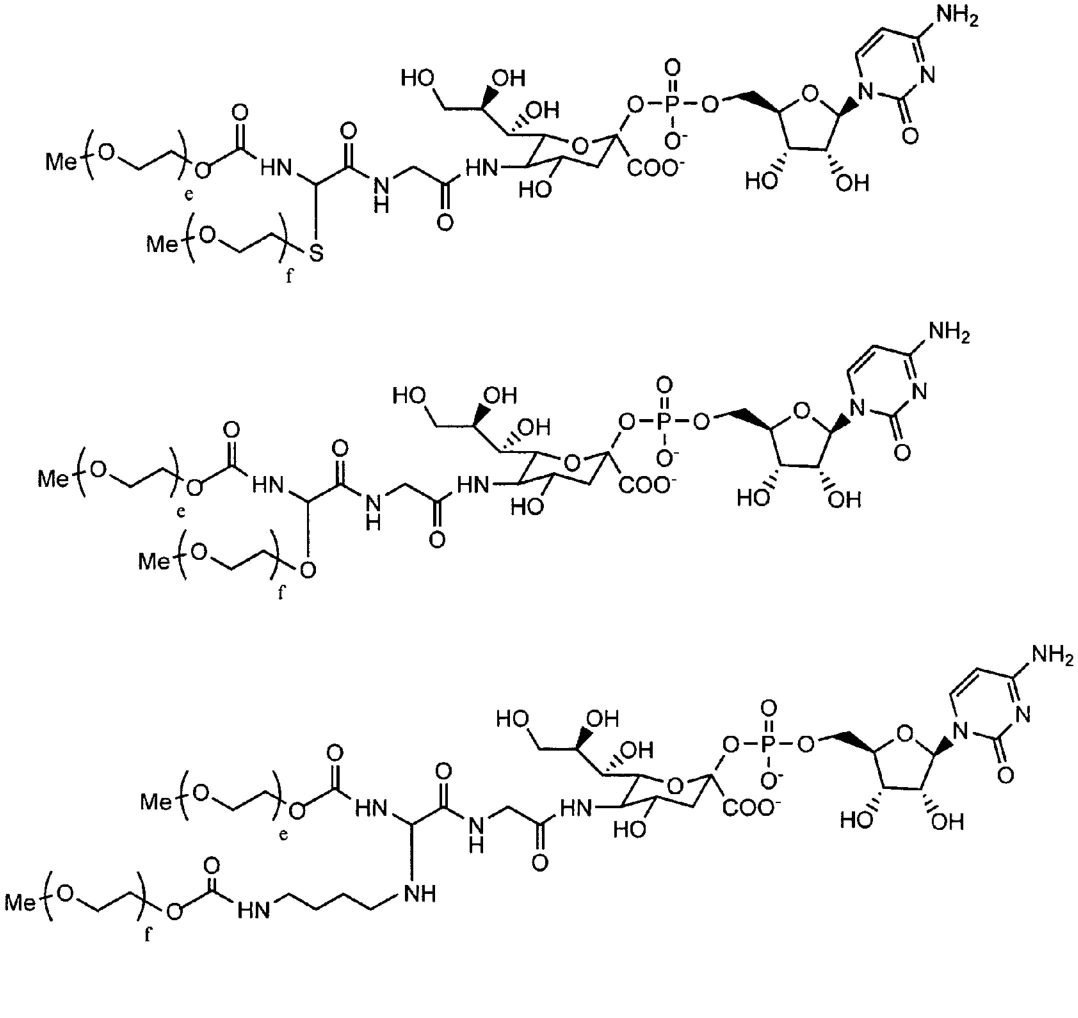
FIG. 1 illustrates exemplary modified sialic acid nucleotides useful in the practice of the invention. A. Structure of exemplary branched (e.g., 30 kDa, 40 kDa) CMP-sialic acid-PEG sugar nucleotides. B. Structure of linear CMP-sialic acid-PEG (e.g., 10 kDa).
Figure 1B:
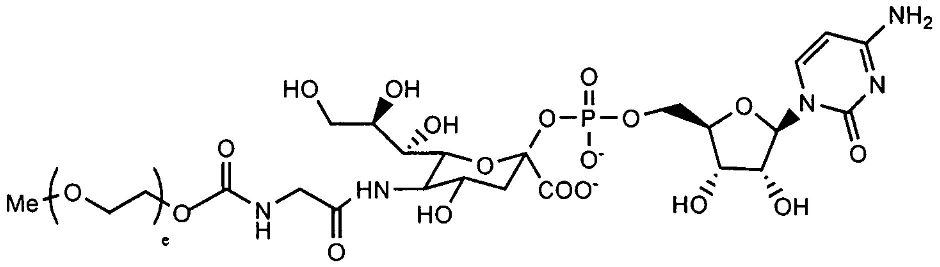

PEG, poly(ethylene glycol); PPG, poly(propylene glycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; NeuAc (N-acetylneuraminyl), Sia (sialyl); M6P, mannose-6-phosphate.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature, see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is conjugated with a modified sugar as set forth herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, the term "modified sugar," refers to a naturally- or non-naturally-occurring carbohydrate that is enzymatically added onto an amino acid or a glycosyl residue of a peptide in a process of the invention. The modified sugar is selected from enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, PEG moieties, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol). Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as $R(\text{-PEG-OH})_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius<2 nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives may vary depending upon the size, state of glycosylation, and other parameters, as is well known in the art. Further explanation of "half-life" is found in Pharmaceutical Biotechnology (1997, D F A Crommelin and R D Sindelar, eds., Harwood Publishers, Amsterdam, pp 101-120).

The term "glycoconjugation," as used herein, refers to the enzymatically mediated conjugation of a modified sugar species to an amino acid or glycosyl residue of a polypeptide, e.g., an Erythropoietin peptide of the present invention. A subgenus of "glycoconjugation" is "glyco-PEGylation," in which the modifying group of the modified sugar is poly (ethylene glycol), and alkyl derivative (e.g., m-PEG) or reactive derivative (e.g., $H_2N$-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g, multivalent agents. Therapeutic moiety also includes proteins and constructs that include proteins. Exemplary proteins include, but are not limited to, Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any grammatically equivalent term means the amount that, when administered to an animal for treating a disease, is sufficient to effect treatment for that disease.

The term "tissue protective" refers to the defense of a tissue against the effects of cellular damage that are typically associated with the experience by a tissue or organ of ischemia/hypoxia, trauma, toxicity and/or inflammation. Cellular damage may lead to apoptosis and/or necrosis (i.e., toxic cell death). Thus, a "tissue protective" effect guards a tissue from experiencing the degree of apoptosis and/or toxic cell death normally associated with a given traumatic, inflammatory, toxic or ischemic injury. For example, EPO reduces the area of infarct after middle cerebral artery occlusion in a rodent model (Siren, A. L. et al. (2001). *Proc. Natl. Acad. Sci. U.S.A.* 98, 4044-4049). Thus, under such conditions EPO provides a "tissue protective" effect by effectively reducing the necrosis and/or apoptosis normally associated with the ischemic injury (e.g., ischemic stroke). "Tissue protective" also refers to the defense of a tissue against the effects of cellular damage and the ensuing cell death associated with degenerative diseases such as retinopathy, or neurodegenerative disease.

The term "isolated" refers to a material that is substantially or essentially free from components, which are used to produce the material. For peptide conjugates of the invention, the term "isolated" refers to material that is substantially or essentially free from components which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. In the fucosylated structures set forth herein, the Fuc-GlcNAc linkage is generally α1,6 or α1,3, with α1,6 generally preferred. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —$NO_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R" R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_u$—U—, wherein T and U are independently —NR—, —O—, —CRR'— or a single bond, and u is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_z$—X—(CR"R"')$_d$—, where z and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

Introduction

Erythropoietin (EPO) is a glycoprotein which serves as the principal regulator of red blood cell synthesis. Erythropoietin acts by stimulating precursor cells in the bone marrow causing them to divide and differentiate into mature red blood cells. EPO may exist as either a 165 or 166 amino acid glycoprotein. The 166 amino acid variant is distinguished from the 165 amino acid variant by the presence of an additional arginine residue at the C-terminal end of the protein.

Recombinant EPO has been available for some time and is an effective therapeutic agent in the treatment of various forms of anemia, including anemias associated with chronic renal failure, zidovidine treated HIV infected patients, and cancer patients on chemotherapy. The glycoprotein is administered parenterally, either as an intravenous (IV) or subcutaneous (SC) injection.

To improve the effectiveness of recombinant erythropoietin used for therapeutic purposes, the present invention provides polymer conjugates of glycosylated and unglycosylated erythropoietin peptides. The conjugates may be additionally modified by further conjugation with diverse species such as therapeutic moieties, diagnostic moieties, targeting moieties and the like.

The conjugates of the invention are formed by the enzymatic attachment of a modified sugar bearing the polymeric modifying moiety to the glycosylated or unglycosylated peptide. Glycosylation sites provide loci for conjugating polymeric and other modifying groups to the peptide, e.g., by glycoconjugation. An exemplary modifying group is a water-soluble polymer, such as poly(ethylene glycol), e.g., methoxy-poly(ethylene glycol). Modification of the EPO peptides can improve the stability and retention time of the recombinant EPO in a patient's circulation and/or reduce the antigenicity of recombinant EPO.

The invention provides EPO peptides and glycopeptides that have a substantially homogeneous derivatization pattern. The invention also provides methods of preparing such peptides. The enzymes used in the methods of the invention are generally selective for a particular amino acid residue, combination of amino acid residues, or particular glycosyl residues of the peptide. The methods are also practical for large-scale production of modified peptides and glycopeptides. Thus, the methods of the invention provide a practical means for large-scale preparation of glycopeptides having preselected uniform derivatization patterns.

The present invention also provides conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

The Conjugates

In a first aspect, the present invention provides a conjugate between a selected modifying group and an EPO peptide. The link between the peptide and the modifying moiety includes a glycosyl linking group interposed between the peptide and the selected moiety. As discussed herein, the selected modifying moiety is essentially any species that can be attached to a saccharide unit, resulting in a "modified sugar" that is recognized by an appropriate transferase enzyme, which appends the modified sugar onto the peptide, or a glycosyl residue attached thereto. The saccharide component of the modified sugar, when interposed between the peptide and a selected moiety, becomes a "glycosyl linking group," e.g., an "intact glycosyl linking group." The glycosyl linking group is formed from any mono- or oligo-saccharide that, after modification with the modifying group, is a substrate for an enzyme that adds the modified sugar to an amino acid or glycosyl residue of a peptide.

The glycosyl linking group can be, or can include, a saccharide moiety that is degradatively modified before or during the addition of the modifying group. For example, the glycosyl linking group can be derived from a saccharide residue that is produced by oxidative degradation of an intact saccharide to the corresponding aldehyde, e.g., via the action of metaperiodate, and subsequently converted to a Schiff base with an appropriate amine, which is then reduced to the corresponding amine.

The conjugates of the invention will typically correspond to the general structure:

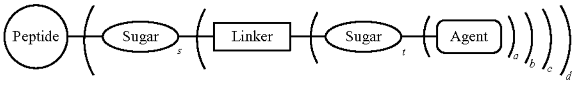

in which the symbols a, b, c, d and s represent a positive, non-zero integer; and t is either 0 or a positive integer. The "agent" is a therapeutic agent, a bioactive agent, a detectable label, water-soluble moiety (e.g., PEG, m-PEG, PPG, and m-PPG) or the like. The "agent" can be a peptide, e.g., enzyme, antibody, antigen, etc. The linker can be any of a wide array of linking groups, infra. Alternatively, the linker may be a single bond or a "zero order linker."

In an exemplary embodiment, the selected modifying group is a water-soluble polymer, e.g., m-PEG. The water-soluble polymer is covalently attached to the peptide via a glycosyl linking group. The glycosyl linking group is covalently attached to an amino acid residue or a glycosyl residue of the peptide. The invention also provides conjugates in which an amino acid residue and a glycosyl residue are modified with a glycosyl linking group.

An exemplary water-soluble polymer is poly(ethylene glycol), e.g., methoxy-poly(ethylene glycol). The poly(ethylene glycol) used in the present invention is not restricted to any particular form or molecular weight range. For unbranched poly(ethylene glycol) molecules the molecular weight is preferably between 500 and 100,000. A molecular weight of 2000-60,000 is preferably used and preferably of from about 5,000 to about 30,000.

In another embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is less than or equal to 40,000 daltons.

In addition to providing conjugates that are formed through an enzymatically added glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to a structurally identical amino acid or glycosyl residue. Thus, in a second aspect, the invention provides a peptide conjugate having a population of water-soluble polymer moieties, which are covalently bound to the peptide through a glycosyl linking group, e.g., an intact glycosyl linking group. In a preferred conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently bound thereto through a glycosyl linking group. In a preferred embodiment, essentially every member of the population of water soluble polymer moieties is bound to an amino acid residue of the peptide via a glycosyl linking group, and each amino acid residue having a glycosyl linking group attached thereto has the same structure.

The present invention also provides conjugates analogous to those described above in which the peptide is conjugated to a therapeutic moiety, diagnostic moiety, targeting moiety, toxin moiety or the like via an intact glycosyl linking group. Each of the above-recited moieties can be a small molecule, natural polymer (e.g., polypeptide) or synthetic polymer. When the modifying moiety is attached to a sialic acid, it is generally preferred that the modifying moiety is substantially non-fluorescent.

Essentially any erythropoietin peptide having any sequence is of use as a component of the conjugates of the present invention. In an exemplary embodiment, the peptide has the sequence:

(SEQ ID NO: 1)

$H_2N$-APPRLICDSR VLERYLLEAK EAENITTGCA EHCSLNENIT

VPDTKVNFYA WKRMEVGQQA VEVWQGLALL SEAVLRGQAL

LVNSSQPWEP LQLHVDKAVS GLRSLTTLLR ALGAQKEAIS

PPDAASAAPL RTITADTFRK LFRVYSNFLR GKLKLYTGEA

CRTGD-COOH.

In another exemplary embodiment the peptide has the sequence:

(SEQ ID NO: 2)

$H_2N$-APPRLICDSR VLERYLLEAK EAENITTGCA EHCSLNENIT

VPDTKVNFYA WKRMEVGQQA VEVWQGLALL SEAVLRGQAL

LVNSSQPWEP LQLHVDKAVS GLRSLTTLLR ALGAQKEAIS

-continued

PPDAASAAPL RTITADTFRK LFRVYSNFLR GKLKLYTGEA

CRTGDR-COOH.

Preferably, neither the amino nor the carboxy terminus of the EPO peptide is derivatized with a polymeric modifying moiety.

The peptides of the invention include at least one N-linked or O-linked glycosylation site, which is glycosylated with a glycosyl residue that includes a polymeric modifying moiety, e.g., a PEG moiety. In an exemplary embodiment, the PEG is covalently attached to the peptide via an intact glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which a glycosyl linking group is attached to both an amino acid residue and a glycosyl residue.

The PEG moiety is attached to an intact glycosyl linker directly, or via a non-glycosyl linker, e.g., substituted or unsubstituted alkyl, substituted or unsubstituted heteroalkyl.

In an exemplary embodiment, the invention utilizes a modified sugar amine that has the formula:

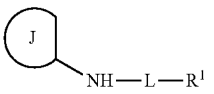

in which J is a glycosyl moiety (e.g., a nucleotide sugar), L is a bond or a linker and $R^1$ is the modifying group, e.g., a polymeric modifying moiety. Exemplary bonds are those that are formed between an $NH_2$ moiety on the glycosyl moiety and a group of complementary reactivity on the modifying group. For example, when $R^1$ includes a carboxylic acid moiety, this moiety may be activated and coupled with the $NH_2$ moiety on the glycosyl residue affording a bond having the structure $NHC(O)R^1$. J is preferably a glycosyl moiety that is "intact", not having been degraded by exposure to conditions that cleave the pyranose or furanose structure, e.g. oxidative conditions, e.g., sodium periodate.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the species of the invention, e.g., between the glycosyl moiety and the linker (L), or between the linker and the modifying group ($R^1$). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

Another exemplary linker is a PEG moiety, e.g., a PEG moiety that is functionalized with an amino acid residue. The PEG linker is conjugated to the glycosyl group through the amino acid residue at one PEG terminus and bound to $R^1$ through the other PEG terminus. Alternatively, the amino acid residue is bound to $R^1$ and the PEG terminus, which is not bound to the amino acid, is bound to the glycosyl group.

An exemplary species of NH-L-$R^1$ has the formula: $—NH\{C(O)(CH_2)_aNH\}_s\{C(O)(CH_2)_b(OCH_2CH_2)_cO(CH_2)_d NH\}_tR^1$, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —$CH_2$. As those of skill will appreciate one or more of the bracketed moieties corresponding to indices s and t can be replaced with a substituted or unsubstituted alkyl or heteroalkyl moiety.

More particularly, the invention utilizes compounds in which NH-L-$R^1$ is: $NHC(O)(CH_2)_aNHC(O)(CH_2)_b(OCH_2CH_2)_cO(CH_2)_dNHR^1$, $NHC(O)(CH_2)_b(OCH_2CH_2)_cO(CH_2)_dNHR^1$, $NHC(O)O(CH_2)_b(OCH_2CH_2)_cO(CH_2)_dNHR^1$, $NH(CH_2)_aNHC(O)(CH_2)_b(OCH_2CH_2)_cO(CH_2)_dNHR^1$, $NHC(O)(CH_2)_aNHR^1$, $NH(CH_2)_aNHR^1$, and $NHR^1$. In these formulae, the indices a, b and d are independently selected from the integers from 0 to 20, preferably from 1 to 5. The index c is an integer from 1 to about 2500.

In an exemplary embodiment, c is selected such that the PEG moiety is approximately 1 kD, 5 kD, 10, kD, 15 kD, 20 kD or 30 kD.

In the discussion that follows, the invention is illustrated by reference to the use of selected derivatives of furanose and pyranose. Those of skill in the art will recognize that the focus of the discussion is for clarity of illustration and that the structures and compositions set forth are generally applicable across the genus of saccharide groups, modified saccharide groups, activated modified saccharide groups and conjugates of modified saccharide groups.

In an exemplary embodiment, the invention provides a glycopeptide that is conjugated to a polymeric modifying moiety through an intact glycosyl linking group having a formula that is selected from:

I

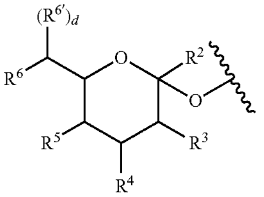

; and

II

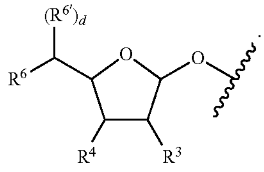

In Formulae I $R^2$ is H, $CH_2OR^7$, $COOR^7$ or $OR^7$, in which $R^7$ represents H, substituted or unsubstituted alkyl or substituted or unsubstituted heteroalkyl. When $COOR^7$ is a carboxylic acid or carboxylate, both forms are represented by the designation of the single structure $COO^-$ or COOH. In Formulae I and II, the symbols $R^3$, $R^4$, $R^5$, $R^6$ and $R^{6'}$ independently represent H, substituted or unsubstituted alkyl, $OR^8$, $NHC(O)R^9$. The index d is 0 or 1. $R^8$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes the polymeric modifying moiety e.g., PEG, linked through a bond or a linking group. In an exemplary embodiment, $R^6$ and $R^{6'}$, together with the carbon to which they are attached are components of the pyruvyl side chain of sialic acid. In a further exemplary embodiment, this side chain is functionalized with the polymeric modifying moiety. In another exemplary embodiment, $R^6$ and $R^{6'}$, together with the carbon to which they are attached are components of the side chain of sialic acid and the polymeric modifying moiety is a component of $R^5$.

In a further exemplary embodiment, the polymeric modifying moiety is bound to the sugar core, generally through a heteroatom, e.g, nitrogen, on the core through a linker, L, as shown below:

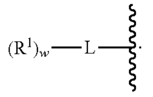

$R^1$ is the polymeric moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety.

An exemplary compound according to the invention has a structure according to Formulae I or II, in which at least one of $R^2$, $R^3$, $R^4$, $R^5$, $R^6$ or $R^{6'}$ has the formula:

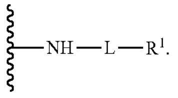

In another example according to this embodiment at least one of $R^2$, $R^3$, $R^4$, $R^5$, $R^6$ or $R^{6'}$ has the formula:

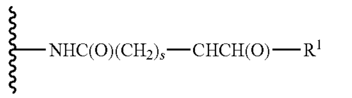

in which s is an integer from 0 to 20 and $R^1$ is a linear polymeric modifying moiety.

In an exemplary embodiment, the polymeric modifying moiety-linker construct is a branched structure that includes two or more polymeric chains attached to central moiety. In this embodiment, the construct has the formula:

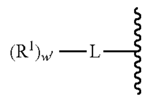

in which $R^1$ and L are as discussed above and w' is an integer from 2 to 6, preferably from 2 to 4 and more preferably from 2 to 3.

When L is a bond it is formed between a reactive functional group on a precursor of $R^1$ and a reactive functional group of complementary reactivity on the saccharyl core. When L is a non-zero order linker, a precursor of L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling the precursors proceeds by chemistry that is well understood in the art.

In an exemplary embodiment, L is a linking group that is formed from an amino acid, or small peptide (e.g., 1-4 amino acid residues) providing a modified sugar in which the polymeric modifying moiety is attached through a substituted alkyl linker. Exemplary linkers include glycine, lysine, serine and cysteine. The PEG moiety can be attached to the amine moiety of the linker through an amide or urethane bond. The PEG is linked to the sulfur or oxygen atoms of cysteine and serine through thioether or ether bonds, respectively.

In an exemplary embodiment, $R^5$ includes the polymeric modifying moiety. In another exemplary embodiment, $R^5$ includes both the polymeric modifying moiety and a linker, L, joining the modifying moiety to the remainder of the molecule. As discussed above, L can be a linear or branched structure. Similarly, the polymeric modifying can be branched or linear.

In one embodiment, the present invention provides an erythropoietin peptide comprising the moiety:

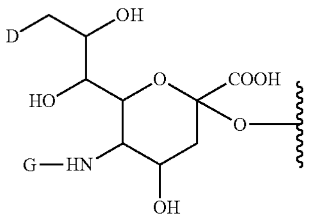

wherein D is a member selected from —OH and $R^1$-L-HN—; G is a member selected from H and $R^1$-L- and —C(O)($C_1$-$C_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is $R^1$-L-, and when G is —C(O)($C_1$-$C_6$)alkyl, D is $R^1$-L-NH—.

In another exemplary embodiment, the invention provides a conjugate formed between a modified sugar of the invention and a substrate EPO peptide. In this embodiment, the sugar moiety of the modified sugar becomes a glycosyl linking group interposed between the peptide substrate and the modifying group. An exemplary glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. Exemplary modifying group-intact glycosyl linking group cassettes according to this motif are based on a sialic acid structure, such as those having the formulae:

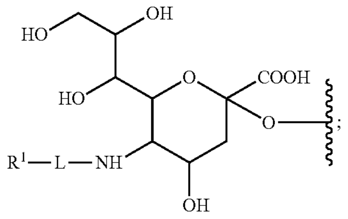

and

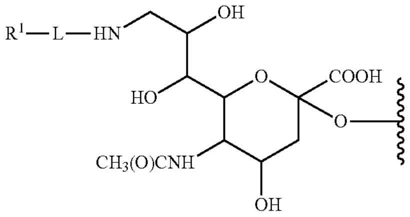

In the formulae above, $R^1$ and L are as described above. Further detail about the structure of exemplary $R^1$ groups is provided below.

In still a further exemplary embodiment, the conjugate is formed between a substrate EPO and a saccharyl moiety in which the modifying group is attached through a linker at the 6-carbon position of the saccharyl moiety. Thus, illustrative conjugates according to this embodiment have the formula:

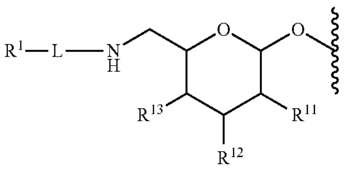

in which the radicals are as discussed above. Such saccharyl moieties include, without limitation, glucose, glucosamine, N-acetyl-glucosamine, galactose, galactosamine, N-acetyl-galactosamine, mannose, mannosamine, N-acetyl-mannosamine, and the like.

Due to the versatility of the methods available for modifying glycosyl residues on a therapeutic peptide such as EPO, the glycosyl structures on the peptide conjugates of the invention can have substantially any structure. Moreover, the glycans can be O-linked or N-linked. As exemplified in the discussion below, each of the pyranose and furanose derivatives discussed above can be a component of a glycosyl moiety of a peptide.

The invention provides a modified EPO peptide that includes a glycosyl group having the formula:

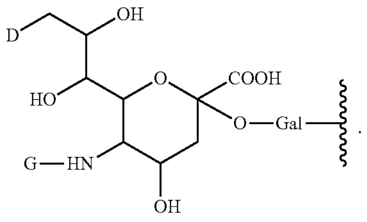

In other embodiments, the group has the formula:

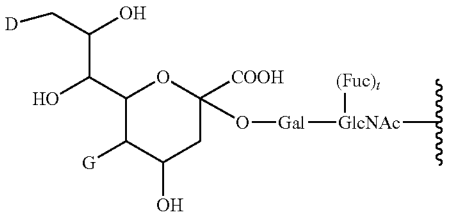

in which the index t is 0 or 1.

In a still further exemplary embodiment, the group has the formula:

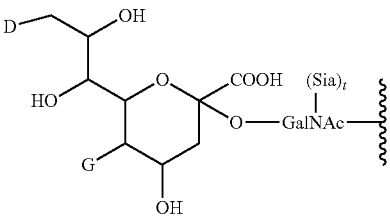

in which the index t is 0 or 1.

In yet another embodiment, the group has the formula:

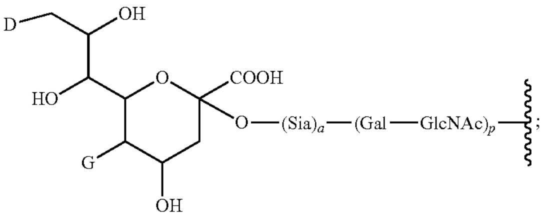

in which the index p represents and integer from 1 to 10; and a is either 0 or 1.

In an exemplary embodiment, a glycoPEGylated EPO peptide of the invention includes at least one N-linked glycosyl residue selected from the glycosyl residues set forth below:

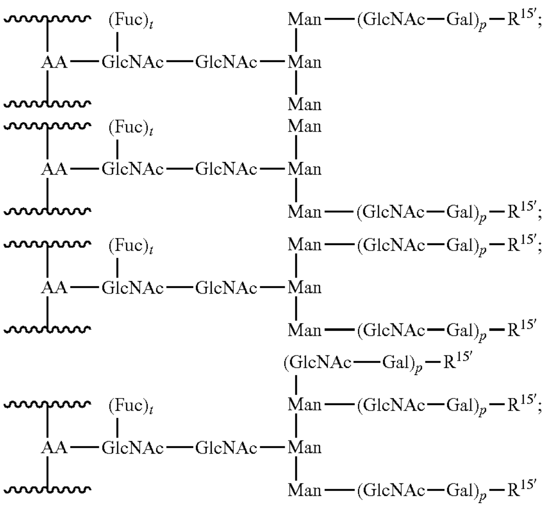

-continued

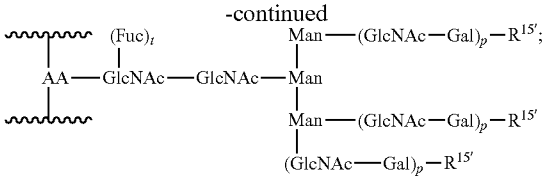

and

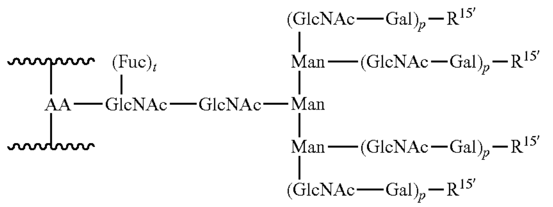

In the formulae above, the index t is 0 or 1 and the index p is an integer from 1 to 10. The symbol $R^{15'}$ represents H, OH (e.g., Gal-OH), a sialyl moiety, a polymer modified sialyl moiety (i.e., glycosyl linking group-polymeric modifying moiety (Sia-L-$R^1$)) or a sialyl moiety to which is bound a polymer modified sialyl moiety (e.g., Sia-Sia-L-$R^1$) ("Sia-$Sia^p$"). Exemplary polymer modified saccharyl moieties have a structure according to Formulae I and II. An exemplary EPO peptide of the invention will include at least one glycan having a $R^{15'}$ that includes a structure according to Formulae I or II. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3-to the galactose residue. In another exemplary embodiment, the sialic acid is linked α2,6-to the galactose residue.

The modified glycan is bound to one or more position selected from Asn 24, Asn 38, Asn 83 and/or Ser 126. In an exemplary embodiment, the EPO is derived from mammalian cells and the modifying group is only on the glycan at Asn 24. In one embodiment according to this motif, the glycosyl linking moiety is linked to a Sia residue through another Sia residue, e.g.:

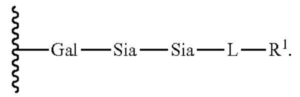

An exemplary species according to this motif is prepared by conjugating Sia-L-$R^1$ to a terminal sialic acid of the glycan at Asn 24 using an enzyme that forms Sia-Sia bonds, e.g., CST-II, ST8Sia-II, ST8Sia-III and ST8Sia-IV.

In another exemplary embodiment, the glycans have a formula that is selected from the group:

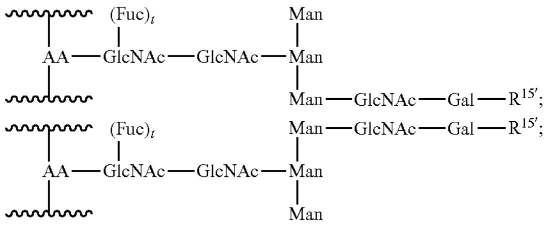

and

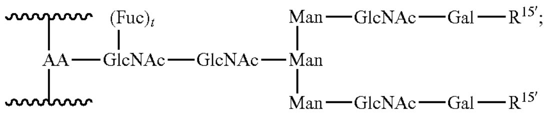

and a combination thereof.

Figure 2A:
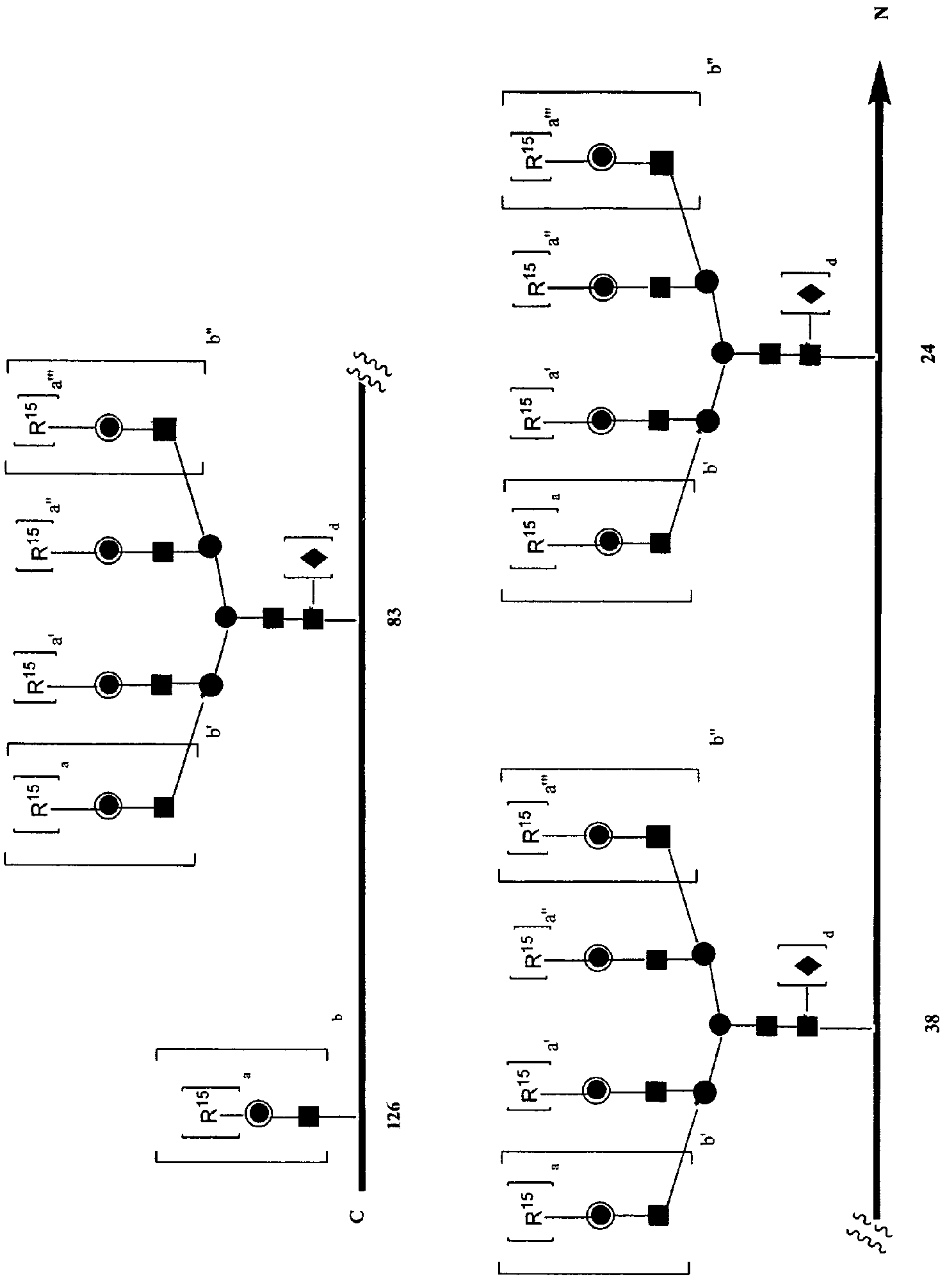
FIG. 2A and FIG. 2B are exemplary in that any glycosylated EPO molecule may comprise any mixture of mono-, bi- tri-, or tetra-antennary N-linked glycosyl residues and any one or more of the branches may further comprise a modified sialic acid moiety. Moreover, the modified glycan can be positioned at any one or more N- or O-linked glycosylation site without limitation. Each of the indices is independently selected from 0 and 1, and $R^{15}$ is as described herein. The peptide includes at least one $R^{15}$ moiety that includes a branched or linear PEG moiety. In this and each of the other figures in which the symbol  appears, it represents a discontinuity in the representation of the peptide chain due to the size of the drawing. The representation is continued on the subsequent line. The symbol does not imply an actual break in the peptide sequence.
Figure 2B:
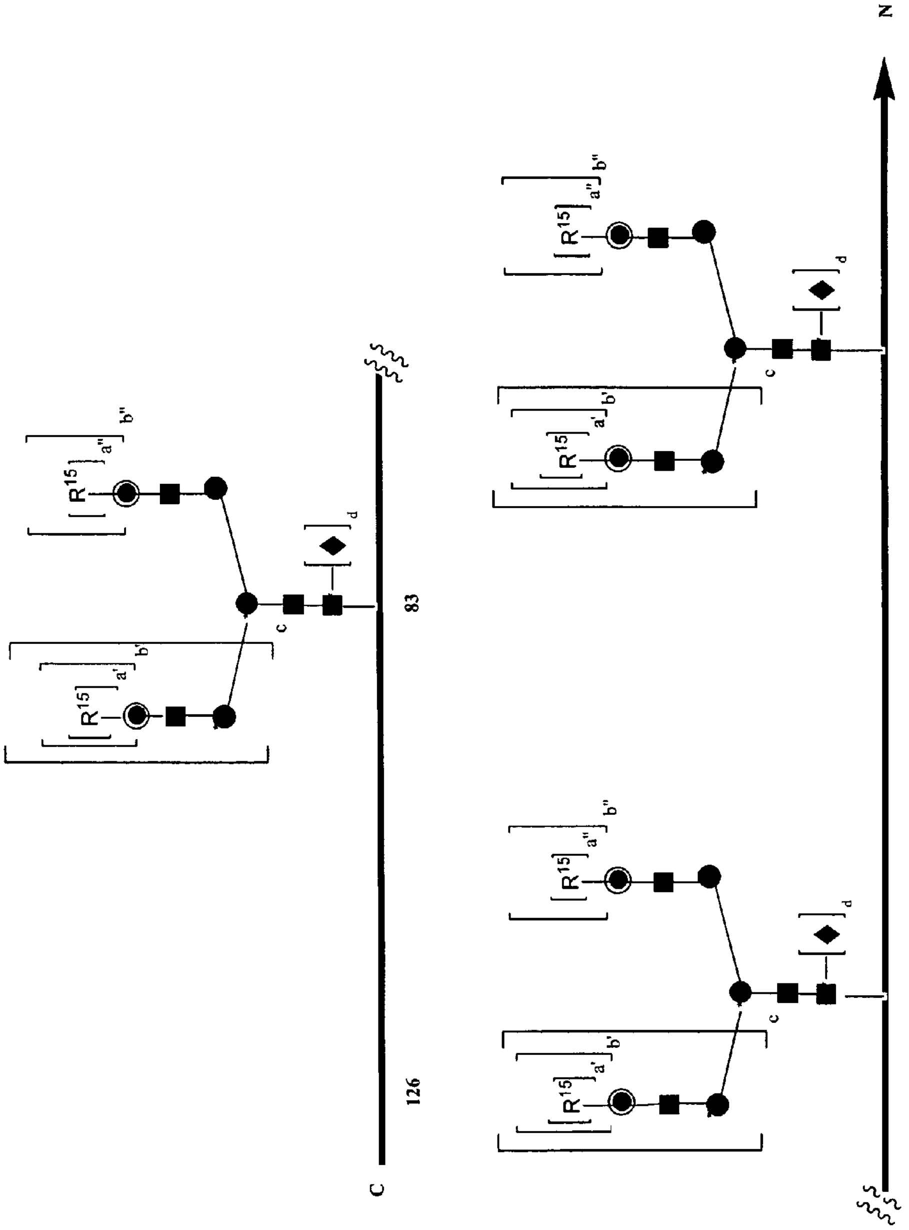
Figure 3:
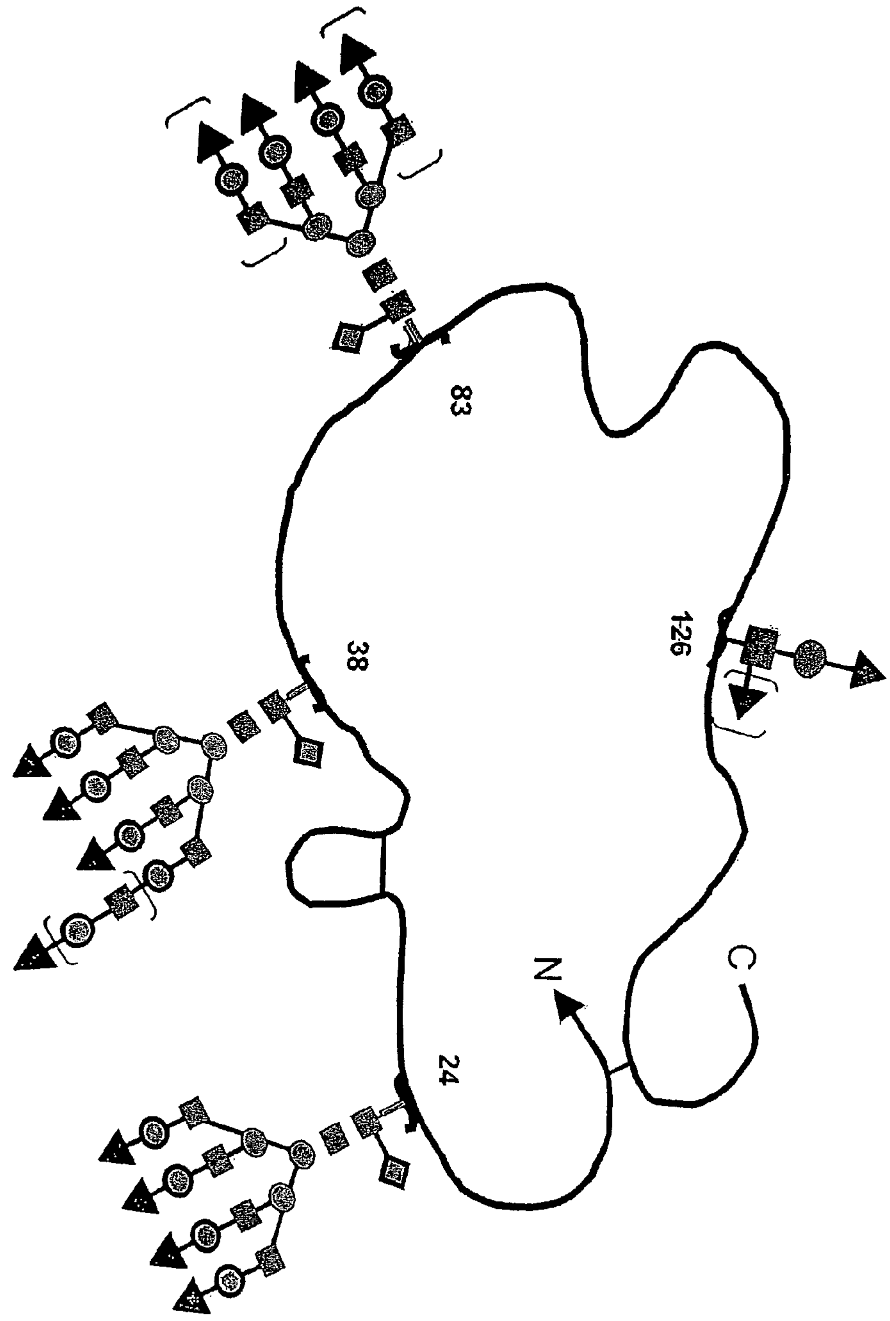
FIG. 3 illustrates an exemplary CHO-derived EPO peptide in its non-glycoPEGylated form. The figure is exemplary in that any glycosylated EPO molecule may comprise any mixture of mono-, bi- tri-, or tetra-antennary N-linked glycosyl residues and any one or more of the branches may further comprise a modified sialic acid moiety of the invention. Moreover, the figure illustrates that the modified glycan can be positioned at any one or more N- or O-linked glycosylation site without limitation.
Figure 4:
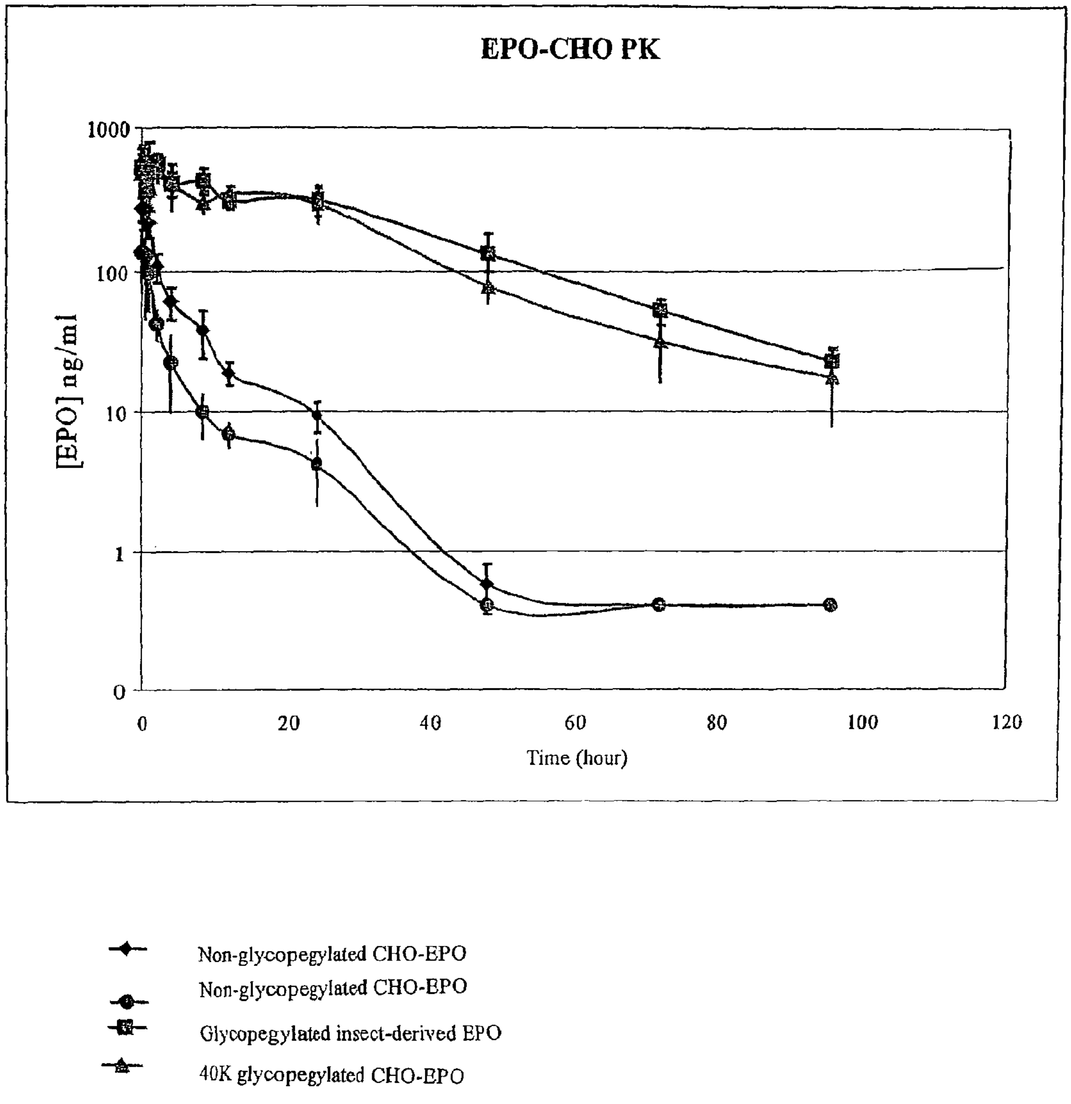
FIG. 4 shows the results of experiments comparing the pharmacokinetics of two CHO-derived non-glycoPEGylated EPO forms, and two different CHO-derived glycoPEGylated EPO forms.

The glycans of this group generally correspond to those found on an EPO peptide that is produced by insect cells (e.g., Sf-9), followed by remodeling of the glycan and glycoPEGylation according to the methods set forth herein. For example insect-derived EPO that is expressed with a tri-mannosyl core is subsequently contacted with a GlcNAc donor and a GlcNAc transferase and a Gal donor and a Gal transferase. Appending GlcNAc and Gal to the tri-mannosyl core is accomplished in either two steps or a single step. A modified sialic acid is added to at least one branch of the glycosyl moiety as discussed herein. Those Gal moieties that are not functionalized with the modified sialic acid are optionally "capped" by reaction with a sialic acid donor in the presence of a sialyl transferase. See, FIG. 2A, FIG. 2B and FIG. 3 for exemplary structures of glycans that include sialyl capped galactose residues, and mixtures of sialyl capped and uncapped galactose residues.

In an exemplary embodiment, at least 60% of terminal Gal moieties in a population of peptides is capped with sialic acid, preferably at least 70%, more preferably, at least 80%, still more preferably at least 90% and even more preferably at least 95%, 96%, 97%, 98% or 99% are capped with sialic acid.

In each of the formulae above, $R^{15'}$ is as discussed above. Moreover, an exemplary modified EPO peptide of the invention will include at least one glycan with an $R^{15'}$ moiety having a structure according to Formulae I or II.

In another exemplary embodiment, the EPO is derived from insect cells, which are remodeled by adding GlcNAc and Gal to the mannose core. The remodeled peptide is glycopegylated using a sialic acid bearing a linear PEG moiety, affording an EPO peptide that comprises at least one moiety having the formula:

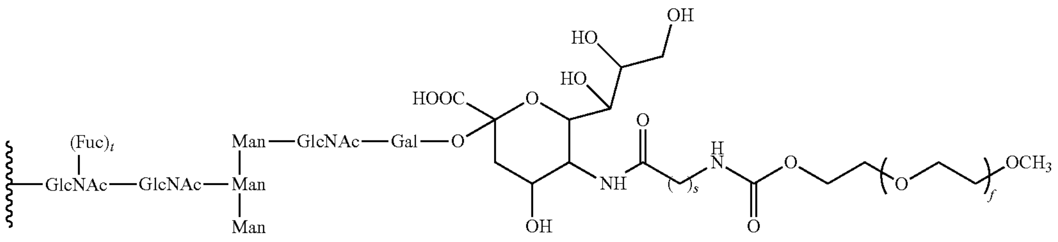

in which s represents and integer from 1 to 10; and f represents and integer from 1 to 2500.

Figure 5:
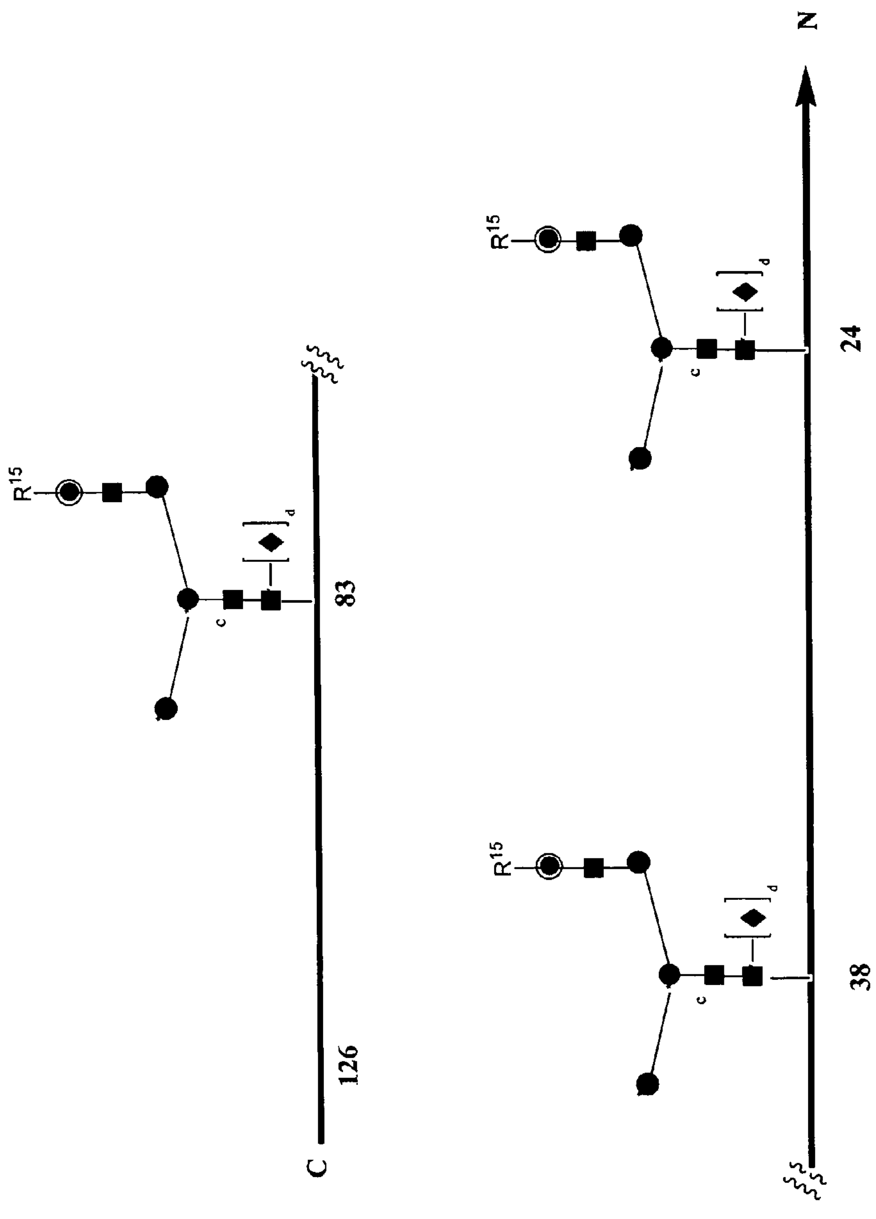
FIG. 5 illustrates an insect-derived remodeled and glycoPEGylated EPO peptide according to the invention.

In certain embodiments, the EPO peptide includes three such moieties, one attached at each of Asn 24, Asn 38 and Asn 83. In another embodiment, the peptide includes two such moieties attached at a combination of two of these Asn moieties. There is also provided a composition that is a mixture of these two species (i.e., $PEG_3$ and $PEG_2$). The mixture preferably includes at least 75%, preferably at least 80%, more preferably at least 85%, still more preferably 90% and even more preferably 95%, 96%, 97% or 98% of the species that includes the three modified glycosyl residues. Unmodified terminal Gal residues are optionally capped with Sia as discussed above. In an exemplary embodiment, the peptide is expressed in insect cells, remodeled and glycopegylated (FIG. 5).

The indices e and q are as discussed above. In an exemplary embodiment, e for each of the modified glycosyl moieties is an integer that provides as PEG moiety having a molecular weight of approximately 10 kDa.

An exemplary precursor of use to form the branched conjugates according to this embodiment of the invention has the formula:

(III)

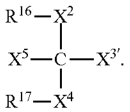

The branched polymer species according to this formula are essentially pure water-soluble polymers. $X^{3'}$ is a moiety that includes an ionizable, e.g., OH, COOH, $H_2PO_4$, $HSO_3$, $HPO_3$, and salts thereof, etc.) or other reactive functional group, e.g., infra. C is carbon. $X^5$ is preferably a non-reactive group (e.g., H, unsubstituted alkyl, unsubstituted heteroalkyl), and can be a polymeric arm. $R^{16}$ and $R^{17}$ are independently selected polymeric arms, e.g., nonpeptidic, nonreactive polymeric arms (e.g., PEG)). $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^{16}$ and $R^{17}$ to C. When $X^{3'}$ is reacted with a reactive functional group of complementary reactivity on a linker, sugar or linker-sugar cassette, $X^{3'}$ is converted to a component of linkage fragment $X^3$.

Exemplary linkage fragments for $X^2$, $X^3$ and $X^4$ are independently selected and include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, the precursor (III), or an activated derivative thereof, is reacted with, and thereby bound to a sugar, an activated sugar or a sugar nucleotide through a reaction between $X^3$ and a group of complementary reactivity on the sugar moiety, e.g., an amine. Alternatively, $X^{3'}$ reacts with a reactive functional group on a precursor to linker, L. One or more of $R^2$, $R^3$, $R^4$, $R^5$ $R^6$ or $R^{6'}$ of Formulae I and II can include the branched polymeric modifying moiety, or this moiety bound through L.

In an exemplary embodiment, the moiety:

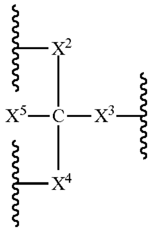

is the linker arm, L. In this embodiment, an exemplary linker is derived from a natural or unnatural amino acid, amino acid analogue or amino acid mimetic, or a small peptide formed from one or more such species. For example, certain branched polymers found in the compounds of the invention have the formula:

(IV)

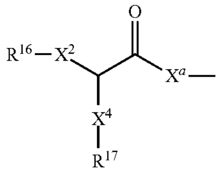

$X^a$ is a linkage fragment that is formed by the reaction of a reactive functional group, e.g., $X^{3'}$, on a precursor of the branched polymeric modifying moiety and a reactive functional group on the sugar moiety, or a precursor to a linker. For example, when $X^{3'}$ is a carboxylic acid, it can be activated and bound directly to an amine group pendent from an aminosaccharide (e.g., Sia, $GalNH_2$, $GlcNH_2$, $ManNH_2$, etc.), forming an $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

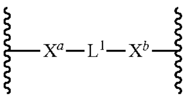

in which $X^b$ is a second linkage fragment and is independently selected from those groups set forth for $X^a$, and, similar to L, $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide (e.g., Lys-Lys) or tri-peptide (E.G., Lys-Lys-Lys) in which the alpha-amine moiety(ies) and/or side chain heteroatom(s) are modified with a polymeric modifying moiety.

In a further exemplary embodiment, the conjugates of the invention include a moiety, e.g., an $R^{15}$ moiety that has a formula that is selected from:

V

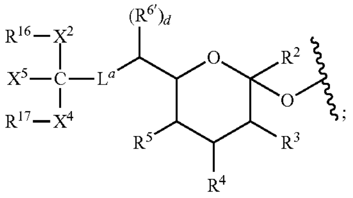

; and

VI

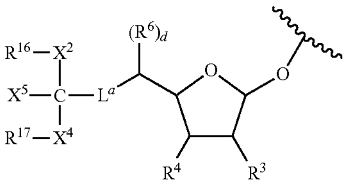

in which the identity of the radicals represented by the various symbols is the same as that discussed hereinabove. $L^a$ is a bond or a linker as discussed above for L and $L^1$, e.g., substituted or unsubstituted alkyl or substituted or unsubstituted heteroalkyl moiety. In an exemplary embodiment, $L^a$ is a moiety of the side chain of sialic acid that is functionalized with the polymeric modifying moiety as shown. Exemplary $L^a$ moieties include substituted or unsubstituted alkyl chains that include one or more OH or $NH_2$.

In yet another exemplary embodiment, the invention provides conjugates having a moiety, e.g., an $R^{15}$ moiety with formula:

VI

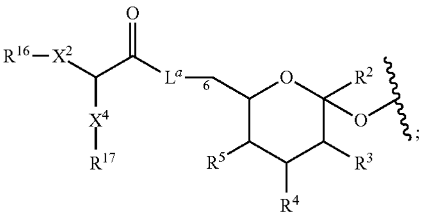

; and

-continued

VII

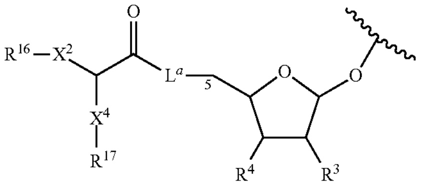

The identity of the radicals represented by the various symbols is the same as that discussed hereinabove. As those of skill will appreciate, the linker arm in Formulae VI and VII is equally applicable to other modified sugars set forth herein. In exemplary embodiment, the species of Formulae VI and VII are the $R^{15}$ moieties attached to the glycan structures set forth herein.

In yet another exemplary embodiment, the EPO peptide includes an $R^{15}$ moiety with the formula:

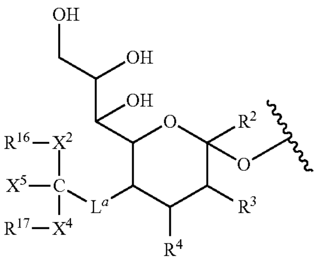

in which the identities of the radicals are as discussed above. An exemplary species for $L^a$ is $—CH_2)_jC(O)NH(CH_2)_hC(O)NH—$, in which h and j are independently selected integers from 0 to 10. A further exemplary species is —C(O)NH—.

The embodiments of the invention set forth above are further exemplified by reference to species in which the polymer is a water-soluble polymer, particularly poly(ethylene glycol) ("PEG"), e.g., methoxy-poly(ethylene glycol). Those of skill will appreciate that the focus in the sections that follow is for clarity of illustration and the various motifs set forth using PEG as an exemplary polymer are equally applicable to species in which a polymer other than PEG is utilized.

PEG of any molecular weight, e.g., 1 kDa, 2 kDa, 5 kDa, 10 kDa, 15 kDa, 20 kDa, 30 kDa and 40 kDa is of use in the present invention.

In an exemplary embodiment, the $R^{15}$ moiety has a formula that is a member selected from the group:

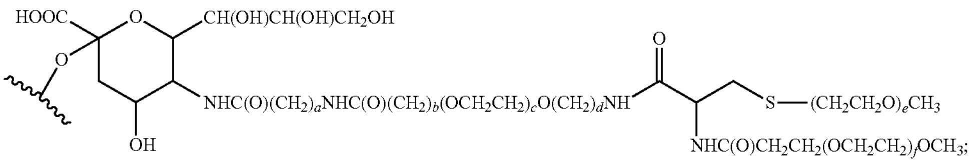

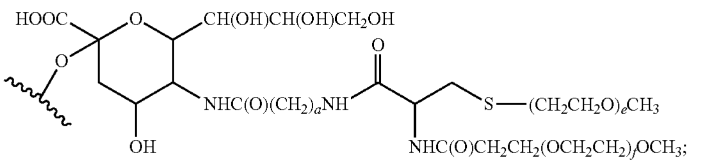

-continued
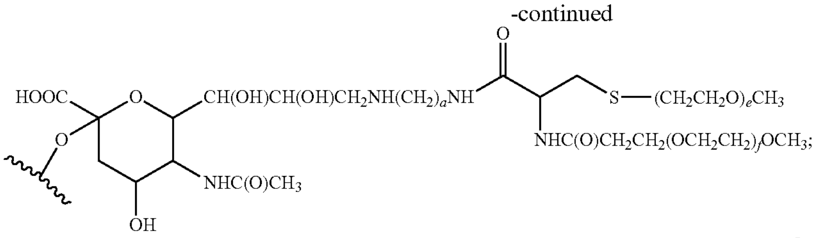
and
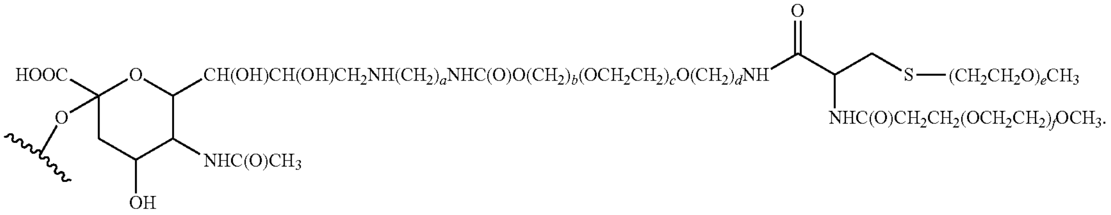
In other exemplary embodiments, the conjugate includes an $R^{15}$ moiety selected from the group:
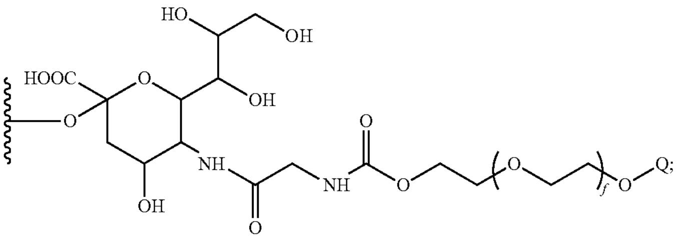
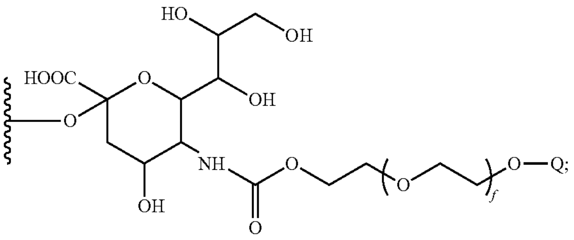
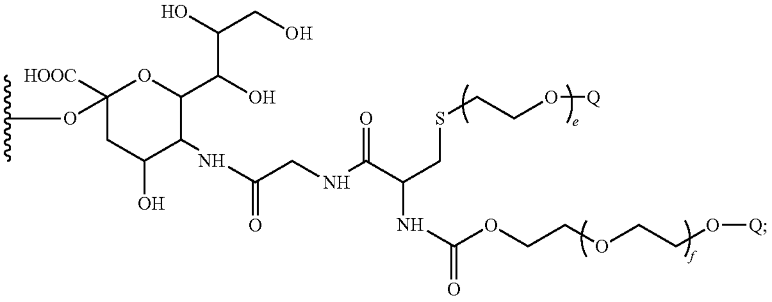
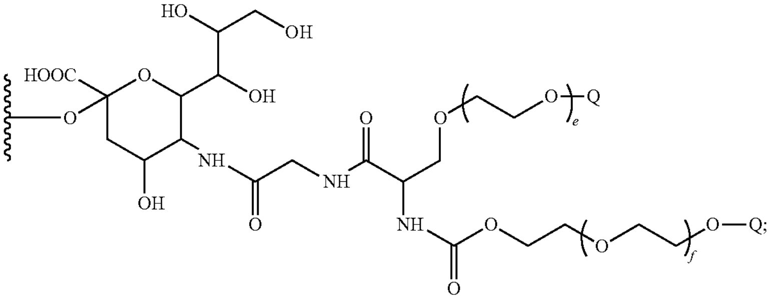
and -continued

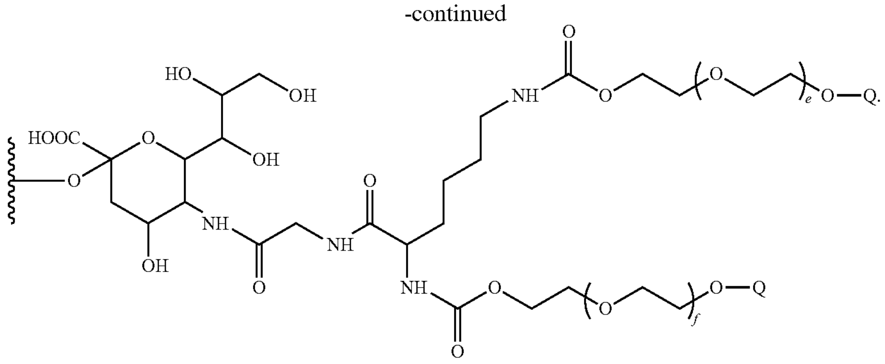

In each of the formulae above, the indices e and f are independently selected from the integers from 1 to 2500. In further exemplary embodiments, e and f are selected to provide a PEG moiety that is about 1 kD, 2 kD, 10 kD, 15 kD, 20 kD, 30 kD or 40 kD. The symbol Q represents substituted or unsubstituted alkyl (e.g., $C_1$-$C_6$ alkyl, e.g., methyl), substituted or unsubstituted heteroalkyl or H.

Other branched polymers have structures based on di-lysine (Lys-Lys) peptides, e.g.:

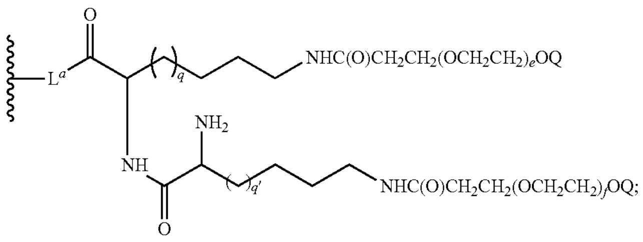

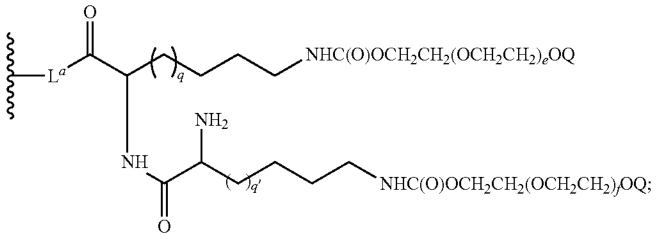

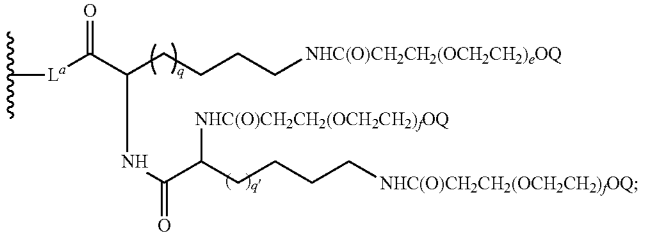

and

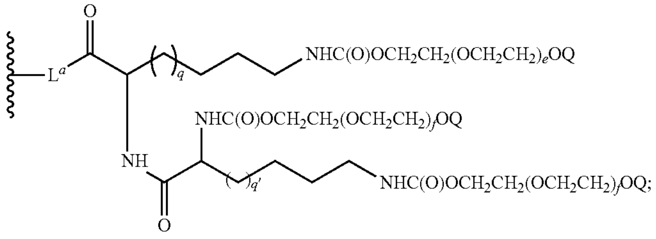

and tri-lysine peptides (Lys-Lys-Lys), e.g.:

-continued

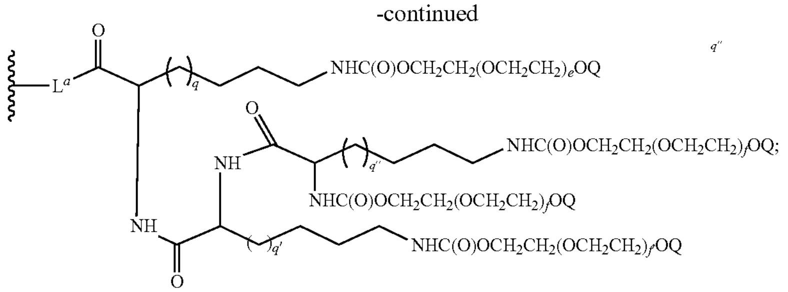

and

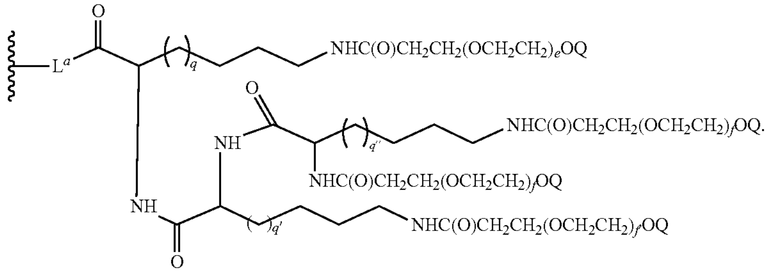

In each of the figures above, e, f, f' and f'' represent integers independently selected from 1 to 2500. The indices q, q' and q'' represent integers independently selected from 1 to 20.

In another exemplary embodiment, the EPO peptide comprises a glycosyl moiety selected from the formulae:

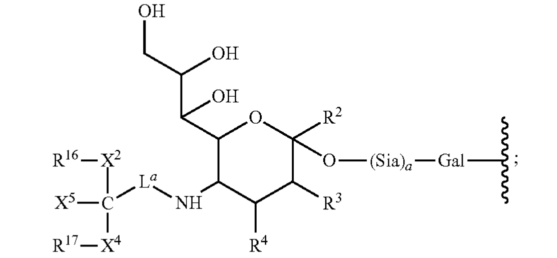

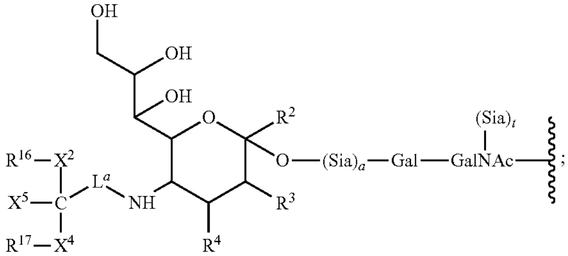

and

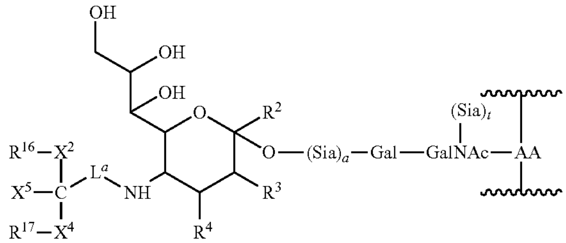

in which $L^a$ is a bond or a linker as described herein; the index t represents 0 or 1; and the index a represents 0 or 1. Each of these groups can be included as components of the mono-, bi-, tri- and tetra-antennary saccharide structures set forth above.

In yet another embodiment, the conjugates of the invention include a modified glycosyl residue that includes the substructure selected from:

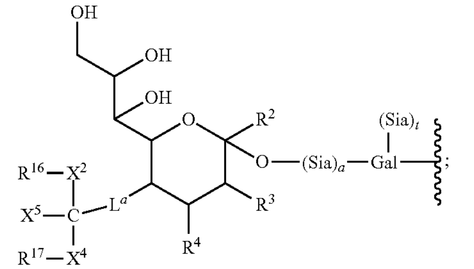

and

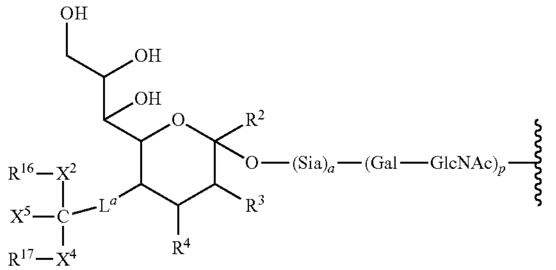

in which the index a and the linker $L^a$ are as discussed above. The index p is an integer from 1 to 10. The indices t and a are independently selected from 0 or 1. Each of these groups can be included as components of the mono-, bi-, tri- and tetra-antennary saccharide structures set forth above.

In a further exemplary embodiment, the invention utilizes modified sugars in which the 6-hydroxyl position is converted to the corresponding amine moiety, which bears a linker-modifying group cassette such as those set forth above. Exemplary saccharyl groups that can be used as the core of these modified sugars include Gal, GalNAc, Glc, GlcNAc, Fuc, Xyl, Man, and the like. A representative modified sugar according to this embodiment has the formula:

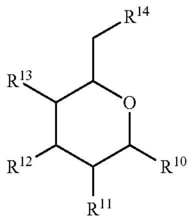

in which $R^{11}$-$R^{14}$ are members independently selected from H, OH, $C(O)CH_3$, NH, and NH $C(O)CH_3$. $R^{10}$ is a link to another glycosyl residue (—O-glycosyl) or to an amino acid of the EPO peptide (—NH-EPO). $R^{14}$ is $OR^1$, $NHR^1$ or NH-L-$R^1$. $R^1$ and NH-L-$R^1$ are as described above.

Selected conjugates according to this motif are based on mannose, galactose or glucose, or on species having the stereochemistry of mannose, galactose or glucose. The general formulae of these conjugates are:

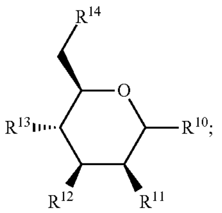

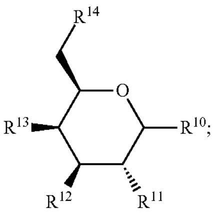

and

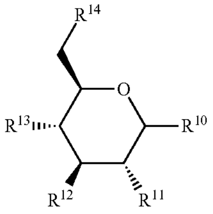

As discussed above, the invention provides saccharides bearing a modifying group, activated analogues of these species and conjugates formed between species such as peptides and lipids and a modified saccharide of the invention.

Modified Sugars

The present invention uses modified sugars and modified sugar nucleotides to form conjugates of the modified sugars. In modified sugar compounds of use in the invention, the sugar moiety is preferably a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the sugar moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any sugar can be utilized as the sugar core of the glycosyl linking group of the conjugates of the invention. Exemplary sugar cores that are useful in forming the compositions of the invention include, but are not limited to, glucose, galactose, mannose, fucose, and sialic acid. Other useful sugars include amino sugars such as glucosamine, galactosamine, mannosamine, the 5-amine analogue of sialic acid and the like. The sugar core can be a structure found in nature or it can be modified to provide a site for conjugating the modifying group. For example, in one embodiment, the invention provides a sialic acid derivative in which the 9-hydroxy moiety is replaced with an amine. The amine is readily derivatized with an activated analogue of a selected modifying group.

Exemplary modified sugars are modified with water-soluble or water-insoluble polymers. Examples of useful polymer are further exemplified below.

Water-Soluble Polymers

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids), e.g., poly(aspartic acid) and poly(glutamic acid); nucleic acids; synthetic polymers (e.g., poly(acrylic acid), poly (ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly (ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

The modified sugars are prepared by reacting the glycosyl core (or a linker on the core) with a polymeric modifying moiety (or a linker on the polymeric modifying moiety). The discussion that follows provides examples of selected polymeric modifying moieties of use in the invention. For example, representative polymeric modifying moieties include structures that are based on side chain-containing amino acids, e.g., serine, cysteine, lysine, and small peptides, e.g., lys-lys. Exemplary structures include:

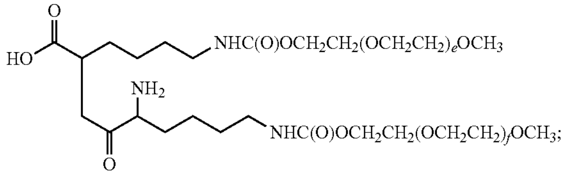

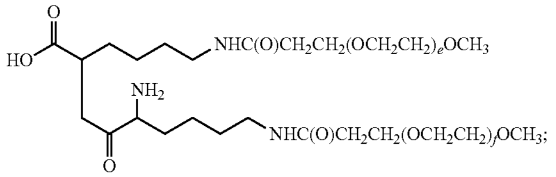

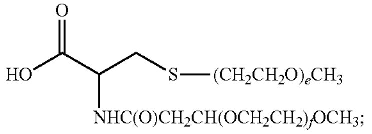

-continued

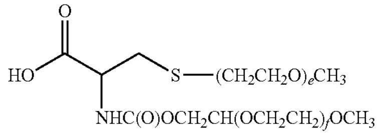

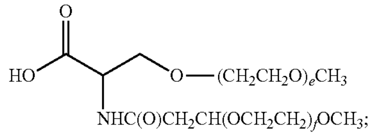

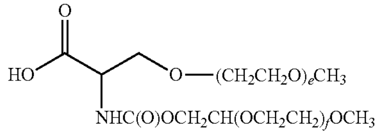

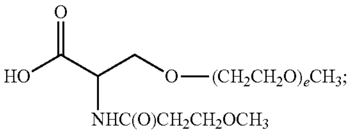

and

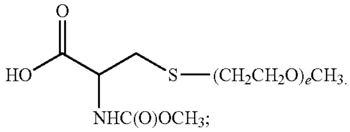

Those of skill will appreciate that the free amine in the di-lysine structures can also be pegylated through an amdie or urethane bond with a PEG moiety.

In yet another embodiment, the branched PEG moiety is based upon a tri-lysine peptide. The tri-lysine can be mono-, di-, tri-, or tetra-PEG-ylated. Exemplary species according to this embodiment have the formulae:

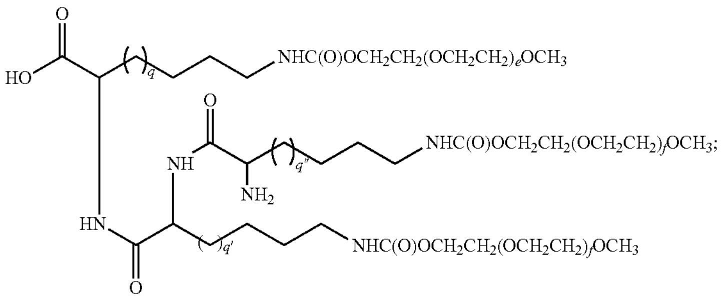

and

-continued

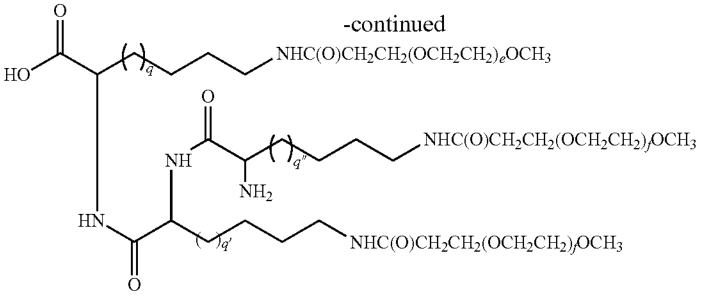

in which e, f and f' are independently selected integers from 1 to 2500; and q, q' and q" are independently selected integers from 1 to 20.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits labeled with the polymeric modifying moiety in a desired manner is within the scope of the invention.

The polymeric modifying moieties can be activated for reaction with the glycosyl core. Exemplary structures of activated species (e.g., carbonates and active esters) include:

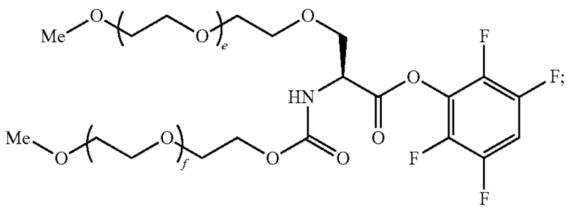

and

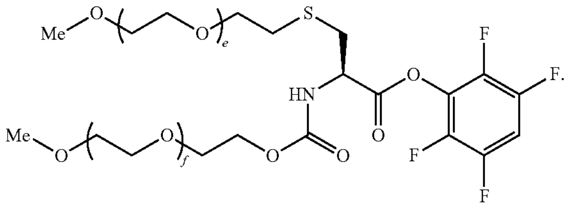

Other activating, or leaving groups, appropriate for activating linear and branched PEGs of use in preparing the compounds set forth herein include, but are not limited to the species:

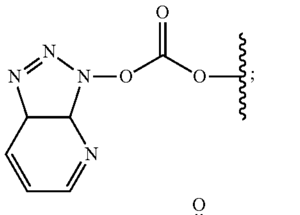

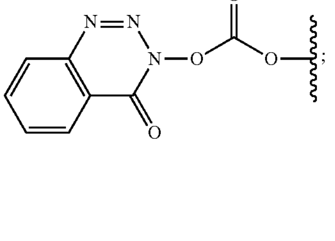

-continued

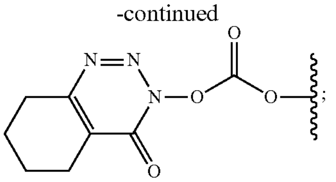

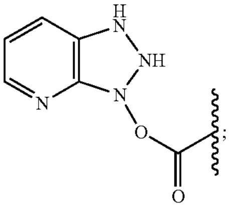

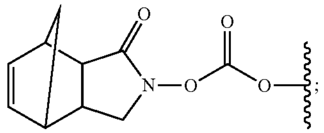

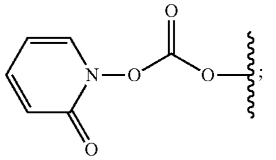

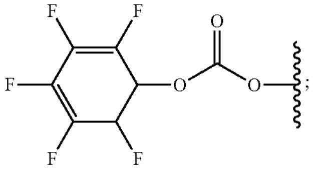

and

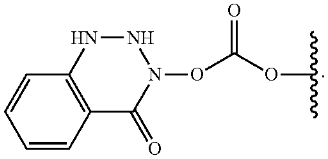

PEG molecules that are activated with these and other species and methods of making the activated PEGs are set forth in WO 04/083259.

Those of skill in the art will appreciate that one or more of the m-PEG arms of the branched polymers shown above can be replaced by a PEG moiety with a different terminus, e.g., OH, COOH, $NH_2$, $C_2$-$C_{10}$-alkyl, etc. Moreover, the structures above are readily modified by inserting alkyl linkers (or removing carbon atoms) between the α-carbon atom and the functional group of the amino acid side chain. Thus, "homo" derivatives and higher homologues, as well as lower homologues are within the scope of cores for branched PEGs of use in the present invention.

The branched PEG species set forth herein are readily prepared by methods such as that set forth in the scheme below:

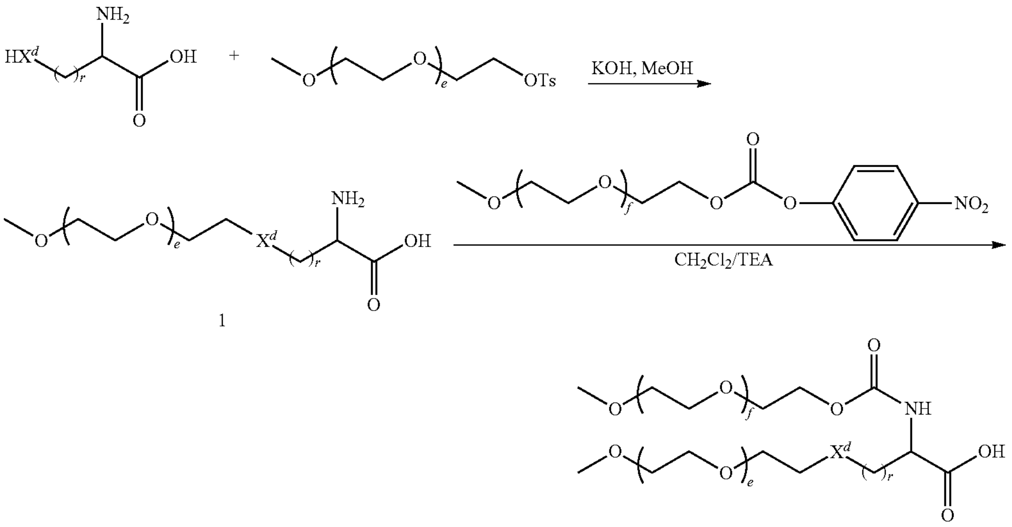

1

2 in which $X^d$ is O or S and r is an integer from 1 to 5. The indices e and f are independently selected integers from 1 to 2500. In an exemplary embodiment, one or both of these indices are selected such that the polymer is about 10 kD, 15 kD or 20 kD in molecular weight.

Thus, according to this scheme, a natural or unnatural amino acid is contacted with an activated m-PEG derivative, in this case the tosylate, forming 1 by alkylating the side-chain heteroatom $X^d$. The mono-functionalize m-PEG amino acid is submitted to N-acylation conditions with a reactive m-PEG derivative, thereby assembling branched m-PEG 2. As one of skill will appreciate, the tosylate leaving group can be replaced with any suitable leaving group, e.g., halogen, mesylate, triflate, etc. Similarly, the reactive carbonate utilized to acylate the amine can be replaced with an active ester, e.g., N-hydroxysuccinimide, etc., or the acid can be activated in situ using a dehydrating agent such as dicyclohexylcarbodiimide, carbonyldiimidazole, etc.

In other exemplary embodiments, the urea moiety is replaced by a group such as a amide.

In an illustrative embodiment, the modified sugar is sialic acid and selected modified sugar compounds of use in the invention have the formulae:

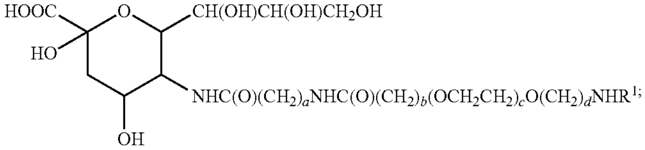
;
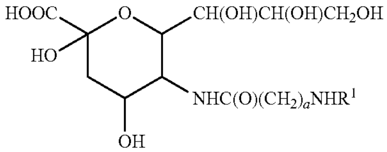
;
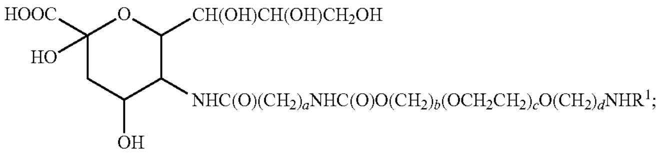
;
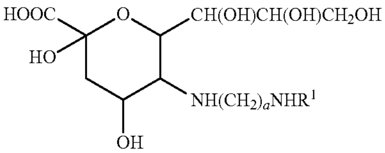
;
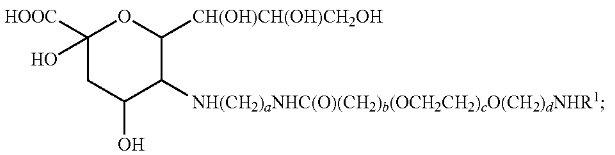
;
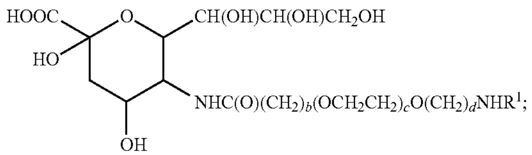
;
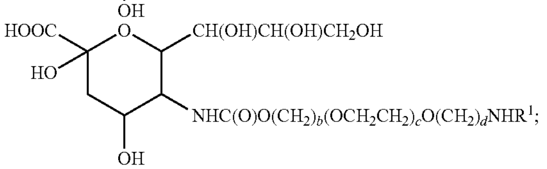
;
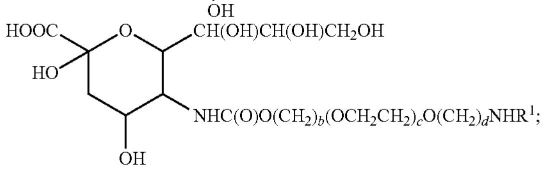
; and -continued

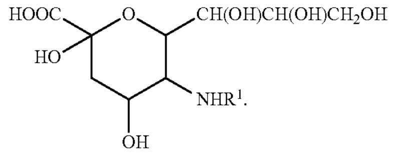

The indices a, b and d are integers from 0 to 20. The index c is an integer from 1 to 2500. The structures set forth above can be components of $R^{15}$.

In another illustrative embodiment, a primary hydroxyl moiety of the sugar is functionalized with the modifying group. For example, the 9-hydroxyl of sialic acid can be converted to the corresponding amine and functionalized to provide a compound according to the invention. Formulae according to this embodiment include:

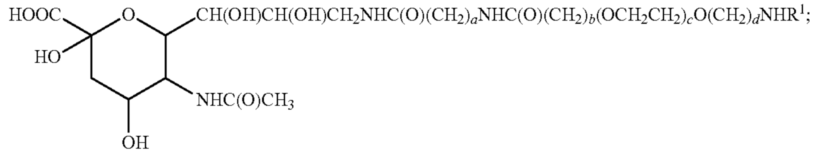

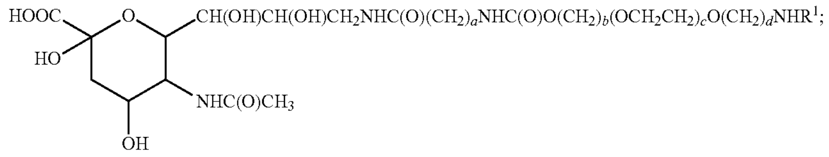

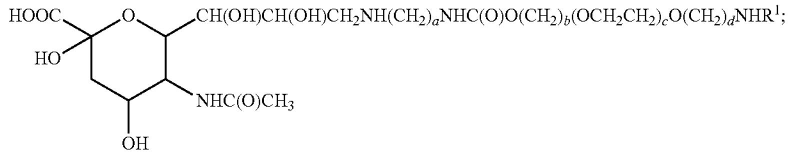

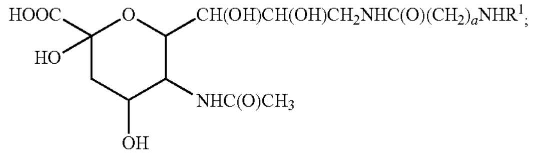

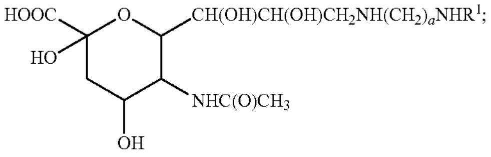

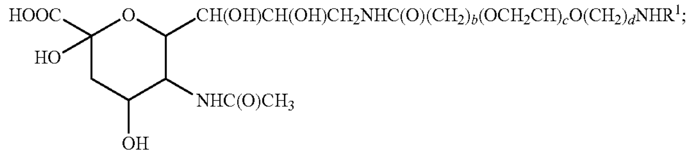

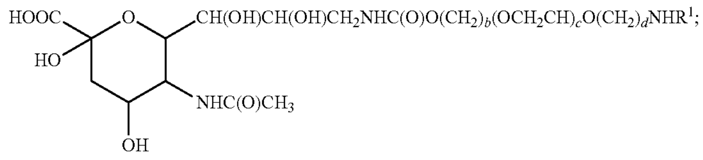

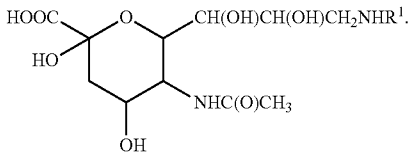

The structures set forth above can be components of $R^{15}$.

As those of skill in the art will appreciate, the sialic acid moiety in the exemplary compounds above can be replaced with any other amino-saccharide including, but not limited to, glucosamine, galactosamine, mannosamine, their N-acyl derivatives, and the like.

Although the present invention is exemplified in the preceding sections by reference to PEG, as those of skill will appreciate, an array of polymeric modifying moieties is of use in the compounds and methods set forth herein.

In selected embodiments, $R^1$ or L-$R^1$ is a branched PEG, for example, one of the species set forth above. Illustrative modified sugars according to this embodiment include:

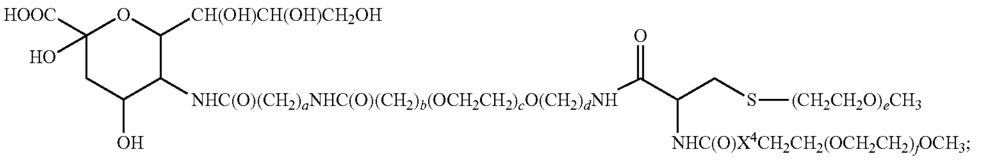

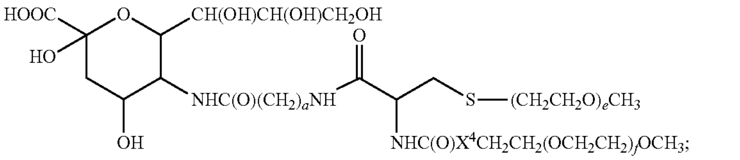

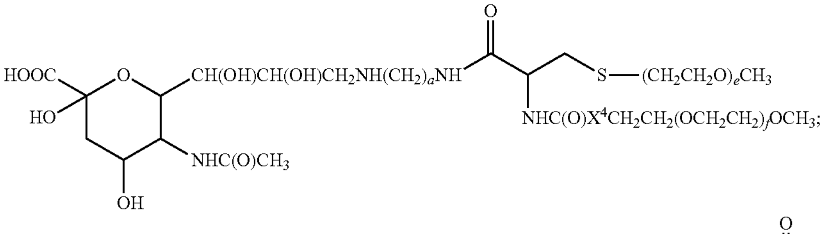

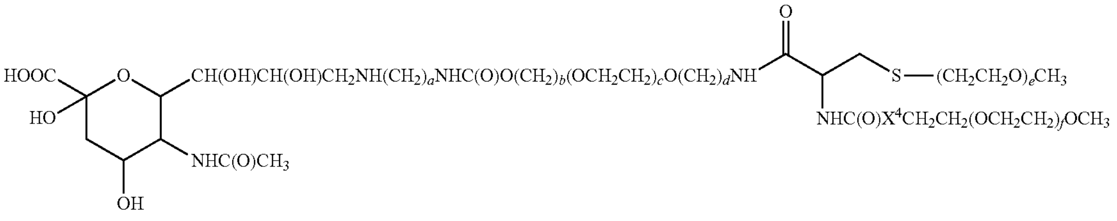

in which $X^4$ is a bond or O. In each of the structures above, the alkylamine linker —$(CH_2)_a$NH— can be present or absent. The structures set forth above can be components of $R^{15}/R^{15'}$.

As discussed herein, the polymer-modified sialic acids of use in the invention may also be linear structures. Thus, the invention provides for conjugates that include a sialic acid moiety derived from a structure such as:

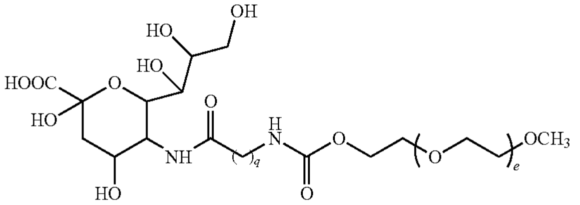

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. Polymeric Drugs And Drug Delivery Systems, ACS Symposium Series Vol. 469, American Chemical Society, Washington, D.C. 1991. Those of skill in the art will appreciate that substantially any known drug delivery system is applicable to the conjugates of the present invention.

The motifs forth above for $R^1$, L-$R^1$, $R^{15}$, $R^{15'}$ and other radicals are equally applicable to water-insoluble polymers, which may be incorporated into the linear and branched structures without limitation utilizing chemistry readily accessible to those of skill in the art.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly (isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly(α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301-1316 (1987); and Cohn et al., *J. Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly (carbonates), poly(phosphazines), poly(phosphoesters), poly (thioesters), polysaccharides and mixtures thereof. More preferably still, the biosresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly (propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly (ethylene glycol); whereas, the hydrolytically labile extensions can be a poly(α-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, is of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

The Methods

In addition to the conjugates discussed above, the present invention provides methods for preparing these and other conjugates. Moreover, the invention provides methods of preventing, curing or ameliorating a disease state by administering a conjugate of the invention to a subject at risk of developing the disease or a subject that has the disease.

In exemplary embodiments, the conjugate is formed between a polymeric modifying moiety and a glycosylated or non-glycosylated peptide. The polymer is conjugated to the peptide via a glycosyl linking group, which is interposed between, and covalently linked to both the peptide (or glycosyl residue) and the modifying group (e.g., water-soluble polymer). The method includes contacting the peptide with a mixture containing a modified sugar and an enzyme, e.g., a glycosyltransferase that conjugates the modified sugar to the substrate. The reaction is conducted under conditions appropriate to form a covalent bond between the modified sugar and the peptide. The sugar moiety of the modified sugar is preferably selected from nucleotide sugars.

In an exemplary embodiment, the modified sugar, such as those set forth above, is activated as the corresponding nucleotide sugars. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the sugar nucleotide portion of the modified sugar nucleotide is selected from UDP-galactose, UDP-galactosamine, UDP-glucose, UDP-glucosamine, GDP-mannose, GDP-fucose, CMP-sialic acid, or CMP-NeuAc. In an exemplary embodiment, the nucleotide phosphate is attached to C-1.

Thus, in an illustrative embodiment in which the glycosyl moiety is sialic acid, the method of the invention utilizes compounds having the formulae:

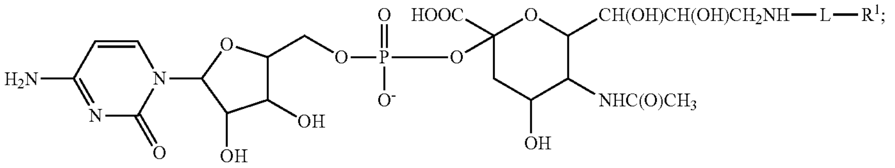

and

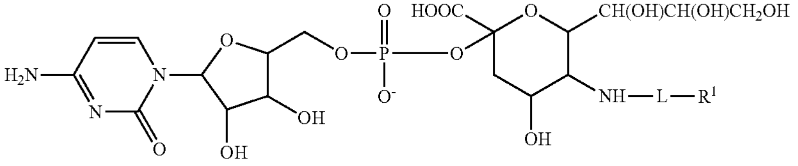

in which L-$R^1$ is as discussed above, and $L^1$-$R^1$ represents a linker bound to the modifying group. As with L, exemplary linker species according to $L^1$ include a bond, alkyl or heteroalkyl moieties.

Moreover, as discussed above, the present invention provides for the use of nucleotide sugars that are modified with a water-soluble polymer, which is either straight-chain or branched. For example, compounds having the formula shown below are of use to prepare conjugates within the scope of the present invention:

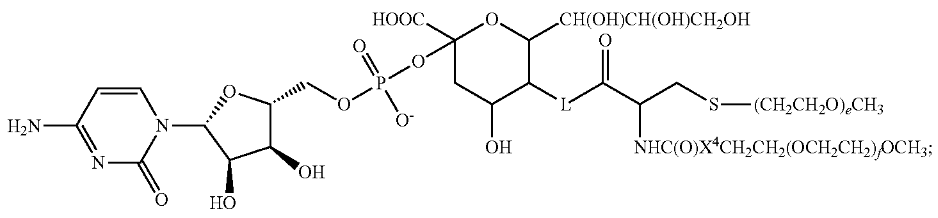

and

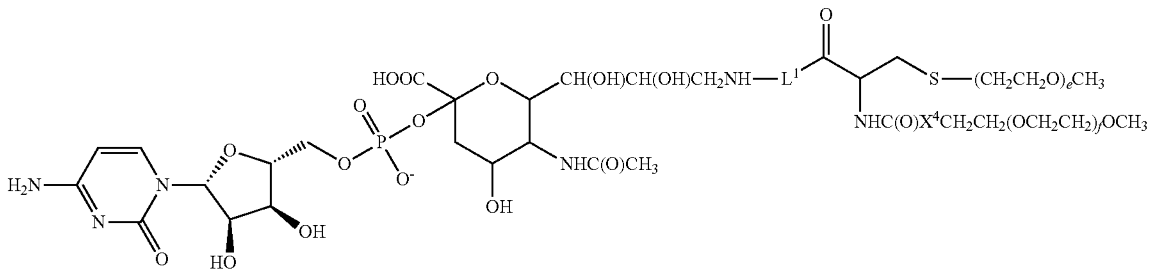

in which $X^4$ is O or a bond.

The invention also provides for the use of sugar nucleotides modified with L-$R^1$ at the 6-carbon position. Exemplary species according to this embodiment include:

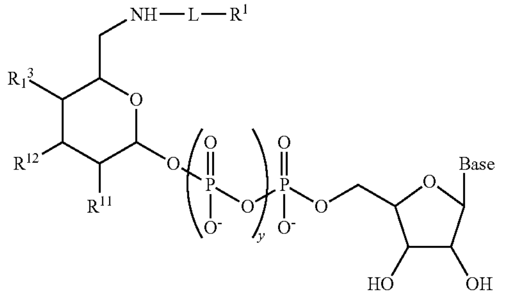

in which the R groups, and L, represent moieties as discussed above. The index "y" is 0, 1 or 2. In an exemplary embodiment, L is a bond between NH and $R^1$. The base is a nucleic acid base.

Exemplary nucleotide sugars of use in the invention in which the carbon at the 6-position is modified include species having the stereochemistry of GDP mannose, e.g.:

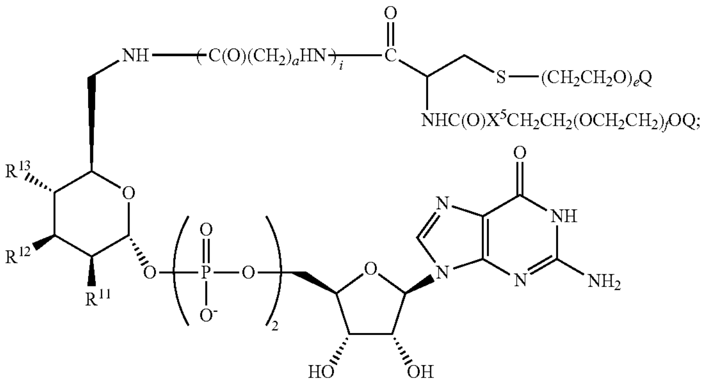

and

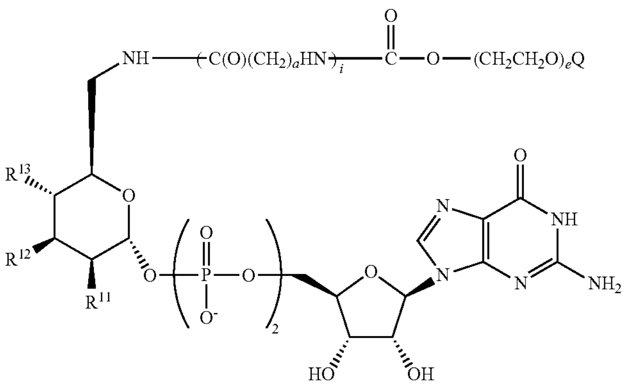

in which $X^5$ is a bond or O. The index i represents 0 or 1. The index a represents an integer from 1 to 20. The indices e and f independently represent integers from 1 to 2500. Q, as discussed above, is H or substituted or unsubstituted $C_1$-$C_6$ alkyl. As those of skill will appreciate, the serine derivative, in which S is replaced with O also falls within this general motif.

In a still further exemplary embodiment, the invention provides a conjugate in which the modified sugar is based on the stereochemistry of UDP galactose. An exemplary nucleotide sugar of use in this invention has the structure:

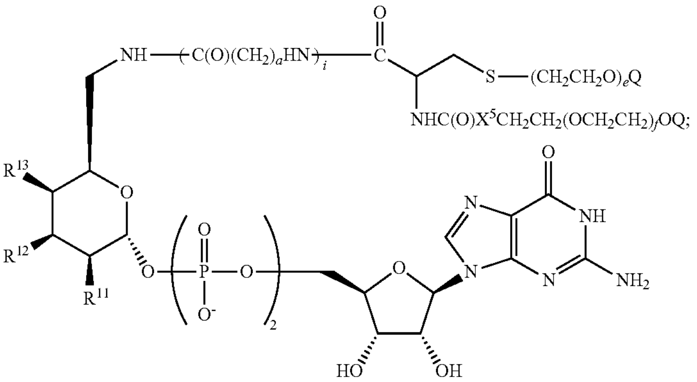

and

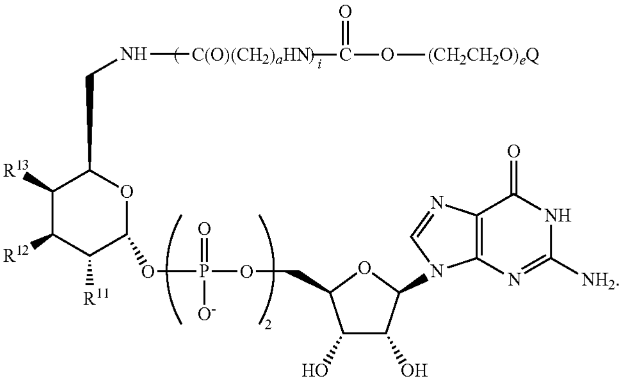

In another exemplary embodiment, the nucleotide sugar is based on the stereochemistry of glucose. Exemplary species according to this embodiment have the formulae:

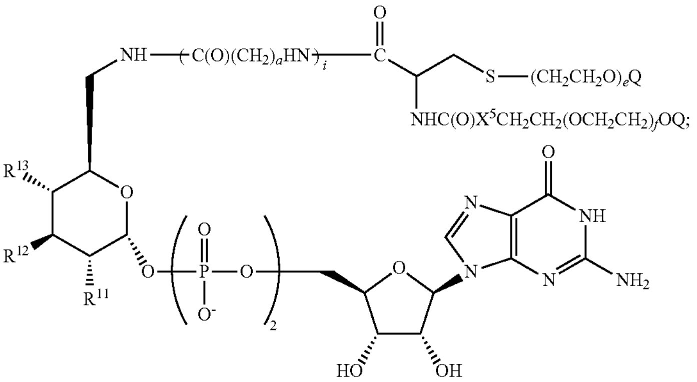

and

-continued

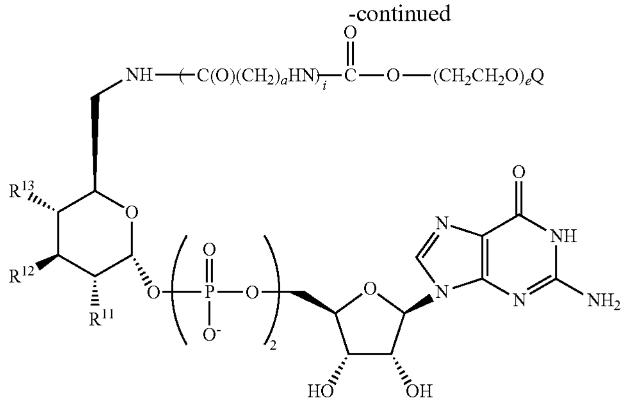

In general, the sugar moiety or sugar moiety-linker cassette and the PEG or PEG-linker cassette groups are linked together through the use of reactive groups, which are typically transformed by the linking process into a new organic functional group or unreactive species. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups pendent from a sugar nucleus or modifying group include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., Protective Groups in Organic Synthesis, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., *Curr. Med. Chem.* 6: 93 (1999); and Schafer et al., *J. Org. Chem.* 65: 24 (2000)).

In an exemplary embodiment, the modified sugar is based upon a 6-amino-N-acetyl-glycosyl moiety. As shown below for N-acetylgalactosamine, the 6-amino-sugar moiety is readily prepared by standard methods.

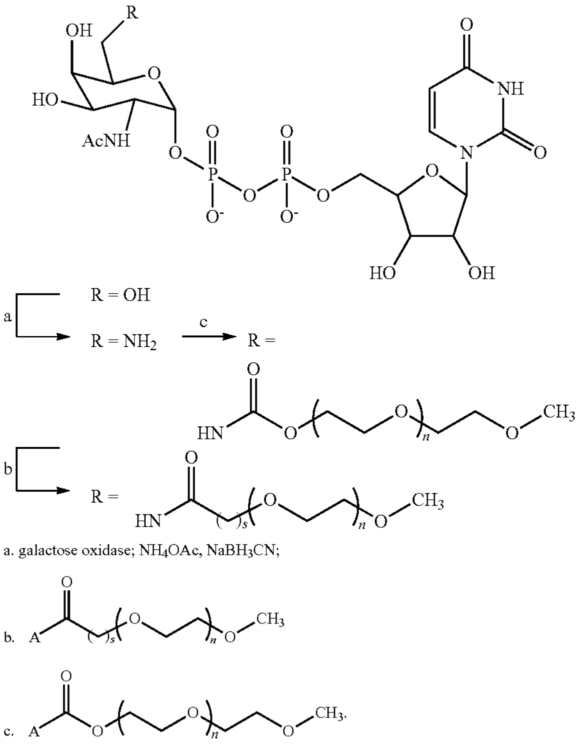

In the scheme above, the index n represents an integer from 1 to 2500. In an exemplary embodiment, this index is selected such that the polymer is about 10 kD, 15 kD or 20 kD in molecular weight. The symbol “A” represents an activating group, e.g., a halo, a component of an activated ester (e.g., a N-hydroxysuccinimide ester), a component of a carbonate (e.g., p-nitrophenyl carbonate) and the like. Those of skill in the art will appreciate that other PEG-amide nucleotide sugars are readily prepared by this and analogous methods.

The acceptor peptide is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more N- or O-linked glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Those of skill will appreciate that the invention can be practiced using substantially any peptide or glycopeptide from any source. Exemplary peptides with which the invention can be practiced are set forth in WO 03/031464, and the references set forth therein.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to the hydroxy side chain of a hydroxyamino acid, preferably serine or threonine, although unusual or non-natural amino acids, e.g., 5-hydroxyproline or 5-hydroxylysine may also be used.

Moreover, in addition to peptides, the methods of the present invention can be practiced with other biological structures (e.g., glycolipids, lipids, sphingoids, ceramides, whole cells, and the like, containing a glycosylation site).

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

Exemplary peptides with which the present invention can be practiced, methods of adding or removing glycosylation sites, and adding or removing glycosyl structures or substructures are described in detail in WO03/031464 and related U.S. and PCT applications.

The present invention also takes advantage of adding to (or removing from) a peptide one or more selected glycosyl residues, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. An exemplary chemical deglycosylation is brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

In an exemplary embodiment, the peptide is essentially completely desialylated with neuraminidase prior to performing glycoconjugation or remodeling steps on the peptide. Following the glycoconjugation or remodeling, the peptide is optionally re-sialylated using a sialyltransferase. In an exemplary embodiment, the re-sialylation occurs at essentially each (e.g., >80%, preferably greater than 85%, greater than 90%, preferably greater than 95% and more preferably greater than 96%, 97%, 98% or 99%) terminal saccharyl acceptor in a population of sialyl acceptors. In a preferred embodiment, the saccharide has a substantially uniform sialylation pattern (i.e., substantially uniform glycosylation pattern).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation, and sites for O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC Crit. Rev. Biochem., pp. 259-306 (1981).

In one embodiment, the invention provides a method for linking two or more peptides through a linking group. The linking group is of any useful structure and may be selected from straight- and branched-chain structures. Preferably, each terminus of the linker, which is attached to a peptide, includes a modified sugar (i.e., a nascent intact glycosyl linking group).

In an exemplary method of the invention, two peptides are linked together via a linker moiety that includes a polymeric (e.g., PEG linker). The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosyl units, respectively. In practice, the $(glycosyl)^1$-PEG-$(glycosyl)^2$ linker is contacted with the first peptide and a first transferase for which the first glycosyl unit is a substrate, thereby forming $(peptide)^1$-$(glycosyl)^1$-PEG-$(glycosyl)^2$. Transferase and/or unreacted peptide is then optionally removed from the reaction mixture. The second peptide and a second transferase for which the second glycosyl unit is a substrate are added to the (peptide)-$(glycosyl)^1$-PEG-$(glycosyl)^2$ conjugate, forming (peptide)-$(glycosyl)^1$-PEG-$(glycosyl)^2$-$(peptide)^2$; at least one of the glycosyl residues is either directly or indirectly O-linked. Those of skill in the art will appreciate that the method outlined above is also applicable to forming conjugates between more than two peptides by, for example, the use of a branched PEG, dendrimer, poly(amino acid), polysaccharide or the like.

In an exemplary embodiment, the peptide that is modified by a method of the invention is a glycopeptide that is produced in mammalian cells (e.g., CHO cells) or in a transgenic animal and thus, contains N- and/or O-linked oligosaccharide chains, which are incompletely sialylated. The oligosaccharide chains of the glycopeptide lacking a sialic acid and containing a terminal galactose residue can be PEGylated, PPGylated or otherwise modified with a modified sialic acid.

In Scheme 1, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG attachment by reacting compound 3 with an activated PEG or PPG derivative (e.g., PEG-C(O)NHS, PEG-OC(O)O-p-nitrophenyl), producing species such as 4 or 5, respectively.

Scheme 1

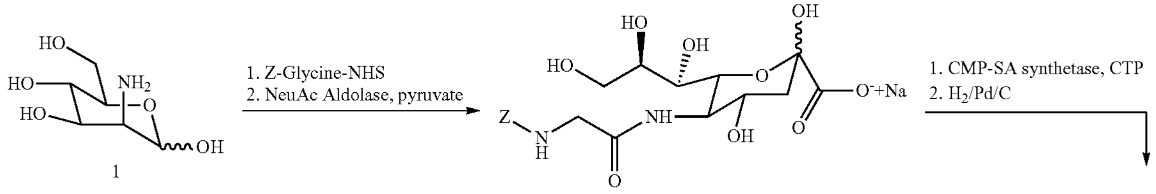

1

2

-continued

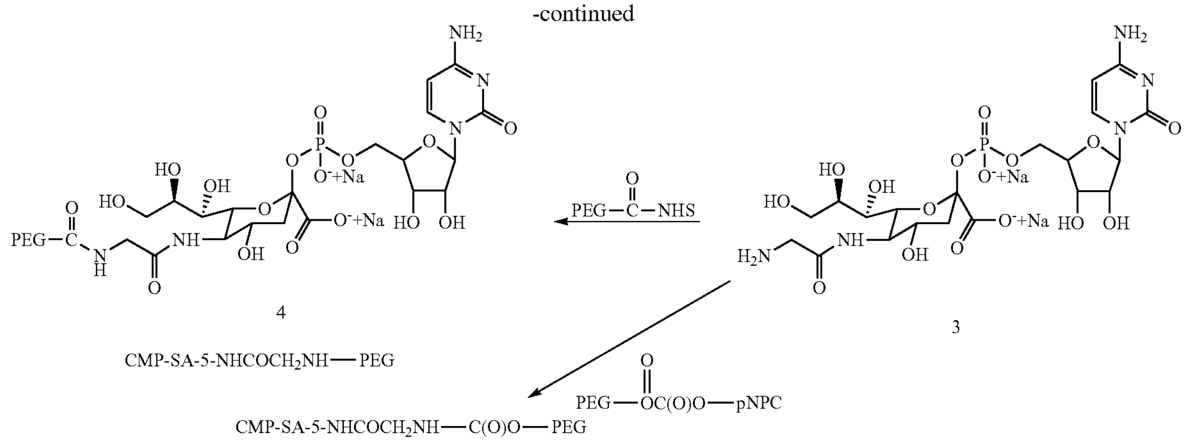

4 3 5

Conjugation of Modified Sugars to Peptides

The PEG modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), U.S. Pat. Nos. 5,352,670, 5,374,541, 5,545,553, commonly owned U.S. Pat. Nos. 6,399,336, and 6,440,703, and commonly owned published PCT applications, WO 03/031464, WO 04/033651, WO 04/099231, which are incorporated herein by reference.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

In another embodiment, the method makes use of one or more exo- or endoglycosidase. The glycosidase is typically a mutant, which is engineered to form glycosyl bonds rather than rupture them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or mono-saccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 37° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few h, with recoverable amounts usually being obtained within 24 h or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. As used herein, an industrial scale generally produces at least one gram of finished, purified conjugate.

In the discussion that follows, the invention is exemplified by the conjugation of modified sialic acid moieties to a glycosylated peptide. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other PEG moieties, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

In an exemplary embodiment, an acceptor for a sialyltransferase is present on the peptide to be modified either as a naturally occurring structure or it is placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)). Exemplary sialyltransferases are set forth herein, see, e.g., FIG. 9.

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GlcNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions. In another embodiment of this method, the sialic acid moieties of the peptide are essentially completely removed (e.g., at least 90, at least 95 or at least 99%), exposing an acceptor for a modified sialic acid.

In the discussion that follows, the method of the invention is exemplified by the use of modified sugars having a PEG moiety attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment of the invention in which a carbohydrate residue is "trimmed" prior to the addition of the modified sugar high mannose is trimmed back to the first generation biantennary structure. A modified sugar bearing a PEG moiety is conjugated to one or more of the sugar residues exposed by the "trimming back." In one example, a PEG moiety is added via a GlcNAc moiety conjugated to the PEG moiety. The modified GlcNAc is attached to one or both of the terminal mannose residues of the biantennary structure. Alternatively, an unmodified GlcNAc can be added to one or both of the termini of the branched species.

In another exemplary embodiment, a PEG moiety is added to one or both of the terminal mannose residues of the biantennary structure via a modified sugar having a galactose residue, which is conjugated to a GlcNAc residue added onto the terminal mannose residues. Alternatively, an unmodified Gal can be added to one or both terminal GlcNAc residues.

In yet a further example, a PEG moiety is added onto a Gal residue using a modified sialic acid such as those discussed above.

In another exemplary embodiment, a high mannose structure is "trimmed back" to the mannose from which the biantennary structure branches. In one example, a PEG moiety is added via a GlcNAc modified with the polymer. Alternatively, an unmodified GlcNAc is added to the mannose, followed by a Gal with an attached PEG moiety. In yet another embodiment, unmodified GlcNAc and Gal residues are sequentially added to the mannose, followed by a sialic acid moiety modified with a PEG moiety.

A high mannose structure can also be trimmed back to the elementary tri-mannosyl core.

In a further exemplary embodiment, high mannose is "trimmed back" to the GlcNAc to which the first mannose is attached. The GlcNAc is conjugated to a Gal residue bearing a PEG moiety. Alternatively, an unmodified Gal is added to the GlcNAc, followed by the addition of a sialic acid modified with a water-soluble sugar. In yet a further example, the terminal GlcNAc is conjugated with Gal and the GlcNAc is subsequently fucosylated with a modified fucose bearing a PEG moiety.

High mannose may also be trimmed back to the first GlcNAc attached to the Asn of the peptide. In one example, the GlcNAc of the GlcNAc-$(Fuc)_a$ residue is conjugated with a GlcNAc bearing a water soluble polymer. In another example, the GlcNAc of the GlcNAc-$(Fuc)_a$ residue is modified with Gal, which bears a water soluble polymer. In a still further embodiment, the GlcNAc is modified with Gal, followed by conjugation to the Gal of a sialic acid modified with a PEG moiety.

Other exemplary embodiments are set forth in commonly owned U.S. Patent application Publications: 20040132640; 20040063911; 20040137557; U.S. patent application Ser. Nos. 10/369,979; 10/410,913; 10/360,770; 10/410,945 and PCT/US02/32263 each of which is incorporated herein by reference.

The Examples set forth above provide an illustration of the power of the methods set forth herein. Using the methods described herein, it is possible to "trim back" and build up a carbohydrate residue of substantially any desired structure.

The modified sugar can be added to the termini of the carbohydrate moiety as set forth above, or it can be intermediate between the peptide core and the terminus of the carbohydrate.

In an exemplary embodiment, an existing sialic acid is removed from a glycopeptide using a sialidase, thereby unmasking all or most of the underlying galactosyl residues. Alternatively, a peptide or glycopeptide is labeled with galactose residues, or an oligosaccharide residue that terminates in a galactose unit. Following the exposure of or addition of the galactose residues, an appropriate sialyltransferase is used to add a modified sialic acid.

In another exemplary embodiment, an enzyme that transfers sialic acid onto sialic acid is utilized. This method can be practiced without treating a sialylated glycan with a sialidase to expose glycan residues beneath the sialic acid. An exemplary polymer-modified sialic acid is a sialic acid modified with poly(ethylene glycol). Other exemplary enzymes that add sialic acid and modified sialic acid moieties onto sialic acid residues of a glycan or exchange an existing sialic acid residue on a glycan for these species include ST3Gal3, CST-II, ST8Sia-II, ST8Sia-III and ST8Sia-IV.

In yet a further approach, a masked reactive functionality is present on the sialic acid. The masked reactive group is preferably unaffected by the conditions used to attach the modified sialic acid to the erythropoietin. After the covalent attachment of the modified sialic acid to the peptide, the mask is removed and the peptide is conjugated with an agent such as PEG. The agent is conjugated to the peptide in a specific manner by its reaction with the unmasked reactive group on the modified sugar residue.

Any modified sugar can be used with its appropriate glycosyltransferase, depending on the terminal sugars of the oligosaccharide side chains of the glycopeptide. As discussed above, the terminal sugar of the glycopeptide required for introduction of the PEGylated structure can be introduced naturally during expression or it can be produced post expression using the appropriate glycosidase(s), glycosyltransferase(s) or mix of glycosidase(s) and glycosyltransferase(s).

In a further exemplary embodiment, UDP-galactose-PEG is reacted with β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GNT1-5, is utilized to transfer PEGylated-GlcNAc to a terminal mannose residue on a glycopeptide. In a still further exemplary embodiment, an the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG-galactose functionality onto the exposed GlcNAc.

In an alternative embodiment, the modified sugar is added directly to the peptide backbone using a glycosyltransferase known to transfer sugar residues to the peptide backbone. Exemplary glycosyltransferases useful in practicing the present invention include, but are not limited to, GalNAc transferases (GalNAc T1-14), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

Enzymes and reaction conditions for preparing the conjugates of the present invention are discussed in detail in the parent of the instant application as well as co-owned published PCT patent applications WO 03/031464, WO 04/033651, WO 04/099231.

In a selected embodiment, set forth in Example 2, an EPO peptide, expressed in insect cells, is remodeled such that glycans on the remodeled glycopeptide include a GlcNAc-Gal glycosyl residue. The addition of GlcNAc and Gal can occur as separate reactions or as a single reaction in a single vessel. In this example, GlcNAc-transferase I and Gal-transferase I are used. The modified sialyl moiety is added using ST3Gal-III.

In another embodiment, as illustrated in Example 3, the addition of GlcNAc, Gal and modified Sia can also occur in a single reaction vessel, using the enzymes set forth above. Example 4 sets forth a method in which each of the enzymatic remodeling and glycoPEGylation steps are carried out individually.

When the peptide is expressed in mammalian cells, different methods are of use. In Example 5, the peptide is conjugated without need for remodeling prior to conjugation by contacting the peptide with a sialyltransferase that transfers the modified sialic acid directly onto a sialic acid on the peptide forming Sia-Sia-L-$R^1$, or exchanges a sialic acid on the peptide for the modified sialic acid, forming Sia-L-$R^1$. An exemplary enzyme of use in this method is CST-II. Other enzymes that add sialic acid to sialic acid are known to those of skill in the art and examples of such enzymes are set forth in FIG. 9.

Another method of preparing the conjugates of the invention is set forth in Example 6. The peptide expressed in a mammalian system is desialylated using a sialidase. The exposed Gal residue is sialylated with a modified sialic acid using a sialyltransferase specific for O-linked glycans, providing an EPO peptide with an O-linked modified glycan. The desialylated, modified EPO peptide is optionally partially or fully re-sialylated by using a sialyltransferase such as ST3GalIII.

In another aspect, the invention provides a method of making a PEGylated erythropoietin of the invention. The method includes: (a) contacting a substrate erythropoietin peptide comprising a glycosyl group selected from:

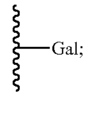

and

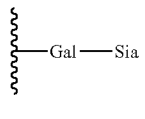

with a PEG-sialic acid donor having the formula:

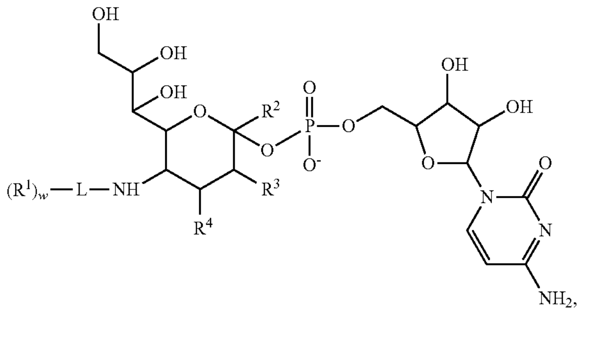

and an enzyme that transfers PEG-sialic acid from said donor onto a member selected from the Gal and the Sia of said glycosyl group, under conditions appropriate for said transfer. An exemplary modified sialic acid donor is CMP-sialic acid modified, through a linker moiety, with a polymer, e.g., a straight chain or branched poly(ethylene glycol) moiety.

In an exemplary embodiment, the PEG-sialic acid donor has the formula:

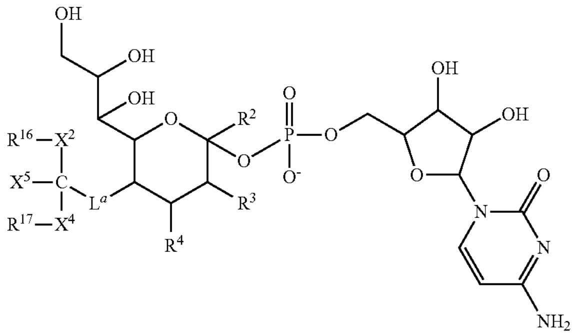

In another exemplary embodiment, the PEG-sialic acid donor has the formula:

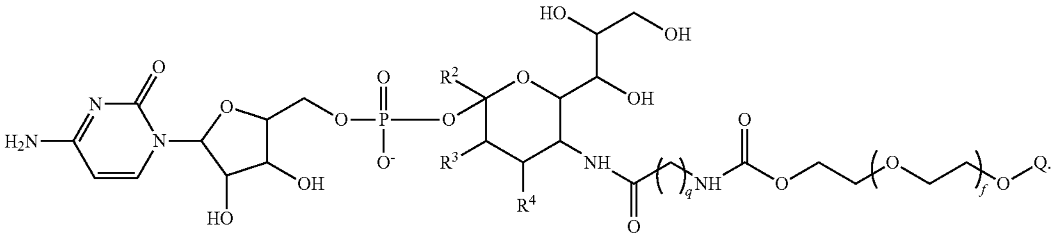

In a further exemplary embodiment, the EPO peptide is expressed in an appropriate expression system prior to being glycopegylated or remodeled. Exemplary expression systems include Sf-9/baculovirus and Chinese Hamster Ovary (CHO) cells.

Purification of Erythropoietin Conjugates

The products produced by the above processes can be used without purification. However, it is usually preferred to recover the product and one or more of the intermediates, e.g., nucleotide sugars, branched and linear PEG species, modified sugars and modified nucleotide sugars. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

If the peptide is produced intracellularly, as a first step, the particulate debris, either host cells or lysed fragments, is removed. Following glycoPEGylation, the PEGylated peptide is purified by art-recognized methods, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration, using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps. Additionally, the modified glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics or preservatives may be included to prevent the growth of adventitious contaminants.

Within another embodiment, supernatants from systems which produce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Other methods of use in purification include size exclusion chromatography (SEC), hydroxyapatite chromatography, hydrophobic interaction chromatography and chromatography on Blue Sepharose. These and other useful methods are illustrated in co-assigned U.S. Provisional Patent Application No. 60/678,822, filed May 6, 2005.

One or more RP-HPLC steps employing hydrophobic RP-HPLC media, e.g., silica gel having pendant methyl or other aliphatic groups, may be employed to further purify a polypeptide conjugate composition. Some or all of the foregoing purification steps, in various combinations, can also be employed to provide a homogeneous or essentially homogeneous modified glycoprotein.

The modified glycopeptide of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

In an exemplary embodiment, the purification is accomplished by the methods set forth in commonly owned, co-assigned U.S. Provisional Patent Application No. 60/678,822, filed May 6, 2005.

Pharmaceutical Compositions

In another aspect, the invention provides a pharmaceutical composition. The pharmaceutical composition includes a pharmaceutically acceptable diluent and a covalent conjugate between a non-naturally-occurring, PEG moiety, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235, 871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

The active ingredient used in the pharmaceutical compositions of the present invention is glycoPEGylated erythropoietin and its derivatives having the biological properties of causing bone marrow cells to increase production of reticulocytes and red blood cells.

The formulation of the present invention is useful as a parenteral formulation in treating blood disorders characterized by low or defective red blood cell production such as various forms of anemia, including anemias associated with chronic renal failure, zidovidine treated HIV infected patients, and cancer patients on chemotherapy. It may also have application in the treatment of a variety of disease states, disorders and states of hematologic irregularity such as sickle cell disease, beta-thalassemia, cystic fibrosis, pregnancy and menstrual disorders, early anemia of prematurity, spinal cord injury, space flight, acute blood loss, aging and the like. Preferably, the EPO composition of the present invention is administered parenterally (e.g. IV, IM, SC or IP). Effective dosages are expected to vary considerably depending on the condition being treated and the route of administration but are expected to be in the range of about 0.1 (~7 U) to 100 (~7000 U) μg/kg body weight of the active material. Preferable doses for treatment of anemic conditions are about 50 to about 300 Units/kg three times a week. Because the present invention provides an erythropoietin with an enhanced in vivo residence time, the stated dosages are optionally lowered when a composition of the invention is administered.

In another embodiment, the invention provides a method of treating a tissue injury in a subject in need thereof. Exemplary injuries include those characterized by damage resulting from ischemia, trauma, inflammation or contact with toxic substances. The method includes the step of administering to the subject an amount of a polymer-modified erythropoietin peptide of the invention effective to ameliorate the tissue injury in the subject. An exemplary class of protection or treatment includes neuroprotection (e.g., treatment of stroke, Alzheimer's, Parkinson's and other degenerative neurological disorders). Methods of using EPO for tissue protection are known in the art. See for example, U.S. Pat. No. 6,531,121. The modified EPO of the invention is also of use in treating patients with diseases such as compromised kidney function, cancer, and retinopathy. In a further exemplary embodiment, the EPO peptide of use in the methods is non-erythropoietically or essentially non-erythropoietically active peptide.

Preparative methods for species of use in preparing the compositions of the invention are generally set forth in various patent publications, e.g., US 20040137557; WO 04/083258; and WO 04/033651. The following examples are provided to illustrate the conjugates, and methods and of the present invention, but not to limit the claimed invention.

EXAMPLES

Example 1

Preparation of Cysteine-$PEG_2$ (2)

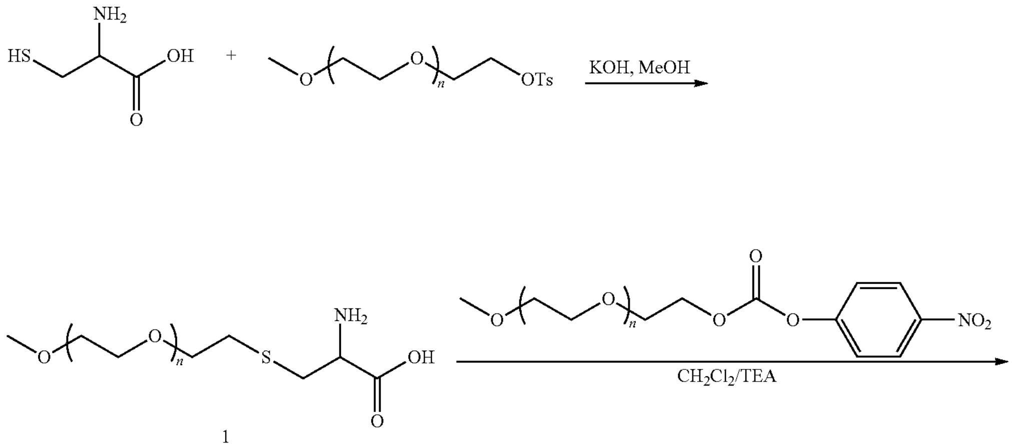

1

-continued

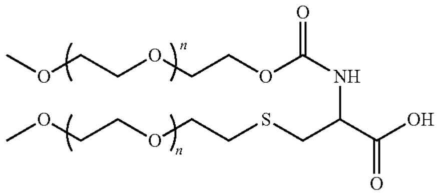

2

1.1 Synthesis of Compound 1

Potassium hydroxide (84.2 mg, 1.5 mmol, as a powder) was added to a solution of L-cysteine (93.7 mg, 0.75 mmol) in anhydrous methanol (20 L) under argon. The mixture was stirred at room temperature for 30 min, and then mPEG-O-tosylate of molecular mass 20 kilodalton (Ts; 1.0 g, 0.05 mmol) was added in several portions over 2 h. The mixture was stirred at room temperature for 5 days, and concentrated by rotary evaporation. The residue was diluted with water (30 mL), and stirred at room temperature for 2 h to destroy any excess 20 kilodalton mPEG-O-tosylate. The solution was then neutralized with acetic acid, the pH adjusted to pH 5.0 and loaded onto a reversed phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 mL, hydroxide form; gradient of water to water/acetic acid-0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 453 mg (44%) of a white solid (1). Structural data for the compound were as follows: $^1$H-NMR (500 MHz; $D_2O$) δ 2.83 (t, 2H, O—C—$CH_2$—S), 3.05 (q, 1H, S—CHH—CHN), 3.18 (q, 1H, (q, 1H, S—C HH—CHN), 3.38 (s, 3H, $CH_3O$), 3.7 (t, $OCH_2CH_2O$), 3.95 (q, 1H, CHN). The purity of the product was confirmed by SDS PAGE.

1.2 Synthesis of Compound 2 (Cysteine-$PEG_2$)

Triethylamine (~0.5 mL) was added dropwise to a solution of compound 1 (440 mg, 22 μmol) dissolved in anhydrous $CH_2Cl_2$ (30 mL) until the solution was basic. A solution of 20 kilodalton mPEG-O-p-nitrophenyl carbonate (660 mg, 33 μmol) and N-hydroxysuccinimide (3.6 mg, 30.8 μmol) in $CH_2Cl_2$ (20 mL) was added in several portions over 1 hour at room temperature. The reaction mixture was stirred at room temperature for 24 h. The solvent was then removed by rotary evaporation, the residue was dissolved in water (100 mL), and the pH adjusted to 9.5 with 1.0 N NaOH. The basic solution was stirred at room temperature for 2 h and was then neutralized with acetic acid to a pH 7.0. The solution was then loaded onto a reversed phase chromatography (C-18 silica) column. The column was eluted with a gradient of methanol/water (the product elutes at about 70% methanol), product elution monitored by evaporative light scattering, and the appropriate fractions collected and diluted with water (500 mL). This solution was chromatographed (ion exchange, XK 50 Q, BIG Beads, 300 mL, hydroxide form; gradient of water to water/acetic acid-0.75N) and the pH of the appropriate fractions lowered to 6.0 with acetic acid. This solution was then captured on a reversed phase column (C-18 silica) and eluted with a gradient of methanol/water as described above. The product fractions were pooled, concentrated, redissolved in water and freeze-dried to afford 575 mg (70%) of a white solid (2). Structural data for the compound were as follows: $^1$H-NMR (500 MHz; $D_2O$) δ 2.83 (t, 2H, O—C—$CH_2$—S), 2.95 (t, 2H, O—C—$CH_2$—S), 3.12 (q, 1H, S—CHH—CHN), 3.39 (s, 3H $CH_3O$), 3.71 (t, $OCH_2CH_2O$). The purity of the product was confirmed by SDS PAGE.

Example 2

The following examples detail methods of modifying an EPO peptide that is expressed in insect cells.

GnT1 and GalT1 Reaction in One Pot 2.1 Reaction in One Pot

The one pot GlcNAc transferase-1 and galactose transferase-1 reaction was carried out by incubating insect-derived EPO (1 mg/mL) in 100 mM Tris HCl pH 7.5 or MES pH 6.5 containing 150 mM NaCl, 5 mM UDP-GlcNAc, 5 mM UDP-Gal, 5 mM $MnCl_2$, 0.02% sodium azide, 30 mU/mL of purified GlcNAc transferase-1 and 200 mU/mL of purified galactose transferase-1 at 32° C. for 16 h.

2.2 Purification of EPO on Superdex75

A Superdex 75 column was equilibrated in 100 mM MES buffer pH 6.5 containing 150 mM NaCl at a flow rate of 5 mL/min. The EPO product from step 2.1 (above) was loaded on to the column and eluted with the equilibration buffer. The eluate was monitored for absorbance at 280 nm and conductivity. SDS-PAGE was used to determine which pooled peak fractions contains the EPO and used in further experiments.

2.3 ST3Gal-III Reaction

The ST3GalIII reaction was carried out by incubating 1 mg/mL EPO-Gal (from step 2.2, above) in 100 mM Tris HCl pH 7.5 or MES pH 6.5 containing 150 mM NaCl, 0.5 mM CMP-N-acetyl-neuraminic acid-20 kilodalton-PEG, 0.02% sodium azide, and 200 mU/mL of purified ST3Gal-III at 32° C. for 16 h.

Example 3

GnT1, GalT1 and ST3Gal-III (Using CMP-NAN-20KPEG) Reaction in One Pot

EPO (1 mg/mL), expressed in insect cells, was incubated with 30 mU/mL of GlcNAc transferase-1, 200 mU/mL of galactose transferase-1 and 500 mU/mL of ST3GalIII with sugar nucleotides and CMP-N-acetyl-neuraminic acid-20 Kd PEG in 100 mM MES buffer pH 6.5 and analyzed using SDS-PAGE. Similar to the results obtained in the two-step enzyme remodeling reactions, three bands of PEGylated EPO are seen in the one-pot, three enzyme preparations.

Example 4

Production of Biantennary PEG-EPO 4.1 Addition of GlcNAc to rEPO

Recombinant EPO, expressed in insect cells (1 mg/mL) in 0.1 M Tris, 0.15 M NaCl, 5 mM $MnCl_2$ and 0.02% sodium azide at pH 7.2 was incubated with 3 mM USP-GlcNAc, 50 mU/mg GlcNAc transferase-1 and 50 mU/mg GlcNAc transferase-II at 32° C. for 24 h.

4.2 Addition of Galactose

To the GlcNAc-labeled peptide of step 8.1 (above) was added 3 mM UDP-Gal and 0.2 U/mg galactose transferase-1. The mixture was incubated for 36 h at 32° C. The galactosylated product was isolated by gel filtration chromatography on a Superdex 75 column in Tris-buffered saline. The purified product was concentrated to 1 mg/mL.

4.3 Addition of Sialic Acid or Sialic Acid PEG

The galactosylated product from step 4.2 (above) (1 mg/mL) in 0.1 M Tris, 0.1M NaCl at pH 7.2 was incubated at 32° C. for 24 h with 200 mU/mg ST3GalIII and 0.5 mM CMP-sialic acid or CMP-sialic acid-PEG (where the PEG has a molecular mass of 5 kDa, 10 kDa, 20 kDa or 30 kDa).

Example 5

N-Linked 30K PEGylation by CST-II

To EPO glycosylated as expressed in CHO (Chinese Hamster Ovary) cells (5 mg, 0.166 μmol, 5 mL) was concentrated and buffer exchanged with tris buffer (50 mM Tris, 0.15M NaCl, 0.001 M $CaCl_2$+0.005% $NaN_3$) to a final volume of 5 mL. Then CMP-sialic acid-PEG (30 kilodaltons, 25 mg, 0.833 μmol; see FIG. 3B for structure of 30 Kdalton CMP-sialic acid-PEG), 0.25 mL, 100 mM $MnCl_2$, 0.25 mL, and a bifunctional sialyltransferase from *Campylobacter jejuni*, CST-II (1.4 U/mL, 0.5 mL, 0.7 U), were added. The resulting mixture was rocked at 32° C. for 48 h.

At the conclusion of the reaction, the mixture was concentrated by ultrafitration to 1 mL final volume, and was then buffer exchanged with 25 mM NaOAc+0.005% Tween-80 (pH 6.0) to 2.5 mL. Q-Sepharose IEX chromatography was performed using 25 mM NaOAc+2M NaCl+0.005% Tween-80 (pH 6.0) as eluent. Peak 2 was collected and concentrated to 1.5 mL by ultrafiltration, then subjected to superdex-200 purification (column: Superdex 200, 16/60 GL, Amersham) using 1×PBS (pH 5.5+0.005% Tween80) as eluent. Peak 2 was collected and concentrated to 1.5 mL. This resulting material was sterile filtered and formulated to a final volume of 2.5 mL using 10 mM NaOAc (0.75% NaCl, pH 5.5). Protein concentration 264 μg/mL; 660 μg protein was obtained (BCA determination).

Example 6

The following example illustrates a method for preparing O-linked 40 kilodalton PEG linked EPO using ST3GalIII.

6.1 Desialylation

In this step EPO grown in Chinese Hamster Ovary cells (CHO cells), was desialylated. The GalNAc-Gal linkage serves as an acceptor for transfer of the modified sialic acid PEG in step 6.2, below.

EPO solution 10 mL (10 mg, 0.33 μmol) glycosylated as expressed in CHO (Chinese Hamster Ovary) cells, was buffer exchanged with Tris buffer (20 mM Tris, 50 mM NaCl, 5 mM $CaCl_2$, 0.02% $NaN_3$, pH 7.2) to give a final volume of 10 mL. Then 750 mU 2,3,6,8-neuramidase, from *Arthrobacter Ureafaciens*, was added to the solution. The resulting mixture was rocked at 32° C. for 48 h. The product of this step was used directly in the next step of the protocol (see below).

6.2 O-Linked 40K PEGylation

In this step ST3Gal2 is used to transfer a modified sialic acid-PEG moiety to the desialylated EPO from step 6.1, above.

CMP-sialic acid-PEG (40 kilodalton, 33 mg, 0.825 μmol; see FIG. 3A for the structure of 40 kilodalton CMP-SA-PEG), an O-glycan specific sialyltransferase (1.4 U/mL, 300 mU) (ST3GalII or ST3GalIII), and 0.25 mL of 100 mM $MnCl_2$ were added to half of the above mixture. This mixture was rocked at 32° C. for 48 h. After the 48 hour period, the reaction mixture was concentrated by ultrafiltration (MWCO 5K) to 2.8 mL, then buffer exchanged with 25 mM NaOAc+0.001% Tween-80, pH 6.0) to a final volume of 3 mL. The final product was ion exchange purified on SP (5 mL) three times (three injections, 1 mL each). PEGylated EPO (Peak 2) was collected and concentrated by ultrafiltration to a final volume of 2 mL for SEC purification. Purification on superdex 200 provided resolution of the desired protein: EPO-GlcNAc-Gal-SA-PEG (40K) for the final step of the reaction.

6.3 Terminal Sialylation of CHO-EPO-GalNAc-Gal-SA-PEG(40K)

In this step of the process sialic acid was added to the termini of glycosyl structures not bearing a modified sialic acid residue.

Combined PEGylated EPO (approximately 2 mg from the reaction in step, b above) was concentrated by ultrafiltration (MWCO 5K) and then buffer exchanged with tris buffer (0.05M Tris, 0.15 M NaCl, 0.001 M $CaCl_2$+0.005% $NaN_3$) to a final volume of 2 mL. Then CMP-N-acetyl neuraminic acid (CMP-NANA; 1.5 mg, 2.4 μmol), ST3GalIII (8.9 U/mL, 10 μl, 0.089 U) and 50 μl of 100 mM $MnCl_2$ were added. The resulting mixture was rocked at 32° C. for 24 h, then concentrated to 1 mL final volume. This solution was directly subjected to Superdex 200 purification using 1×PBS (pH 5.5+0.005% Tween 80) as eluent. Peak 1 was collected and diluted to 10 mL. Protein concentration was 52.8 ug/mL (BCA). A total of 528 μg protein was obtained.

Example 7

In this example the pharmacokinetic profiles of intravenously-administered CHO-derived EPO and glycoPEGylated variants of the CHO-derived EPO were compared using an ELISA assay.

The pharmacokinetics of two non-PEGylated batches of CHO-derived EPO, a 30K PEGylated CHO-derived erythropoietin produced by methods of the invention, and 40K PEGylated CHO-derived Erythropoietin produced by methods of the invention, were compared by ELISA after a single 30 μg/kg intravenous dose into rats. The measurement followed accepted ELISA procedures using Europium detection.

7.1 Results

The Europium counts from the standard proteins from each plate were used to generate a standard linear regression curve and equation. The equation was used to convert the Europium count into the equivalent EPO quantity for each sample well.

Figure 6:
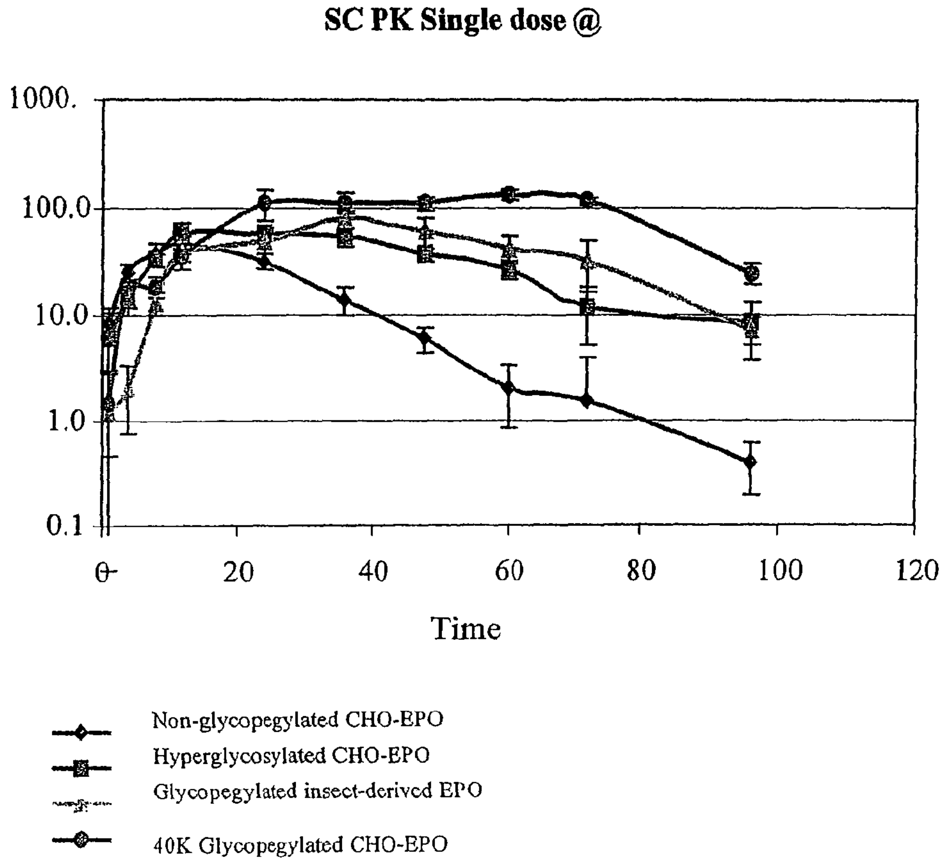
FIG. 6 shows the results of experiments comparing the pharmacokinetics of a CHO-derived non-glycoPEGylated EPO form, an insect-derived non-glycoPEGylated EPO form, with their corresponding glycoPEGylated forms.
Figure 7:
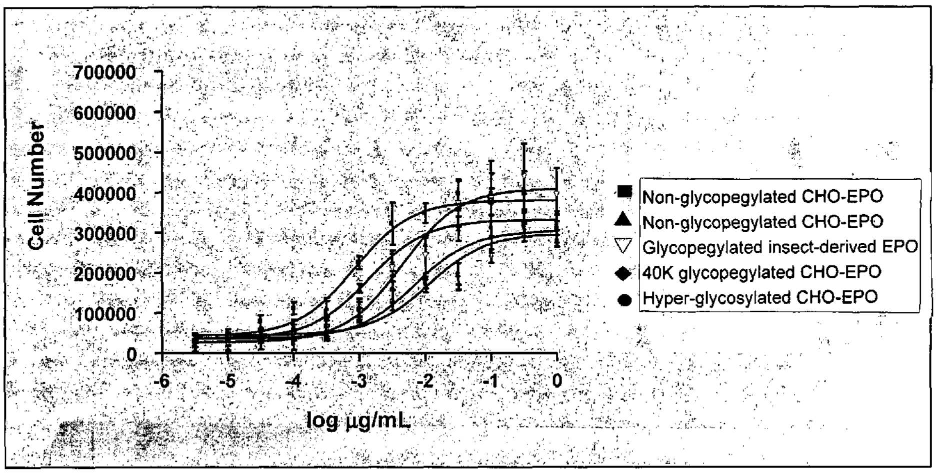
FIG. 7 shows the relative activities of two forms of non-glycoPEGylated EPO (A and B) versus two glycoPEGylated variants (the 30 kilodalton and 40 kilodalton variants of FIGS. 2A and 2B) and a hyperglycosylated EPO variant in stimulating proliferation of EPO receptor-bearing TF1 cells in culture.

The results are shown in FIG. 6. The limit of detection is approximately 0.4 ng/mL for non-PEGylated EPO, and approximately 0.8 ng/mL for both 30 kilodalton and 40 kilodalton PEGylated EPO.

Example 8

In this example the pharmacokinetic profiles of subcutaneously-administered CHO-derived erythropoietin (EPO), a hyperglycosylated non-glycoPEGylated EPO, an insect cell grown glycoPEGylated EPO, and a CHO cell derived glycoPEGylated EPO were determined using an ELISA assay.

Pharmacokinetics of a non-glycoPEGylated CHO-derived EPO, a non-PEGylated hyperglycosylated CHO derived EPO, a glycoPEGylated insect cell derived EPO; a 10K N-linked PEGylated insect cell-derived erythropoietin, and 40 kilodalton O-linked PEGylated CHO-derived erythropoietin were compared by ELISA after rats were given a single 10 μg/kg subcutaneous dose.

8.1 Pharmacokinetic Results.

Figure 8:
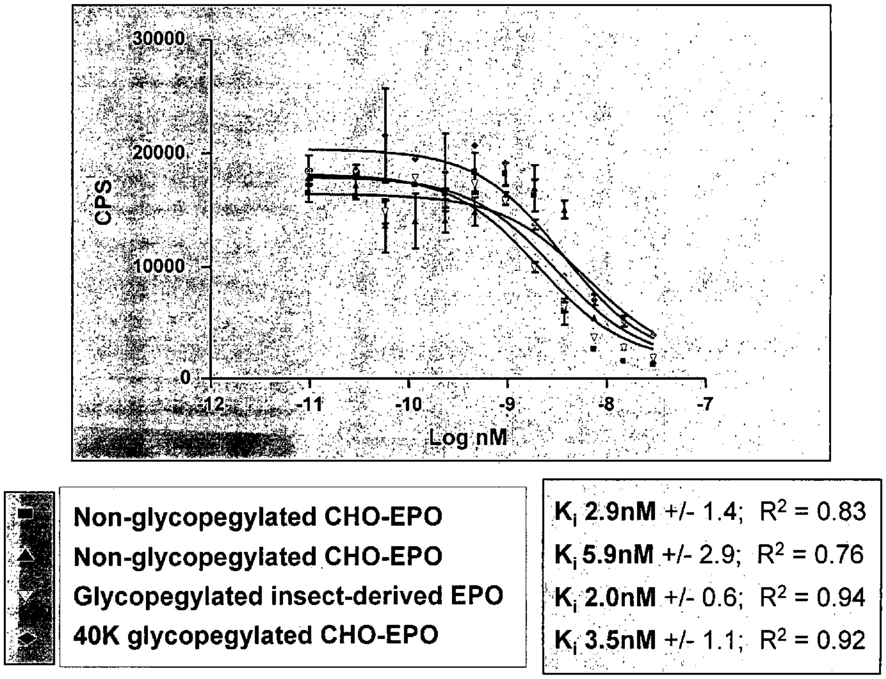
FIG. 8 shows inhibition of binding of isotope-labeled EPO to a recombinant chimeric EPO receptor by various concentrations of two non-pegylated EPO variants (A and B) and two glycoPEGylated variants (the 30 kilodalton and 40 kilodalton variants of FIGS. 2A and 2B).

Results of these experiments are shown in FIG. 8, which shows the average quantity of EPO in ng/mL and the standard deviations in the rat serum samples at different time points after injection$_{time=0\ hour}$ for each EPO variant group. The limit of detection is approximately 0.3 ng/mL for non-PEGylated EPO and PEGylated EPO.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An erythropoietin peptide comprising a glycosyl linking group attached to an amino acid residue of said peptide, said glycosyl linking group comprising a modified sialyl residue having the formula:

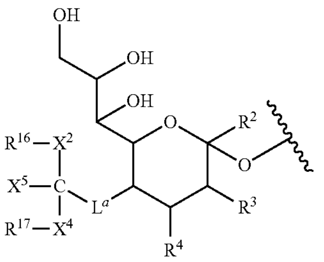

wherein $R^2$ is H, $CH_2OR^7$, $COOR^7$, $COO^-$, or $OR^7$, wherein $R^7$ represents H, substituted or unsubstituted alkyl, or substituted or unsubstituted heteroalkyl;

$R^3$ and $R^4$ are members independently selected from H, substituted or unsubstituted alkyl, $OR^8$, and $NHC(O)R^9$ wherein $R^8$ and $R^9$ are independently selected from H, substituted or unsubstituted alkyl, substituted or unsubstituted heteroalkyl, and sialic acid;

$L^a$ is a linker selected from C(O)NH and $(CH_2)_jC(O)NH(CH_2)_h(CONH)$, wherein h and j are integers independently selected from 0 to 10;

$R^{16}$ and $R^{17}$ are polymeric moieties independently selected from poly(amino) acids and PEG;

$X^2$ and $X^4$ are linkage fragments independently selected from S, SC(O)NH, HNC(O)S, SC(O)O, O, NH, NHC(O), (O)CNH, NHC(O)O, OC(O)NH, $CH_2S$, $CH_2O$, $CH_2CH_2O$, and $CH_2CH_2S$; and $X^5$ is a member selected from H, unsubstituted alkyl, and unsubstituted heteroalkyl.

2. The peptide according to claim 1, wherein said glycosyl linking group comprises a glycosyl group having the formula:

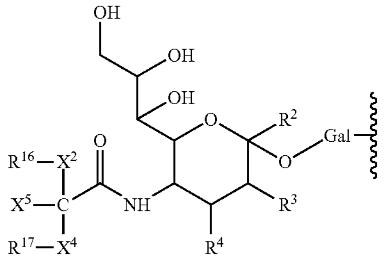

wherein $R^2$ is H, $CH_2OR^7$, $COOR^7$, $COO^-$, or $OR^7$, wherein $R^7$ represents H, substituted or unsubstituted alkyl, or substituted or unsubstituted heteroalkyl;

$R^3$ and $R^4$ are members independently selected from H, substituted or unsubstituted alkyl, $OR^8$, and $NHC(O)R^9$ wherein $R^8$ and $R^9$ are independently selected from H, substituted or unsubstituted alkyl, substituted or unsubstituted heteroalkyl, and sialic acid;

$R^{16}$ and $R^{17}$ are polymeric moieties independently selected from poly(amino) acids and PEG;

$X^2$ and $X^4$ are linkage fragments independently selected from S, SC(O)NH, HNC(O)S, SC(O)O, O, NH, NHC(O), (O)CNH, NHC(O)O, OC(O)NH, $CH_2S$, $CH_2O$, $CH_2CH_2O$, and $CH_2CH_2S$; and $X^5$ is a member selected from H, unsubstituted alkyl and unsubstituted heteroalkyl.

3. The peptide according to claim 2, wherein said glycosyl group has the formula:

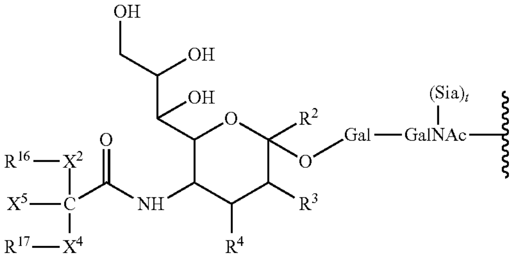

in which t is 0 or 1 wherein $R^2$ is H, $CH_2OR^7$, $COOR^7$, $COO^-$, or $OR^7$, wherein $R^7$ represents H, substituted or unsubstituted alkyl, or substituted or unsubstituted heteroalkyl;

$R^3$ and $R^4$ are members independently selected from H, substituted or unsubstituted alkyl, $OR^8$, and $NHC(O)R^9$ wherein $R^8$ and $R^9$ are independently selected from H, substituted or unsubstituted alkyl, substituted or unsubstituted heteroalkyl and sialic acid;

$R^{16}$ and $R^{17}$ are polymeric moieties independently selected from poly(amino) acids and PEG;

$X^2$ and $X^4$ are linkage fragments independently selected from S, SC(O)NH, HNC(O)S, SC(O)O, O, NH, NHC(O), (O)CNH, NHC(O)O, OC(O)NH, $CH_2S$, $CH_2O$, $CH_2CH_2O$, and $CH_2CH_2S$; and $X^5$ is a member selected from H, unsubstituted alkyl, and unsubstituted heteroalkyl.

4. The peptide according to claim 3, wherein said glycosyl linking group attached to said amino acid residue has the formula:

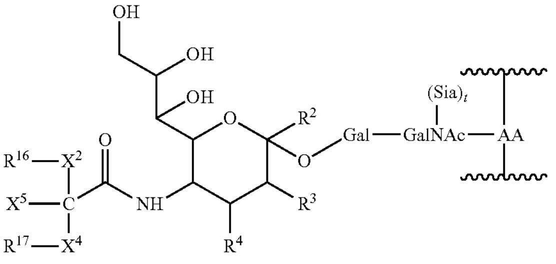

wherein

AA is an amino acid residue of said peptide.

5. The peptide according to claim 4, wherein said amino acid residue is a member selected from serine and threonine.

6. The peptide according to claim 5, wherein said peptide has the amino acid sequence of SEQ ID NO:1.

7. The peptide according to claim 6, wherein said amino acid residue is a serine at position 126 of SEQ ID NO:1.

8. The peptide according to claim 1, wherein said peptide comprises at least one said glycosyl linking group attached to an amino acid residue, said glycosyl linking group comprising a glycosyl group having a formula selected from:

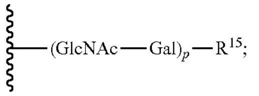

and

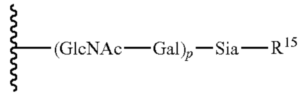

wherein $R^{15}$ is said modified sialyl residue; and p is an integer from 1 to 10.

9. The peptide according to claim 8, wherein said at least one glycosyl linking group attached to an amino acid residue of said peptide has a formula selected from:

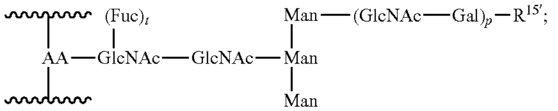

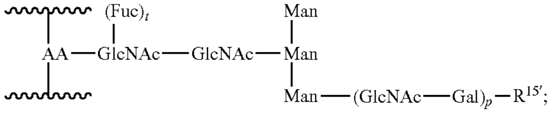

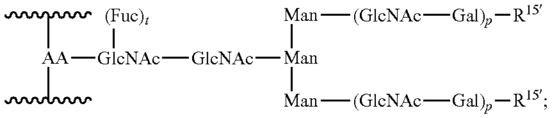

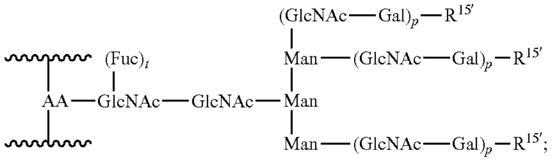

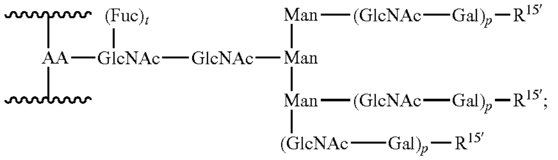

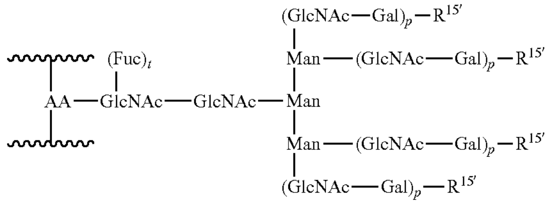

and combinations thereof wherein

AA is an amino acid residue of said peptide;

t is an integer equal to 0 or 1;

p is an integer from 1 to 10; and each $R^{15'}$ is a member independently selected from H, OH, sialic acid, said modified sialyl residue and Sia-$Sia^p$ wherein $Sia^p$ is said modified sialyl residue;

wherein at least one $R^{15'}$ is a member selected from said modified sialyl residue and Sia-$Sia^p$.

10. The peptide according to claim 9, wherein said amino acid residue is an asparagine residue.

11. The peptide according to claim 10, wherein said peptide has the amino acid sequence of SEQ ID NO:1, and wherein said amino acid residue is an asparagine residue which is a member selected from N24, N38, N83, and combinations thereof.

12. The peptide according to claim 11, wherein said glycosyl linking group is attached to N24.

13. The peptide according to claim 1, wherein said peptide is erythropoietically active.

14. The peptide according to claim 1, wherein said peptide is essentially non-erythropoietically active.

15. The peptide according to claim 14, wherein said peptide is tissue protective.

16. A method of preparing an erythropoietin peptide according to claim 1, said method comprising:

(a) contacting a substrate erythropoietin peptide comprising a glycosyl group selected from:

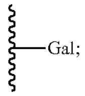

and

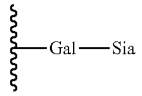

with a PEG-sialic acid donor having the formula:

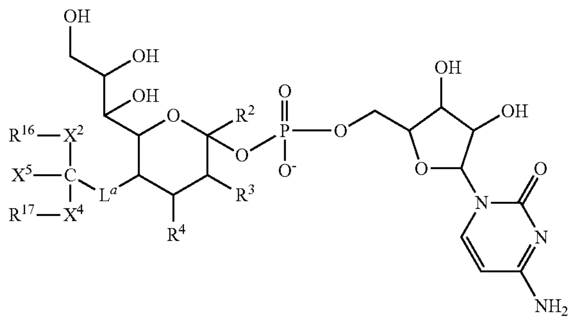

wherein $R^{16}$ and $R^{17}$ are independently selected poly (ethylene glycol) moieties, and an enzyme that transfers PEG-sialic acid from said donor onto a member selected from the Gal and the Sia of said glycosyl group, under conditions appropriate for said transfer.

17. The method of claim 16, further comprising, prior to step (a): (b) expressing said substrate erythropoietin peptide in a suitable host.

18. The method of claim 17, wherein said host is selected from an insect cell and a mammalian cell.

19. The method of claim 18, wherein said insect cell is a *Spodoptera frugiperda* cell.

20. The method of claim 18, wherein said mammalian cell is a Chinese Hamster Ovary cell.

21. A method of enhancing red blood cell production in a mammal, said method comprising administering to said mammal a peptide according to claim 1.

22. A method of treating a tissue injury in a subject in need thereof, said injury resulting from ischemia, trauma, inflammation or contact with toxic substances, said method comprising the step of administering to the subject an amount of an erythropoietin peptide according to claim 1, effective to ameliorate the damage associated with the tissue injury in said subject.

23. A pharmaceutical formulation comprising the erythropoietin peptide according to claim 1, and a pharmaceutically acceptable carrier.

24. The peptide according to claim 1, wherein said modified sialyl residue has a formula, which is a member selected from:

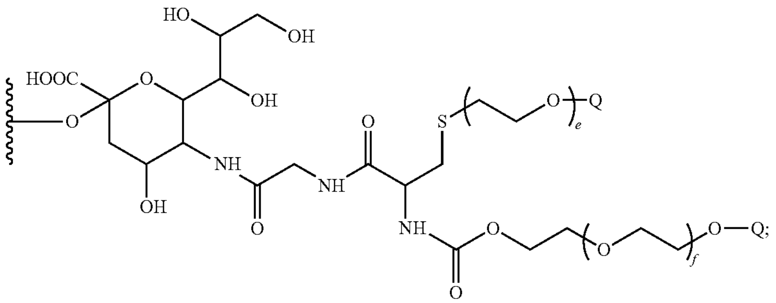

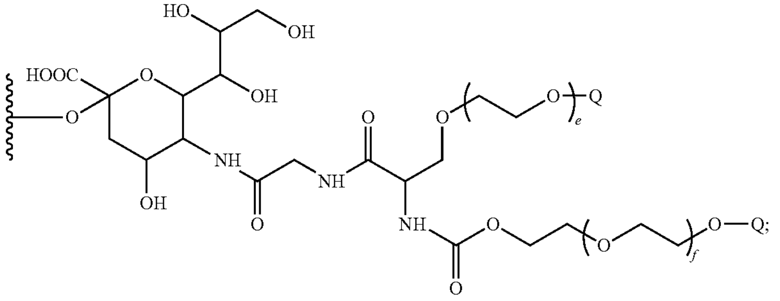

and

-continued

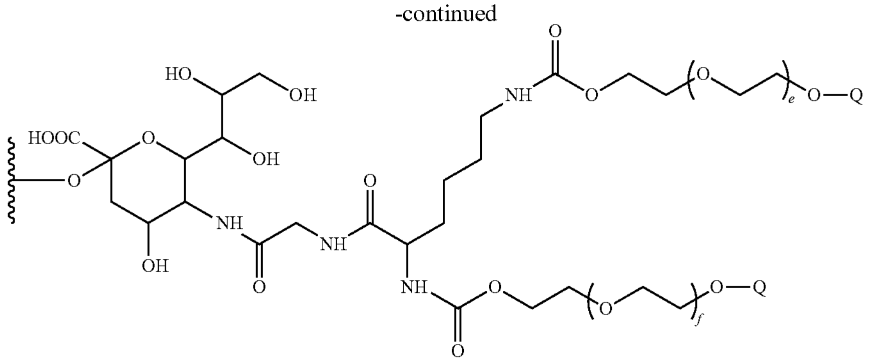

wherein

Q is selected from H and substituted or unsubstituted $C_1$-$C_6$ alkyl; and e and f are integers independently selected from 1 to 2500.

25. The peptide according to claim 1, wherein $R^{16}$ and $R^{17}$ are independently selected poly(ethylene glycol) moieties.

26. An erythropoietin peptide comprising a glycosyl linking group attached to an amino acid residue of said peptide, said glycosyl linking group comprising a modified sialyl residue having the formula:

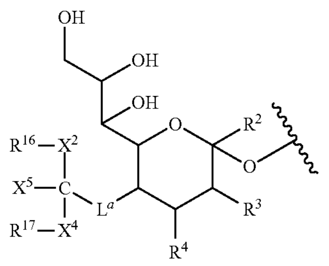

wherein $R^2$ is a member selected from H, $CH_2OR^7$, $COOR^7$, $COO^-$, and $OR^7$ wherein $R^7$ is a member selected from H, substituted or unsubstituted alkyl, and substituted or unsubstituted heteroalkyl;

$R^3$ and $R^4$ are members independently selected from H, substituted or unsubstituted alkyl, $OR^8$, and $NHC(O)R^9$ wherein $R^8$ and $R^9$ are members independently selected from H, substituted or unsubstituted alkyl, substituted or unsubstituted heteroalkyl, and sialic acid;

$L^a$ is a linker selected from C(O)NH and $(CH_2)_jC(O)NH(CH_2)_h(CONH)$, wherein h and j are integers independently selected from 0 to 10;

$R^{16}$ and $R^{17}$ are polymeric moieties independently selected from PEG, dextran, amylose, hyalouronic acid, poly (sialic acid), heparans, heparins, and poly(amino acids);

$X^2$ and $X^4$ are linkage fragments independently selected from S, SC(O)NH, HNC(O)S, SC(O)O, O, NH, NHC(O), (O)CNH, NHC(O)O, OC(O)NH, $CH_2S$, $CH_2O$, $CH_2CH_2O$, and $CH_2CH_2S$; and $X^5$ is a member selected from H, unsubstituted alkyl and unsubstituted heteroalkyl.

27. The peptide according to claim 26, wherein said polymeric moieties are members independently selected from dextran, amylose, hyalouronic acid, poly(sialic acid), heparans, heparins, poly(aspartic acid) and poly(glutamic acid).

28. The peptide according to claim 26, wherein said glycosyl linking group comprises a glycosyl group having the formula:

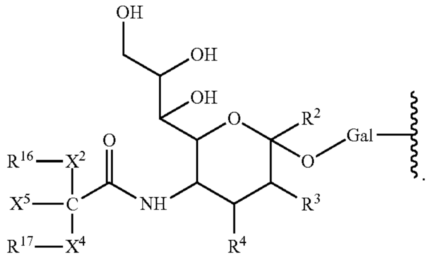

29. The peptide according to claim 28, wherein said glycosyl group has the formula:

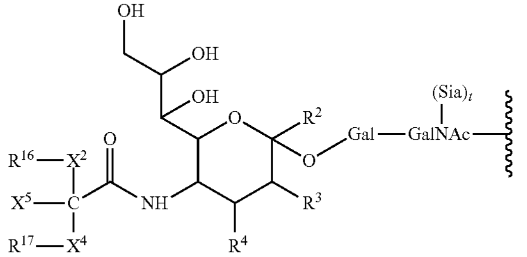

in which t is 0 or 1.

30. The peptide according to claim 29, wherein said glycosyl linking group attached to said amino acid residue has the formula:

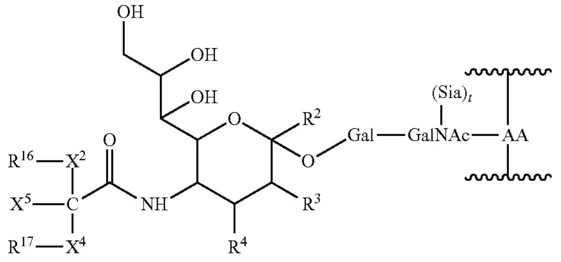

wherein

AA is an amino acid residue of said peptide.

31. The peptide according to claim 30, wherein said amino acid residue is a member selected from serine and threonine.

32. The peptide according to claim 31, wherein said peptide has the amino acid sequence of SEQ ID NO:1.

33. The peptide according to claim 32, wherein said amino acid residue is a serine at position 126 of SEQ ID NO:1.

34. The peptide according to claim 26, wherein said peptide comprises at least one said glycosyl linking group attached to an amino acid residue, said glycosyl linking group comprising a glycosyl group having a formula selected from:

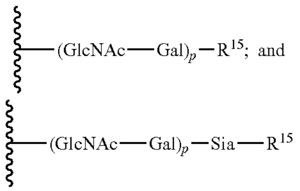

and wherein $R^{15}$ is said modified sialyl residue; and p is an integer from 1 to 10.

35. The peptide according to claim 34, wherein said at least one glycosyl linking group attached to an amino acid residue of said peptide has a formula selected from:

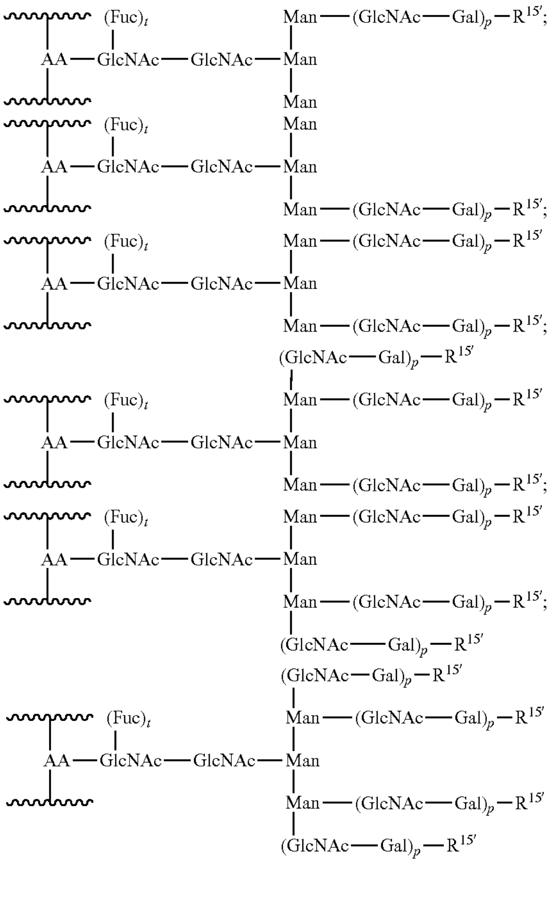

and combinations thereof wherein

AA is an amino acid residue of said peptide;

t is an integer equal to 0 or 1;

p is an integer from 1 to 10; and each $R^{15'}$ is a member independently selected from H, OH, sialic acid, said modified sialyl residue and Sia-$Sia^p$ wherein $Sia^p$ is said modified sialyl residue;

wherein at least one $R^{15'}$ is a member selected from said modified sialyl residue and Sia-$Sia^p$.

36. The peptide according to claim 35, wherein said amino acid residue is an asparagine residue.

37. The peptide according to claim 36, wherein said peptide has the amino acid sequence of SEQ ID NO:1, and wherein said amino acid residue is an asparagine residue which is a member selected from N24, N38, N83, and combinations thereof.

38. The peptide according to claim 37, wherein said glycosyl linking group is attached to N24.

39. The peptide according to claim 26, wherein said peptide is erythropoietically active.

40. The peptide according to claim 26, wherein said peptide is essentially non-erythropoietically active.

41. The peptide according to claim 40, wherein said peptide is tissue protective.

42. A pharmaceutical formulation comprising the erythropoietin peptide according to claim 26 and a pharmaceutically acceptable carrier.

43. A method of enhancing red blood cell production in a mammal, said method comprising administering to said mammal an erythropoietin peptide according to claim 26.

44. A method of treating a tissue injury in a subject in need thereof, said injury resulting from ischemia, trauma, inflammation or contact with toxic substances, said method comprising the step of administering to the subject an amount of an erythropoietin peptide according to claim 26, effective to ameliorate the damage associated with the tissue injury in said subject.

45. A method of treating anemia, comprising administering an erythropoietin peptide according to claim 1 to a subject in need thereof.

46. The method according to claim 45, wherein said anemia is age related anemia, early anemia of prematurity or anemia associated with a member selected from chronic renal failure, cancer chemotherapy treatment, anti-HIV drug treatment, sickle cell disease, beta-thalassemia, cystic fibrosis, pregnancy, menstrual disorders, spinal cord injury, space flight and acute blood loss.

47. A method of treating anemia, comprising administering an erythropoietin peptide according to claim 26 to a subject in need thereof.

48. The method according to claim 47, wherein said anemia is age related anemia, early anemia of prematurity or anemia associated with a member selected from chronic renal failure, cancer chemotherapy treatment, anti-HIV drug treatment, sickle cell disease, beta-thalassemia, cystic fibrosis, pregnancy, menstrual disorders, spinal cord injury, space flight and acute blood loss.

49. An erythropoietin peptide comprising a glycosyl linking group attached to an amino acid residue of said peptide, said glycosyl linking group comprising a sialyl residue covalently linked to the moiety:

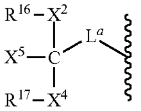

wherein $L^a$ is a linker selected from C(O)NH and $(CH_2)_jC(O)NH(CH_2)_h(CONH)$, wherein h and j are integers independently selected from 0 to 10;

$R^{16}$ and $R^{17}$ are polymeric moieties independently selected from poly(amino) acids and PEG;

$X^2$ and $X^4$ are linkage fragments independently selected from S, SC(O)NH, HNC(O)S, SC(O)O, O, NH, NHC(O), (O)CNH, NHC(O)O, OC(O)NH, $CH_2S$, $CH_2O$, $CH_2CH_2O$, and $CH_2CH_2$; and $X^5$ is a member selected from H, unsubstituted alkyh and unsubstituted heteroalkyl.

50. An erythropoietin peptide comprising a glycosyl linking group attached to an amino acid residue of said peptide, said glycosyl linking group comprising a sialyl residue covalently linked to a member selected from:

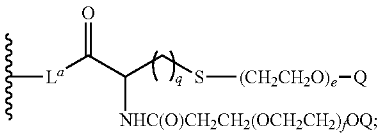

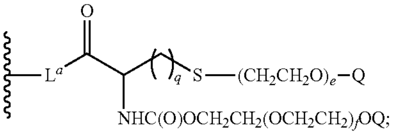

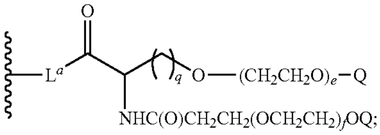

and

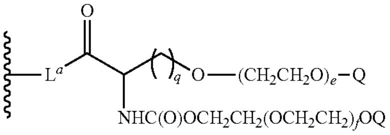

wherein $L^a$ is a linker selected from C(O)NH and $(CH_2)_jC(O)NH(CH_2)_h(CONH)$, wherein h and j are integers independently selected from 0 to 10;

Q is selected from H and substituted or unsubstituted $C_1$-$C_6$ alkyl;

e and f are integers independently selected from 1 to 2500; and q is an integer from 0 to 20.

51. An erythropoietin peptide comprising a glycosyl linking group attached to an amino acid residue of said peptide, said glycosyl linking group comprising a sialyl residue covalently linked to a member selected from:

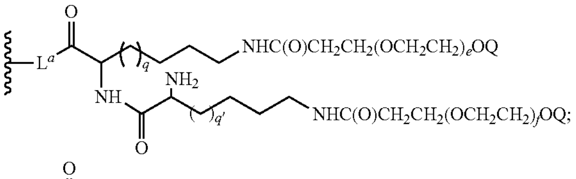

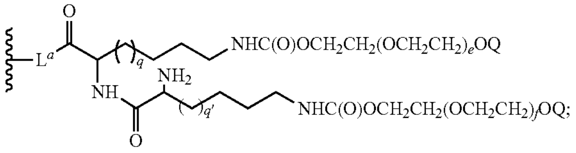

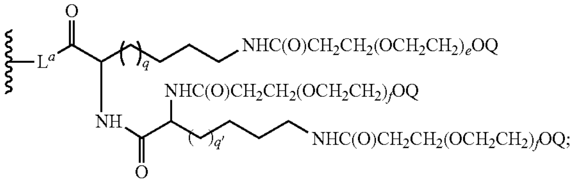

and

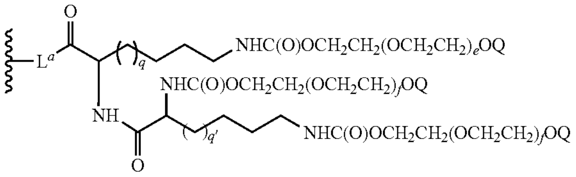

wherein $L^a$ is a linker selected from C(O)NH and $(CH_2)_jC(O)NH(CH_2)_h(CONH)$, wherein h and j are integers independently selected from 0 to 10;

Q is selected from H and substituted or unsubstituted $C_1$-$C_6$ alkyl;

e, f and f' are integers independently selected from 1 to 2500; and q and q' are integers independently selected from 1 to 20.

52. The erythropoietin peptide according to claim 26, wherein each of said polymeric moieties is a poly(amino acid).

53. The erythropoietin peptide according to claim 26, wherein each of said polymeric moieties is a member selected from polyaspartic acid, polyglutamic acid, and polylysine.

* * * * *